US009593365B2

(12) United States Patent
Frisen et al.

(10) Patent No.: US 9,593,365 B2
(45) Date of Patent: *Mar. 14, 2017

(54) METHODS AND PRODUCT FOR OPTIMISING LOCALISED OR SPATIAL DETECTION OF GENE EXPRESSION IN A TISSUE SAMPLE

(71) Applicant: SPATIAL TRANSCRIPTOMICS AB, Stockholm (SE)

(72) Inventors: Jonas Frisen, Stockholm (SE); Patrik Stahl, Stockholm (SE); Joakim Lundeberg, Lidingo (SE); Fredrik Salmen, Stockholm (SE)

(73) Assignee: SPATIAL TRANSCRIPTIONS AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/434,274

(22) PCT Filed: Oct. 16, 2013

(86) PCT No.: PCT/EP2013/071645
§ 371 (c)(1),
(2) Date: Apr. 8, 2015

(87) PCT Pub. No.: WO2014/060483
PCT Pub. Date: Apr. 24, 2014

(65) Prior Publication Data
US 2015/0344942 A1    Dec. 3, 2015

(30) Foreign Application Priority Data

Oct. 17, 2012 (GB) .................................. 1218654.0
Mar. 14, 2013 (GB) .................................. 1304585.1

(51) Int. Cl.
C12Q 1/68        (2006.01)

(52) U.S. Cl.
CPC ......... *C12Q 1/6837* (2013.01); *C12Q 1/6841* (2013.01); *C12Q 1/6874* (2013.01)

(58) Field of Classification Search
None
See application file for complete search history.

(56) References Cited

U.S. PATENT DOCUMENTS

| 4,683,195 | A | 7/1987 | Mullis et al. |
| 4,683,202 | A | 7/1987 | Mullis |
| 4,800,159 | A | 1/1989 | Mullis et al. |
| 4,883,867 | A | 11/1989 | Lee et al. |
| 4,965,188 | A | 10/1990 | Mullis et al. |
| 5,321,130 | A | 6/1994 | Yue et al. |
| 5,410,030 | A | 4/1995 | Yue et al. |
| 5,436,134 | A | 7/1995 | Haugland et al. |
| 5,512,462 | A | 4/1996 | Cheng |
| 5,582,977 | A | 12/1996 | Yue et al. |
| 5,658,751 | A | 8/1997 | Yue et al. |
| 5,863,753 | A | 1/1999 | Haugland et al. |
| 2003/0040043 | A1 | 2/2003 | Slamon et al. |
| 2003/0170637 | A1 | 9/2003 | Pirrung et al. |
| 2004/0067492 | A1 | 4/2004 | Peng et al. |
| 2005/0037362 | A1 | 2/2005 | Remacle et al. |
| 2007/0178503 | A1 | 8/2007 | Jiang |
| 2007/0254305 | A1 | 11/2007 | Paik et al. |
| 2010/0035249 | A1 | 2/2010 | Hayashizaki et al. |
| 2011/0244448 | A1 | 10/2011 | Shirai et al. |
| 2012/0245053 | A1 | 9/2012 | Shirai et al. |

FOREIGN PATENT DOCUMENTS

| WO | 9932654 A1 | 7/1999 |
| WO | 0024940 A1 | 5/2000 |
| WO | 0107915 A2 | 2/2001 |
| WO | 0142796 A1 | 6/2001 |
| WO | 0224952 A1 | 3/2002 |
| WO | 02077283 A1 | 10/2002 |
| WO | 02088396 A2 | 11/2002 |
| WO | 2012140224 A1 | 10/2012 |

OTHER PUBLICATIONS

Mitsuhashi et al, Nature 357: 519 (1992).*
Eberwine, BioTechniques 20 (4), 584 (996).*
Andersson et al.; "Analysis of Protein Expression in Cell Microarrays: A Tool for Antibody-based Proteomics"; Journal of Histochemistry & Cytochemistry; 54(12); pp. 1413-1423; (2006).
Barnes, Wayne M.; "PCR Amplification of Up to 35-kb DNA With High Fidelity and High Yield from A Bacteriophage Templates"; Proc. Natl. Acad. Sci. USA; 91; pp. 2216-2220; (1994).
Burton et al.; "Coverslip Mounted-Immersion Cycled in Situ RT-PCR for the Localization of mRNA in Tissue Sections"; Biotechniques; 24; pp. 92-100; (1998).
GB1218654.0, filed Oct. 17, 2012, Search Report dated May 29, 2013, 2 pages.
Shirai et al.; "Novel Tools for Analyzing Gene Expressions in Single Cells"; Nature Methods; 6; pp. 503-506; (2009) _Abstract only.
Lundberg et al.; "High-fidelity Amplification Using a Thermostable DNA Polmerase Isolated from Pyrococcus Furiosus"; Gene; 108; pp. 1-6; (1991).
Perler et al.; "Intervening Sequences in an Archaea DNA Polymmerase Gene"; Proc. Natl. Acad. Sci. USA; 89; pp. 5577-5581; (1992).
Pettersson et al.; "Generations of Sequencing Technologies"; Genomics; 93; pp. 105-111; (2009).

(Continued)

*Primary Examiner* — James Martinell
(74) *Attorney, Agent, or Firm* — Cantor Colburn LLP

(57) ABSTRACT

The present invention relates to methods and products for localized or spatial detection and/or analysis of RNA in a tissue sample or a portion thereof, comprising: (a) providing an object substrate on which at least one species of capture probe, comprising a capture domain, is directly or indirectly immobilized such that the probes are oriented to have a free 3' end to enable said probe to function as a reverse transcriptase (RT) primer; (b) contacting said substrate with a tissue sample and allowing RNA of the tissue sample to hybridize to the capture probes; (c) generating cDNA molecules from the captured RNA molecules using said capture probes as RT primers; (d) labelling the cDNA molecules generated in step (c), wherein said labelling step may be contemporaneous with, or subsequent to, said generating step; (e) detecting a signal from the labelled cDNA molecules; and optionally (f) imaging the tissue sample, wherein the tissue sample is imaged before or after step (c).

43 Claims, 17 Drawing Sheets

(56) References Cited

OTHER PUBLICATIONS

Rubin et al.; "Whole-genome Resequencing Reveals Loci Under Selection During Chicken Domestication"; Nature; 464; pp. 587-591; (2010).

Schena et al.; "Quantitative Monitoring of Gene Expression Patterns with a Complementary DNA Microarray"; Science; 270(5235); pp. 467-470; (1995).

Tang et al.; "RNA-Seq Analysis to Capture the Transcriptome Landscape of a Single Cell"; Nat Protoc. 5(3); pp. 1-34; (2010); Author Manuscript in Europ PMC Funders Group, Nat Protoc. Author Manuscript, available in PMC Dec. 3, 2013.

Wade et al.; Genome Sequence, Comparative Analysis and Population Genetics of the Domestic Horse (*Equus caballus*); Science; 326(5954); pp. 865-867; (2009).

Wang et al.; "Single Cell Analysis: The New Frontier in 'Omics'"; Trends in Biotechnology; 28(6); pp. 281-290; (2010).

Eguiluz et al.; "Multitissue Array Review: A Chronological Description of Tissue Array Techniques, Applications and Procedures"; Pathology—Research and Practice; 202; pp. 561-568; (2006).

International Search Report and Written Opinion; International Application No. PCT/EP2013/071645; International Filing Date Oct. 16, 2013; Date of Mailing Dec. 11, 2013; 12 pages.

EP Aplication 13780111.4 Office Action of Jul. 7, 2016; 6 pages.

\* cited by examiner

A Tissue with diffusing RNA

B Tissue with diffusing RNA

C Tissue with diffusing RNA

SEQUENCE LISTING

```
<160> NUMBER OF SEQ ID NOS: 139

<210> SEQ ID NO 1
<211> LENGTH: 72
<212> TYPE: DNA
<213> ORGANISM: Artificial Sequence
<220> FEATURE:
<223> OTHER INFORMATION: synthesized sequence
<220> FEATURE:
<221> NAME/KEY: misc_feature
<222> LOCATION: (1)..(1)
<223> OTHER INFORMATION: 5'-terminus amino linker with a C6 spacer
<220> FEATURE:
<221> NAME/KEY: misc_feature
<222> LOCATION: (72)..(72)
<223> OTHER INFORMATION: n is a, c, g, t or u
```

<400> SEQUENCE: 1
uuaagtacaa atctcgactg ccactctgaa ccttctcctt ctccttcacc tttttttttt    60
tttttttttt vn                                                        72

<210> SEQ ID NO 2
<211> LENGTH: 10
<212> TYPE: DNA
<213> ORGANISM: Artificial Sequence
<220> FEATURE:
<223> OTHER INFORMATION: synthesized Enzymatic recognition sequence

<400> SEQUENCE: 2
uuaagtacaa                                                           10

<210> SEQ ID NO 3
<211> LENGTH: 20
<212> TYPE: DNA
<213> ORGANISM: Artificial Sequence
<220> FEATURE:
<223> OTHER INFORMATION: synthesized Universal amplification handle P

<400> SEQUENCE: 3
atctcgactg ccactctgaa                                                20

<210> SEQ ID NO 4
<211> LENGTH: 20
<212> TYPE: DNA
<213> ORGANISM: Artificial sequence
<220> FEATURE:
<223> OTHER INFORMATION: synthesized sequence

<400> SEQUENCE: 4
ccttctcctt ctccttcacc                                                20

<210> SEQ ID NO 5
<211> LENGTH: 22
<212> TYPE: DNA
<213> ORGANISM: Artificial sequence
<220> FEATURE:
<223> OTHER INFORMATION: synthesized Capture sequence
<220> FEATURE:
<221> NAME/KEY: misc_feature
<222> LOCATION: (22)..(22)
<223> OTHER INFORMATION: n is a, c, g, or t

<400> SEQUENCE: 5
tttttttttt tttttttttt vn                                             22

<210> SEQ ID NO 6
<211> LENGTH: 20
<212> TYPE: DNA
<213> ORGANISM: Artificial sequence
<220> FEATURE:
<223> OTHER INFORMATION: synthesized Tag sequence

<400> SEQUENCE: 6
ccttctcctt ctccttcacc                                                20

<210> SEQ ID NO 7
<211> LENGTH: 20
<212> TYPE: DNA
<213> ORGANISM: Artificial sequence
<220> FEATURE:
<223> OTHER INFORMATION: synthesied Tag sequence

```
<400> SEQUENCE: 7
ccttgctgct tctcctcctc                                               20

<210> SEQ ID NO 8
<211> LENGTH: 20
<212> TYPE: DNA
<213> ORGANISM: Artificial sequence
<220> FEATURE:
<223> OTHER INFORMATION: synthesized Tag sequence

<400> SEQUENCE: 8
acctcctccg cctcctcctc                                               20

<210> SEQ ID NO 9
<211> LENGTH: 20
<212> TYPE: DNA
<213> ORGANISM: Artificial sequence
<220> FEATURE:
<223> OTHER INFORMATION: synthesized Tag sequence

<400> SEQUENCE: 9
gagacatacc accaagagac                                               20

<210> SEQ ID NO 10
<211> LENGTH: 20
<212> TYPE: DNA
<213> ORGANISM: Artificial sequence
<220> FEATURE:
<223> OTHER INFORMATION: synthesized Tag sequence

<400> SEQUENCE: 10
gtcctctatt ccgtcaccat                                               20

<210> SEQ ID NO 11
<211> LENGTH: 20
<212> TYPE: DNA
<213> ORGANISM: Artificial sequence
<220> FEATURE:
<223> OTHER INFORMATION: synthesized Tag sequence

<400> SEQUENCE: 11
gactgagctc gaacatatgg                                               20

<210> SEQ ID NO 12
<211> LENGTH: 20
<212> TYPE: DNA
<213> ORGANISM: Artificial sequence
<220> FEATURE:
<223> OTHER INFORMATION: synthesized Tag sequence

<400> SEQUENCE: 12
tggaggattg acacagaacg                                               20

<210> SEQ ID NO 13
<211> LENGTH: 20
<212> TYPE: DNA
<213> ORGANISM: Artificial sequence
<220> FEATURE:
<223> OTHER INFORMATION: synthesized Tag sequence

<400> SEQUENCE: 13
ccagcctctc cattacatcg                                               20

<210> SEQ ID NO 14
<211> LENGTH: 20
```

```
<212> TYPE: DNA
<213> ORGANISM: Artificial sequence
<220> FEATURE:
<223> OTHER INFORMATION: synthesized Tag sequence

<400> SEQUENCE: 14
aagatctacc agccagccag                                              20

<210> SEQ ID NO 15
<211> LENGTH: 20
<212> TYPE: DNA
<213> ORGANISM: Artificial sequence
<220> FEATURE:
<223> OTHER INFORMATION: synthesized Tag sequence

<400> SEQUENCE: 15
cgaacttcca ctgtctcctc                                              20

<210> SEQ ID NO 16
<211> LENGTH: 20
<212> TYPE: DNA
<213> ORGANISM: Artificial sequence
<220> FEATURE:
<223> OTHER INFORMATION: synthesized Tag sequence

<400> SEQUENCE: 16
ttgcgccttc tccaatacac                                              20

<210> SEQ ID NO 17
<211> LENGTH: 20
<212> TYPE: DNA
<213> ORGANISM: Artificial sequence
<220> FEATURE:
<223> OTHER INFORMATION: synthesized Tag sequence

<400> SEQUENCE: 17
ctcttcttag catgccacct                                              20

<210> SEQ ID NO 18
<211> LENGTH: 20
<212> TYPE: DNA
<213> ORGANISM: Artificial sequence
<220> FEATURE:
<223> OTHER INFORMATION: synthesized Tag sequence

<400> SEQUENCE: 18
accacttctg cattacctcc                                              20

<210> SEQ ID NO 19
<211> LENGTH: 20
<212> TYPE: DNA
<213> ORGANISM: Artificial sequence
<220> FEATURE:
<223> OTHER INFORMATION: synthesized Tag sequence

<400> SEQUENCE: 19
acagcctcct cttcttcctt                                              20

<210> SEQ ID NO 20
<211> LENGTH: 20
<212> TYPE: DNA
<213> ORGANISM: Artificial sequence
<220> FEATURE:
<223> OTHER INFORMATION: synthesized Tag sequence

<400> SEQUENCE: 20
```
aatcctctcc ttgccagttc                                               20

<210> SEQ ID NO 21
<211> LENGTH: 20
<212> TYPE: DNA
<213> ORGANISM: Artificial sequence
<220> FEATURE:
<223> OTHER INFORMATION: synthesized Tag sequence

<400> SEQUENCE: 21
gatgcctcca cctgtagaac                                               20

<210> SEQ ID NO 22
<211> LENGTH: 20
<212> TYPE: DNA
<213> ORGANISM: Artificial sequence
<220> FEATURE:
<223> OTHER INFORMATION: synthesized Tag sequence

<400> SEQUENCE: 22
gaaggaatgg aggatatcgc                                               20

<210> SEQ ID NO 23
<211> LENGTH: 20
<212> TYPE: DNA
<213> ORGANISM: Artificial sequence
<220> FEATURE:
<223> OTHER INFORMATION: synthesized Tag sequence

<400> SEQUENCE: 23
gatccaagga ccatcgactg                                               20

<210> SEQ ID NO 24
<211> LENGTH: 20
<212> TYPE: DNA
<213> ORGANISM: Artificial sequence
<220> FEATURE:
<223> OTHER INFORMATION: synthesized Tag sequence

<400> SEQUENCE: 24
ccactggaac ctgacaaccg                                               20

<210> SEQ ID NO 25
<211> LENGTH: 20
<212> TYPE: DNA
<213> ORGANISM: Artificial sequence
<220> FEATURE:
<223> OTHER INFORMATION: synthesized Tag sequence

<400> SEQUENCE: 25
ctgcttcttc ctggaactca                                               20

<210> SEQ ID NO 26
<211> LENGTH: 66
<212> TYPE: DNA
<213> ORGANISM: Artificial sequence
<220> FEATURE:
<223> OTHER INFORMATION: synthesized Free 5' surface probe - A
<220> FEATURE:
<221> NAME/KEY: misc_feature
<222> LOCATION: (66)..(66)
<223> OTHER INFORMATION: 3'-terminus amino linker with a C7 spacer

<400> SEQUENCE: 26
gcgttcagag tggcagtcga gatcacgcgg caatcatatc ggacagatcg gaagagcgta   60
gtgtag                                                              66

-continued

<210> SEQ ID NO 27
<211> LENGTH: 66
<212> TYPE: DNA
<213> ORGANISM: Artificial sequence
<220> FEATURE:
<223> OTHER INFORMATION: synthesized Free 5' surface probe - U
<220> FEATURE:
<221> NAME/KEY: misc_feature
<222> LOCATION: (66)..(66)
<223> OTHER INFORMATION: 3'-terminus amino linker with a C7 spacer

<400> SEQUENCE: 27
gcgttcagag tggcagtcga gatcacgcgg caatcatatc ggacggctgc tggtaaatag     60
agatca                                                                66

<210> SEQ ID NO 28
<211> LENGTH: 23
<212> TYPE: DNA
<213> ORGANISM: Artificial sequence
<220> FEATURE:
<223> OTHER INFORMATION: synthesized Longer universal amplification
      handle

<400> SEQUENCE: 28
ttcagagtgg cagtcgagat cac                                             23

<210> SEQ ID NO 29
<211> LENGTH: 18
<212> TYPE: DNA
<213> ORGANISM: Artificial sequence
<220> FEATURE:
<223> OTHER INFORMATION: synthesized Tag sequence

<400> SEQUENCE: 29
gcggcaatca tatcggac                                                   18

<210> SEQ ID NO 30
<211> LENGTH: 22
<212> TYPE: DNA
<213> ORGANISM: Artificial sequence
<220> FEATURE:
<223> OTHER INFORMATION: synthesized A' 22bp MutY mismatch

<400> SEQUENCE: 30
agatcggaag agcgtagtgt ag                                              22

<210> SEQ ID NO 31
<211> LENGTH: 22
<212> TYPE: DNA
<213> ORGANISM: Artificial sequence
<220> FEATURE:
<223> OTHER INFORMATION: synthesized U' 22bp MutY mismatch

<400> SEQUENCE: 31
ggctgctggt aaatagagat ca                                              22

<210> SEQ ID NO 32
<211> LENGTH: 33
<212> TYPE: DNA
<213> ORGANISM: Artificial sequence
<220> FEATURE:
<223> OTHER INFORMATION: synthesized Illumina amplification handle A

<400> SEQUENCE: 32
acactctttc cctacacgac gctcttccga tct                                  33

<210> SEQ ID NO 33
<211> LENGTH: 35
<212> TYPE: DNA
<213> ORGANISM: Artificial sequence
<220> FEATURE:
<223> OTHER INFORMATION: synthesized Universal amplification handle U

<400> SEQUENCE: 33
aagtgtggaa agttgatcgc tatttaccag cagcc            35

<210> SEQ ID NO 34
<211> LENGTH: 45
<212> TYPE: DNA
<213> ORGANISM: Artificial sequence
<220> FEATURE:
<223> OTHER INFORMATION: synthesized Capture LP Poly-dTVN
<220> FEATURE:
<221> NAME/KEY: misc_feature
<222> LOCATION: (1)..(1)
<223> OTHER INFORMATION: Phosphorylated
<220> FEATURE:
<221> NAME/KEY: misc_feature
<222> LOCATION: (45)..(45)
<223> OTHER INFORMATION: n is a, c, g, or t

<400> SEQUENCE: 34
gtgatctcga ctgccactct gaattttttt tttttttttt tttvn            45

<210> SEQ ID NO 35
<211> LENGTH: 47
<212> TYPE: DNA
<213> ORGANISM: Artificial sequence
<220> FEATURE:
<223> OTHER INFORMATION: synthesized Capture LP Poly-d24T
<220> FEATURE:
<221> NAME/KEY: misc_feature
<222> LOCATION: (1)..(1)
<223> OTHER INFORMATION: Phosphorylated

<400> SEQUENCE: 35
gtgatctcga ctgccactct gaattttttt tttttttttt ttttttt            47

<210> SEQ ID NO 36
<211> LENGTH: 21
<212> TYPE: DNA
<213> ORGANISM: Artificial sequence
<220> FEATURE:
<223> OTHER INFORMATION: synthesized Illumina amplification handle B

<400> SEQUENCE: 36
agacgtgtgc tcttccgatc t            21

<210> SEQ ID NO 37
<211> LENGTH: 20
<212> TYPE: DNA
<213> ORGANISM: Artificial sequence
<220> FEATURE:
<223> OTHER INFORMATION: synthesized Universal amplification handle X

<400> SEQUENCE: 37
acgtctgtga atagccgcat            20

<210> SEQ ID NO 38
<211> LENGTH: 29
<212> TYPE: DNA
<213> ORGANISM: Artificial sequence
<220> FEATURE:

```
<223> OTHER INFORMATION: synthesized B R6 handle (or X)
<220> FEATURE:
<221> NAME/KEY: misc_feature
<222> LOCATION: (22)..(29)
<223> OTHER INFORMATION: n is a, c, g, or t

<400> SEQUENCE: 38
agacgtgtgc tcttccgatc tnnnnnnnn                                    29

<210> SEQ ID NO 39
<211> LENGTH: 31
<212> TYPE: DNA
<213> ORGANISM: Artificial sequence
<220> FEATURE:
<223> OTHER INFORMATION: synthesized B R8 handle (or X)
<220> FEATURE:
<221> NAME/KEY: misc_feature
<222> LOCATION: (22)..(31)
<223> OTHER INFORMATION: n is a, c, g, or t

<400> SEQUENCE: 39
agacgtgtgc tcttccgatc tnnnnnnnnn n                                 31

<210> SEQ ID NO 40
<211> LENGTH: 43
<212> TYPE: DNA
<213> ORGANISM: Artificial sequence
<220> FEATURE:
<223> OTHER INFORMATION: synthesized B polyTVN (or X)
<220> FEATURE:
<221> NAME/KEY: misc_feature
<222> LOCATION: (43)..(43)
<223> OTHER INFORMATION: n is a, c, g, or t

<400> SEQUENCE: 40
agacgtgtgc tcttccgatc tttttttttt tttttttttt tvn                    43

<210> SEQ ID NO 41
<211> LENGTH: 45
<212> TYPE: DNA
<213> ORGANISM: Artificial sequence
<220> FEATURE:
<223> OTHER INFORMATION: synthesized B poly24T (or X)

<400> SEQUENCE: 41
agacgtgtgc tcttccgatc tttttttttt tttttttttt ttttt                  45

<210> SEQ ID NO 42
<211> LENGTH: 53
<212> TYPE: DNA
<213> ORGANISM: Artificial sequence
<220> FEATURE:
<223> OTHER INFORMATION: synthesized A P handle

<400> SEQUENCE: 42
acactctttc cctacacgac gctcttccga tctatctcga ctgccactct gaa          53

<210> SEQ ID NO 43
<211> LENGTH: 20
<212> TYPE: DNA
<213> ORGANISM: Artificial sequence
<220> FEATURE:
<223> OTHER INFORMATION: synthesized Beta-2 microglobulin (B2M) primer

<400> SEQUENCE: 43
tgggggtgag aattgctaag                                              20
```

-continued

```
<210> SEQ ID NO 44
<211> LENGTH: 20
<212> TYPE: DNA
<213> ORGANISM: Artificial sequence
<220> FEATURE:
<223> OTHER INFORMATION: synthesized ID-1 primer

<400> SEQUENCE: 44
ccttctcctt ctccttcacc                                                    20

<210> SEQ ID NO 45
<211> LENGTH: 20
<212> TYPE: DNA
<213> ORGANISM: Artificial sequence
<220> FEATURE:
<223> OTHER INFORMATION: synthesized ID-5 primer

<400> SEQUENCE: 45
gtcctctatt ccgtcaccat                                                    20

<210> SEQ ID NO 46
<211> LENGTH: 20
<212> TYPE: DNA
<213> ORGANISM: Artificial sequence
<220> FEATURE:
<223> OTHER INFORMATION: synthesized ID-20 primer

<400> SEQUENCE: 46
ctgcttcttc ctggaactca                                                    20

<210> SEQ ID NO 47
<211> LENGTH: 75
<212> TYPE: DNA
<213> ORGANISM: Artificial sequence
<220> FEATURE:
<223> OTHER INFORMATION: synthesized Probe 1
<220> FEATURE:
<221> NAME/KEY: misc_feature
<222> LOCATION: (1)..(1)
<223> OTHER INFORMATION: 5'-terminus amino linker with a C6 spacer
<220> FEATURE:
<221> NAME/KEY: misc_feature
<222> LOCATION: (75)..(75)
<223> OTHER INFORMATION: n is a, c, g, t or u

<400> SEQUENCE: 47
uuacactctt tccctacacg acgctcttcc gatctgtccg atatgattgc cgcttttttt        60
tttttttttt tttvn                                                         75

<210> SEQ ID NO 48
<211> LENGTH: 33
<212> TYPE: DNA
<213> ORGANISM: Artificial sequence
<220> FEATURE:
<223> OTHER INFORMATION: synthesized A Primer

<400> SEQUENCE: 48
acactctttc cctacacgac gctcttccga tct                                     33

<210> SEQ ID NO 49
<211> LENGTH: 43
<212> TYPE: DNA
<213> ORGANISM: Artificial sequence
<220> FEATURE:
<223> OTHER INFORMATION: synthesized B_dt20VN_primer
<220> FEATURE:
<221> NAME/KEY: misc_feature
<222> LOCATION: (43)..(43)
```

<223> OTHER INFORMATION: n is a, c, g, or t

<400> SEQUENCE: 49
agacgtgtgc tcttccgatc tttttttttt tttttttttt tvn    43

<210> SEQ ID NO 50
<211> LENGTH: 78
<212> TYPE: DNA
<213> ORGANISM: Artificial sequence
<220> FEATURE:
<223> OTHER INFORMATION: synthesized Probe 1
<220> FEATURE:
<221> NAME/KEY: misc_feature
<222> LOCATION: (78)..(78)
<223> OTHER INFORMATION: n is a, c, g, t or u

<400> SEQUENCE: 50
uuuuuacact ctttccctac acgacgctct tccgatctgt ccgatatgat tgccgcttttt    60 tttttttttt tttttvn    78

<210> SEQ ID NO 51
<211> LENGTH: 78
<212> TYPE: DNA
<213> ORGANISM: Artificial sequence
<220> FEATURE:
<223> OTHER INFORMATION: synthesized Probe 2
<220> FEATURE:
<221> NAME/KEY: misc_feature
<222> LOCATION: (78)..(78)
<223> OTHER INFORMATION: n is a, c, g, t or u

<400> SEQUENCE: 51
uuuuuacact ctttccctac acgacgctct tccgatctat gagccgggtt catcttttttt    60 tttttttttt tttttvn    78

<210> SEQ ID NO 52
<211> LENGTH: 78
<212> TYPE: DNA
<213> ORGANISM: Artificial sequence
<220> FEATURE:
<223> OTHER INFORMATION: synthesized Probe 3
<220> FEATURE:
<221> NAME/KEY: misc_feature
<222> LOCATION: (78)..(78)
<223> OTHER INFORMATION: n is a, c, g, t or u

<400> SEQUENCE: 52
uuuuuacact ctttccctac acgacgctct tccgatcttg aggcactctg ttgggatttt    60
tttttttttt tttttvn    78

<210> SEQ ID NO 53
<211> LENGTH: 78
<212> TYPE: DNA
<213> ORGANISM: Artificial sequence
<220> FEATURE:
<223> OTHER INFORMATION: synthesized Probe 4
<220> FEATURE:
<221> NAME/KEY: misc_feature
<222> LOCATION: (78)..(78)
<223> OTHER INFORMATION: n is a, c, g, t or u

<400> SEQUENCE: 53
uuuuuacact ctttccctac acgacgctct tccgatctat gattagtcgc cattcgtttt    60
tttttttttt tttttvn    78

<210> SEQ ID NO 54
<211> LENGTH: 78
<212> TYPE: DNA
<213> ORGANISM: Artificial sequence
<220> FEATURE:
<223> OTHER INFORMATION: synthesized Probe 5
<220> FEATURE:
<221> NAME/KEY: misc_feature
<222> LOCATION: (78)..(78)
<223> OTHER INFORMATION: n is a, c, g, t or u

<400> SEQUENCE: 54
uuuuuacact ctttccctac acgacgctct tccgatctac ttgagggtag atgttttttt    60 ttttttttt ttttttvn                                                   78

<210> SEQ ID NO 55
<211> LENGTH: 78
<212> TYPE: DNA
<213> ORGANISM: Artificial sequence
<220> FEATURE:
<223> OTHER INFORMATION: synthesized Probe 6
<220> FEATURE:
<221> NAME/KEY: misc_feature
<222> LOCATION: (78)..(78)
<223> OTHER INFORMATION: n is a, c, g, t or u

<400> SEQUENCE: 55
uuuuuacact ctttccctac acgacgctct tccgatctat ggccaatact gttatctttt    60 ttttttttt ttttttvn                                                   78

<210> SEQ ID NO 56
<211> LENGTH: 78
<212> TYPE: DNA
<213> ORGANISM: Artificial sequence
<220> FEATURE:
<223> OTHER INFORMATION: synthesized Probe 7
<220> FEATURE:
<221> NAME/KEY: misc_feature
<222> LOCATION: (78)..(78)
<223> OTHER INFORMATION: n is a, c, g, t or u

<400> SEQUENCE: 56
uuuuuacact ctttccctac acgacgctct tccgatctcg ctaccctgat tcgaccttt     60 ttttttttt ttttttvn                                                   78

<210> SEQ ID NO 57
<211> LENGTH: 78
<212> TYPE: DNA
<213> ORGANISM: Artificial sequence
<220> FEATURE:
<223> OTHER INFORMATION: synthesized Probe 8
<220> FEATURE:
<221> NAME/KEY: misc_feature
<222> LOCATION: (78)..(78)
<223> OTHER INFORMATION: n is a, c, g, t or u

<400> SEQUENCE: 57
uuuuuacact ctttccctac acgacgctct tccgatctgc ccactttcgc cgtagttttt    60 ttttttttt ttttttvn                                                   78

<210> SEQ ID NO 58
<211> LENGTH: 78
<212> TYPE: DNA
<213> ORGANISM: Artificial sequence
<220> FEATURE:
<223> OTHER INFORMATION: synthesized Probe 9
<220> FEATURE:

```
<221> NAME/KEY: misc_feature
<222> LOCATION: (78)..(78)
<223> OTHER INFORMATION: n is a, c, g, t or u

<400> SEQUENCE: 58
uuuuuacact ctttccctac acgacgctct tccgatctag caactttgag caagattttt      60
tttttttttt tttttttvn                                                  78

<210> SEQ ID NO 59
<211> LENGTH: 78
<212> TYPE: DNA
<213> ORGANISM: Artificial sequence
<220> FEATURE:
<223> OTHER INFORMATION: synthesized Probe 10
<220> FEATURE:
<221> NAME/KEY: misc_feature
<222> LOCATION: (78)..(78)
<223> OTHER INFORMATION: n is a, c, g, t or u

<400> SEQUENCE: 59
uuuuuacact ctttccctac acgacgctct tccgatctgc caattcggaa ttccggtttt      60
tttttttttt tttttttvn                                                  78

<210> SEQ ID NO 60
<211> LENGTH: 78
<212> TYPE: DNA
<213> ORGANISM: Artificial sequence
<220> FEATURE:
<223> OTHER INFORMATION: synthesized Probe 11
<220> FEATURE:
<221> NAME/KEY: misc_feature
<222> LOCATION: (78)..(78)
<223> OTHER INFORMATION: n is a, c, g, t or u

<400> SEQUENCE: 60
uuuuuacact ctttccctac acgacgctct tccgatcttc gcccaaggta atacattttt      60
tttttttttt tttttttvn                                                  78

<210> SEQ ID NO 61
<211> LENGTH: 78
<212> TYPE: DNA
<213> ORGANISM: Artificial sequence
<220> FEATURE:
<223> OTHER INFORMATION: synthesized Probe 12
<220> FEATURE:
<221> NAME/KEY: misc_feature
<222> LOCATION: (78)..(78)
<223> OTHER INFORMATION: n is a, c, g, t or u

<400> SEQUENCE: 61
uuuuuacact ctttccctac acgacgctct tccgatcttc gcatttccta ttcgagtttt      60
tttttttttt tttttttvn                                                  78

<210> SEQ ID NO 62
<211> LENGTH: 78
<212> TYPE: DNA
<213> ORGANISM: Artificial sequence
<220> FEATURE:
<223> OTHER INFORMATION: synthesized Probe 13
<220> FEATURE:
<221> NAME/KEY: misc_feature
<222> LOCATION: (78)..(78)
<223> OTHER INFORMATION: n is a, c, g, t or u

<400> SEQUENCE: 62
uuuuuacact ctttccctac acgacgctct tccgatcttt gctaaatcta accgcctttt      60
```
tttttttttt tttttvn    78

<210> SEQ ID NO 63
<211> LENGTH: 78
<212> TYPE: DNA
<213> ORGANISM: Artificial sequence
<220> FEATURE:
<223> OTHER INFORMATION: synthesized Probe 14
<220> FEATURE:
<221> NAME/KEY: misc_feature
<222> LOCATION: (78)..(78)
<223> OTHER INFORMATION: n is a, c, g, t or u

<400> SEQUENCE: 63
uuuuuacact ctttccctac acgacgctct tccgatctgg aattaaattc tgatggtttt    60
tttttttttt tttttvn    78

<210> SEQ ID NO 64
<211> LENGTH: 78
<212> TYPE: DNA
<213> ORGANISM: Artificial sequence
<220> FEATURE:
<223> OTHER INFORMATION: synthesized Probe 15
<220> FEATURE:
<221> NAME/KEY: misc_feature
<222> LOCATION: (78)..(78)
<223> OTHER INFORMATION: n is a, c, g, t or u

<400> SEQUENCE: 64
uuuuuacact ctttccctac acgacgctct tccgatctca ttacataggt gctaagtttt    60
tttttttttt tttttvn    78

<210> SEQ ID NO 65
<211> LENGTH: 78
<212> TYPE: DNA
<213> ORGANISM: Artificial sequence
<220> FEATURE:
<223> OTHER INFORMATION: synthesized Probe 16
<220> FEATURE:
<221> NAME/KEY: misc_feature
<222> LOCATION: (78)..(78)
<223> OTHER INFORMATION: n is a, c, g, t or u

<400> SEQUENCE: 65
uuuuuacact ctttccctac acgacgctct tccgatctat tgacttgcgc tcgcactttt    60
tttttttttt tttttvn    78

<210> SEQ ID NO 66
<211> LENGTH: 78
<212> TYPE: DNA
<213> ORGANISM: Artificial sequence
<220> FEATURE:
<223> OTHER INFORMATION: synthesized Probe 17
<220> FEATURE:
<221> NAME/KEY: misc_feature
<222> LOCATION: (78)..(78)
<223> OTHER INFORMATION: n is a, c, g, t or u

<400> SEQUENCE: 66
uuuuuacact ctttccctac acgacgctct tccgatctat agtatctccc aagttctttt    60
tttttttttt tttttvn    78

<210> SEQ ID NO 67
<211> LENGTH: 78
<212> TYPE: DNA

-continued

```
<213> ORGANISM: Artificial sequence
<220> FEATURE:
<223> OTHER INFORMATION: synthesized Probe 18
<220> FEATURE:
<221> NAME/KEY: misc_feature
<222> LOCATION: (78)..(78)
<223> OTHER INFORMATION: n is a, c, g, t or u

<400> SEQUENCE: 67
uuuuuacact ctttccctac acgacgctct tccgatctgt gcgcctgtaa tccgcatttt    60
tttttttttt ttttttvn                                                 78

<210> SEQ ID NO 68
<211> LENGTH: 78
<212> TYPE: DNA
<213> ORGANISM: Artificial sequence
<220> FEATURE:
<223> OTHER INFORMATION: synthesized Probe 19
<220> FEATURE:
<221> NAME/KEY: misc_feature
<222> LOCATION: (78)..(78)
<223> OTHER INFORMATION: n is a, c, g, t or u

<400> SEQUENCE: 68
uuuuuacact ctttccctac acgacgctct tccgatctgc gccactcttt aggtagtttt    60
tttttttttt ttttttvn                                                 78

<210> SEQ ID NO 69
<211> LENGTH: 78
<212> TYPE: DNA
<213> ORGANISM: Artificial sequence
<220> FEATURE:
<223> OTHER INFORMATION: synthesized Probe 20
<220> FEATURE:
<221> NAME/KEY: misc_feature
<222> LOCATION: (78)..(78)
<223> OTHER INFORMATION: n is a, c, g, t or u

<400> SEQUENCE: 69
uuuuuacact ctttccctac acgacgctct tccgatctta tgcaagtgat tggctttttt    60
tttttttttt ttttttvn                                                 78

<210> SEQ ID NO 70
<211> LENGTH: 78
<212> TYPE: DNA
<213> ORGANISM: Artificial sequence
<220> FEATURE:
<223> OTHER INFORMATION: synthesized Probe 21
<220> FEATURE:
<221> NAME/KEY: misc_feature
<222> LOCATION: (78)..(78)
<223> OTHER INFORMATION: n is a, c, g, t or u

<400> SEQUENCE: 70
uuuuuacact ctttccctac acgacgctct tccgatctcc aagccacgtt tatacgtttt    60
tttttttttt ttttttvn                                                 78

<210> SEQ ID NO 71
<211> LENGTH: 78
<212> TYPE: DNA
<213> ORGANISM: Artificial sequence
<220> FEATURE:
<223> OTHER INFORMATION: synthesized Probe 22
<220> FEATURE:
<221> NAME/KEY: misc_feature
<222> LOCATION: (78)..(78)
<223> OTHER INFORMATION: n is a, c, g, t or u
```

<400> SEQUENCE: 71
uuuuuacact ctttccctac acgacgctct tccgatctac ctgattgctg tataactttt     60
tttttttttt tttttvn                                                   78

<210> SEQ ID NO 72
<211> LENGTH: 78
<212> TYPE: DNA
<213> ORGANISM: Artificial sequence
<220> FEATURE:
<223> OTHER INFORMATION: synthesized Probe 23
<220> FEATURE:
<221> NAME/KEY: misc_feature
<222> LOCATION: (78)..(78)
<223> OTHER INFORMATION: n is a, c, g, t or u

<400> SEQUENCE: 72
uuuuuacact ctttccctac acgacgctct tccgatctca gcgcatctat cctctatttt     60
tttttttttt tttttvn                                                   78

<210> SEQ ID NO 73
<211> LENGTH: 78
<212> TYPE: DNA
<213> ORGANISM: Artificial sequence
<220> FEATURE:
<223> OTHER INFORMATION: synthesized Probe 24
<220> FEATURE:
<221> NAME/KEY: misc_feature
<222> LOCATION: (78)..(78)
<223> OTHER INFORMATION: n is a, c, g, t or u

<400> SEQUENCE: 73
uuuuuacact ctttccctac acgacgctct tccgatcttc cacgcgtagg actagttttt     60
tttttttttt tttttvn                                                   78

<210> SEQ ID NO 74
<211> LENGTH: 78
<212> TYPE: DNA
<213> ORGANISM: Artificial sequence
<220> FEATURE:
<223> OTHER INFORMATION: synthesized Probe 25
<220> FEATURE:
<221> NAME/KEY: misc_feature
<222> LOCATION: (78)..(78)
<223> OTHER INFORMATION: n is a, c, g, t or u

<400> SEQUENCE: 74
uuuuuacact ctttccctac acgacgctct tccgatctcg actaagtatg tagcgctttt     60
tttttttttt tttttvn                                                   78

<210> SEQ ID NO 75
<211> LENGTH: 30
<212> TYPE: DNA
<213> ORGANISM: Artificial sequence
<220> FEATURE:
<223> OTHER INFORMATION: synthesized Frame probe - Layout 1

<400> SEQUENCE: 75
aaatttcgtc tgctatcgcg cttctgtacc                                     30

<210> SEQ ID NO 76
<211> LENGTH: 21
<212> TYPE: DNA
<213> ORGANISM: Artificial sequence
<220> FEATURE:

<223> OTHER INFORMATION: synthesized Fluorescent marker probe PS 1
<220> FEATURE:
<221> NAME/KEY: misc_feature
<222> LOCATION: (21)..(21)
<223> OTHER INFORMATION: Coupled to cyanine 3 fluorescent dye

<400> SEQUENCE: 76
ggtacagaag cgcgatagca g                                          21

<210> SEQ ID NO 77
<211> LENGTH: 33
<212> TYPE: DNA
<213> ORGANISM: Artificial sequence
<220> FEATURE:
<223> OTHER INFORMATION: synthesized Second strand synthesis and first
      PCR amplification handle - A primer

<400> SEQUENCE: 77
acactctttc cctacacgac gctcttccga tct                             33

<210> SEQ ID NO 78
<211> LENGTH: 43
<212> TYPE: DNA
<213> ORGANISM: Artificial sequence
<220> FEATURE:
<223> OTHER INFORMATION: synthesized Second strand synthesis and first
      PCR amplification handle - B dt20VN primer
<220> FEATURE:
<221> NAME/KEY: misc_feature
<222> LOCATION: (43)..(43)
<223> OTHER INFORMATION: n is a, c, g, or t

<400> SEQUENCE: 78
agacgtgtgc tcttccgatc tttttttttt tttttttttt tvn                  43

<210> SEQ ID NO 79
<211> LENGTH: 43
<212> TYPE: DNA
<213> ORGANISM: Artificial sequence
<220> FEATURE:
<223> OTHER INFORMATION: synthesized Custom sequencing primer B r2

<400> SEQUENCE: 79
tcagacgtgt gctcttccga tcttttttttt tttttttttt ttt                 43

<210> SEQ ID NO 80
<211> LENGTH: 66
<212> TYPE: DNA
<213> ORGANISM: Artificial sequence
<220> FEATURE:
<223> OTHER INFORMATION: synthesized Probe 1

<400> SEQUENCE: 80
gcgttcagag tggcagtcga gatcacgcgg caatcatatc ggacagatcg gaagagcgta    60
gtgtag                                                               66

<210> SEQ ID NO 81
<211> LENGTH: 66
<212> TYPE: DNA
<213> ORGANISM: Artificial sequence
<220> FEATURE:
<223> OTHER INFORMATION: synthesized Probe 2

<400> SEQUENCE: 81
gcgttcagag tggcagtcga gatcacaaga tgaacccggc tcatagatcg gaagagcgta    60
gtgtag                                                               66

<210> SEQ ID NO 82
<211> LENGTH: 66
<212> TYPE: DNA
<213> ORGANISM: Artificial sequence
<220> FEATURE:
<223> OTHER INFORMATION: synthesized Probe 3

<400> SEQUENCE: 82
gcgttcagag tggcagtcga gatcactccc aacagagtgc ctcaagatcg gaagagcgta      60
gtgtag      66

<210> SEQ ID NO 83
<211> LENGTH: 66
<212> TYPE: DNA
<213> ORGANISM: Artificial sequence
<220> FEATURE:
<223> OTHER INFORMATION: synthesized Probe 4

<400> SEQUENCE: 83
gcgttcagag tggcagtcga gatcaccgaa tggcgactaa tcatagatcg gaagagcgta      60
gtgtag      66

<210> SEQ ID NO 84
<211> LENGTH: 66
<212> TYPE: DNA
<213> ORGANISM: Artificial sequence
<220> FEATURE:
<223> OTHER INFORMATION: synthesized Probe 5

<400> SEQUENCE: 84
gcgttcagag tggcagtcga gatcacaaac atctaccctc aagtagatcg gaagagcgta      60
gtgtag      66

<210> SEQ ID NO 85
<211> LENGTH: 66
<212> TYPE: DNA
<213> ORGANISM: Artificial sequence
<220> FEATURE:
<223> OTHER INFORMATION: synthesized Probe 6

<400> SEQUENCE: 85
gcgttcagag tggcagtcga gatcacgata acagtattgg ccatagatcg gaagagcgta      60
gtgtag      66

<210> SEQ ID NO 86
<211> LENGTH: 66
<212> TYPE: DNA
<213> ORGANISM: Artificial sequence
<220> FEATURE:
<223> OTHER INFORMATION: synthesized Probe 7

<400> SEQUENCE: 86
gcgttcagag tggcagtcga gatcacggtc gaatcagggt agcgagatcg gaagagcgta      60
gtgtag      66

<210> SEQ ID NO 87
<211> LENGTH: 66
<212> TYPE: DNA
<213> ORGANISM: Artificial sequence
<220> FEATURE:
<223> OTHER INFORMATION: synthesized Probe 8

```
<400> SEQUENCE: 87
gcgttcagag tggcagtcga gatcacacta cggcgaaagt gggcagatcg gaagagcgta    60
gtgtag                                                              66

<210> SEQ ID NO 88
<211> LENGTH: 66
<212> TYPE: DNA
<213> ORGANISM: Artificial sequence
<220> FEATURE:
<223> OTHER INFORMATION: synthesized Probe 9

<400> SEQUENCE: 88
gcgttcagag tggcagtcga gatcacatct tgctcaaagt tgctagatcg gaagagcgta    60
gtgtag                                                              66

<210> SEQ ID NO 89
<211> LENGTH: 66
<212> TYPE: DNA
<213> ORGANISM: Artificial sequence
<220> FEATURE:
<223> OTHER INFORMATION: synthesized Probe 10

<400> SEQUENCE: 89
gcgttcagag tggcagtcga gatcacccgg aattccgaat tggcagatcg gaagagcgta    60
gtgtag                                                              66

<210> SEQ ID NO 90
<211> LENGTH: 66
<212> TYPE: DNA
<213> ORGANISM: Artificial sequence
<220> FEATURE:
<223> OTHER INFORMATION: synthesized Probe 11

<400> SEQUENCE: 90
gcgttcagag tggcagtcga gatcacatgt attaccttgg gcgaagatcg gaagagcgta    60
gtgtag                                                              66

<210> SEQ ID NO 91
<211> LENGTH: 66
<212> TYPE: DNA
<213> ORGANISM: Artificial sequence
<220> FEATURE:
<223> OTHER INFORMATION: synthesized Probe 12

<400> SEQUENCE: 91
gcgttcagag tggcagtcga gatcacctcg aataggaaat gcgaagatcg gaagagcgta    60
gtgtag                                                              66

<210> SEQ ID NO 92
<211> LENGTH: 66
<212> TYPE: DNA
<213> ORGANISM: Artificial sequence
<220> FEATURE:
<223> OTHER INFORMATION: synthesized Probe 13

<400> SEQUENCE: 92
gcgttcagag tggcagtcga gatcacggcg gttagattta gcaaagatcg gaagagcgta    60
gtgtag                                                              66

<210> SEQ ID NO 93
<211> LENGTH: 66
```

```
<212> TYPE: DNA
<213> ORGANISM: Artificial sequence
<220> FEATURE:
<223> OTHER INFORMATION: synthesized Probe 14

<400> SEQUENCE: 93
gcgttcagag tggcagtcga gatcacccat cagaatttaa ttccagatcg gaagagcgta    60
gtgtag                                                                66

<210> SEQ ID NO 94
<211> LENGTH: 66
<212> TYPE: DNA
<213> ORGANISM: Artificial sequence
<220> FEATURE:
<223> OTHER INFORMATION: synthesized Probe 15

<400> SEQUENCE: 94
gcgttcagag tggcagtcga gatcacctta gcacctatgt aatgagatcg gaagagcgta    60
gtgtag                                                                66

<210> SEQ ID NO 95
<211> LENGTH: 66
<212> TYPE: DNA
<213> ORGANISM: Artificial sequence
<220> FEATURE:
<223> OTHER INFORMATION: synthesized Probe 16

<400> SEQUENCE: 95
gcgttcagag tggcagtcga gatcacgtgc gagcgcaagt caatagatcg gaagagcgta    60
gtgtag                                                                66

<210> SEQ ID NO 96
<211> LENGTH: 66
<212> TYPE: DNA
<213> ORGANISM: Artificial sequence
<220> FEATURE:
<223> OTHER INFORMATION: synthesized Probe 17

<400> SEQUENCE: 96
gcgttcagag tggcagtcga gatcacgaac ttgggagata ctatagatcg gaagagcgta    60
gtgtag                                                                66

<210> SEQ ID NO 97
<211> LENGTH: 66
<212> TYPE: DNA
<213> ORGANISM: Artificial sequence
<220> FEATURE:
<223> OTHER INFORMATION: synthesized Probe 18

<400> SEQUENCE: 97
gcgttcagag tggcagtcga gatcactgcg gattacaggc gcacagatcg gaagagcgta    60
gtgtag                                                                66

<210> SEQ ID NO 98
<211> LENGTH: 66
<212> TYPE: DNA
<213> ORGANISM: Artificial sequence
<220> FEATURE:
<223> OTHER INFORMATION: synthesized Probe 19

<400> SEQUENCE: 98
gcgttcagag tggcagtcga gatcacctac ctaaagagtg gcgcagatcg gaagagcgta    60
```

```
gtgtag                                                          66

<210> SEQ ID NO 99
<211> LENGTH: 66
<212> TYPE: DNA
<213> ORGANISM: Artificial sequence
<220> FEATURE:
<223> OTHER INFORMATION: synthesized Probe 20

<400> SEQUENCE: 99
gcgttcagag tggcagtcga gatcacaagc caatcacttg cataagatcg gaagagcgta    60
gtgtag                                                          66

<210> SEQ ID NO 100
<211> LENGTH: 66
<212> TYPE: DNA
<213> ORGANISM: Artificial sequence
<220> FEATURE:
<223> OTHER INFORMATION: synthesized Probe 21

<400> SEQUENCE: 100
gcgttcagag tggcagtcga gatcaccgta taaacgtggc ttggagatcg gaagagcgta    60
gtgtag                                                          66

<210> SEQ ID NO 101
<211> LENGTH: 66
<212> TYPE: DNA
<213> ORGANISM: Artificial sequence
<220> FEATURE:
<223> OTHER INFORMATION: synthesized Probe 22

<400> SEQUENCE: 101
gcgttcagag tggcagtcga gatcacgtta tacagcaatc aggtagatcg gaagagcgta    60
gtgtag                                                          66

<210> SEQ ID NO 102
<211> LENGTH: 66
<212> TYPE: DNA
<213> ORGANISM: Artificial sequence
<220> FEATURE:
<223> OTHER INFORMATION: synthesized Probe 23

<400> SEQUENCE: 102
gcgttcagag tggcagtcga gatcactaga ggatagatgc gctgagatcg gaagagcgta    60
gtgtag                                                          66

<210> SEQ ID NO 103
<211> LENGTH: 66
<212> TYPE: DNA
<213> ORGANISM: Artificial sequence
<220> FEATURE:
<223> OTHER INFORMATION: synthesized Probe 24

<400> SEQUENCE: 103
gcgttcagag tggcagtcga gatcacacta gtcctacgcg tggaagatcg gaagagcgta    60
gtgtag                                                          66

<210> SEQ ID NO 104
<211> LENGTH: 66
<212> TYPE: DNA
<213> ORGANISM: Artificial sequence
<220> FEATURE:
<223> OTHER INFORMATION: synthesized Probe 25
```

<400> SEQUENCE: 104
gcgttcagag tggcagtcga gatcacgcgc tacatactta gtcgagatcg aagagcgta    60 gtgtag    66

<210> SEQ ID NO 105
<211> LENGTH: 30
<212> TYPE: DNA
<213> ORGANISM: Artificial sequence
<220> FEATURE:
<223> OTHER INFORMATION: synthesized Frame probe - layout 1

<400> SEQUENCE: 105
aaatttcgtc tgctatcgcg cttctgtacc    30

<210> SEQ ID NO 106
<211> LENGTH: 45
<212> TYPE: DNA
<213> ORGANISM: Artificial sequence
<220> FEATURE:
<223> OTHER INFORMATION: synthesized Capture probe - LP poly-dTVN
<220> FEATURE:
<221> NAME/KEY: misc_feature
<222> LOCATION: (45)..(45)
<223> OTHER INFORMATION: n is a, c, g, or t

<400> SEQUENCE: 106
gtgatctcga ctgccactct gaatttttttt tttttttttt tttvn    45

<210> SEQ ID NO 107
<211> LENGTH: 33
<212> TYPE: DNA
<213> ORGANISM: Artificial sequence
<220> FEATURE:
<223> OTHER INFORMATION: synthesized Amplification handle probe A-handle

<400> SEQUENCE: 107
acactctttc cctacacgac gctcttccga tct    33

<210> SEQ ID NO 108
<211> LENGTH: 33
<212> TYPE: DNA
<213> ORGANISM: Artificial sequence
<220> FEATURE:
<223> OTHER INFORMATION: synthesized Second strand synthesis and first
     PCR amplification handle - A primer

<400> SEQUENCE: 108
acactctttc cctacacgac gctcttccga tct    33

<210> SEQ ID NO 109
<211> LENGTH: 43
<212> TYPE: DNA
<213> ORGANISM: Artificial sequence
<220> FEATURE:
<223> OTHER INFORMATION: synthesized Second strand synthesis and first
     PCR amplification handle - B dt20VN primer
<220> FEATURE:
<221> NAME/KEY: misc_feature
<222> LOCATION: (43)..(43)
<223> OTHER INFORMATION: n is a, c, g, or t

<400> SEQUENCE: 109
agacgtgtgc tcttccgatc tttttttttt tttttttttt tvn    43

<210> SEQ ID NO 110

<211> LENGTH: 33
<212> TYPE: DNA
<213> ORGANISM: Artificial sequence
<220> FEATURE:
<223> OTHER INFORMATION: synthesized Second PCR - A primer

<400> SEQUENCE: 110
acactctttc cctacacgac gctcttccga tct                          33

<210> SEQ ID NO 111
<211> LENGTH: 34
<212> TYPE: DNA
<213> ORGANISM: Artificial sequence
<220> FEATURE:
<223> OTHER INFORMATION: synthesized Second PCR - B primer

<400> SEQUENCE: 111
gtgactggag ttcagacgtg tgctcttccg atct                         34

<210> SEQ ID NO 112
<211> LENGTH: 39
<212> TYPE: DNA
<213> ORGANISM: Artificial sequence
<220> FEATURE:
<223> OTHER INFORMATION: synthesized Template Switching primer - longB
<220> FEATURE:
<221> NAME/KEY: misc_feature
<222> LOCATION: (37)..(39)
<223> OTHER INFORMATION: Ribonucleotides

<400> SEQUENCE: 112
gtgactggag ttcagacgtg tgctcttccg atctatggg                    39

<210> SEQ ID NO 113
<211> LENGTH: 78
<212> TYPE: DNA
<213> ORGANISM: Artificial sequence
<220> FEATURE:
<223> OTHER INFORMATION: synthesized Probe 1
<220> FEATURE:
<221> NAME/KEY: misc_feature
<222> LOCATION: (78)..(78)
<223> OTHER INFORMATION: n is a, c, g, t or u

<400> SEQUENCE: 113
uuuuuacact ctttccctac acgacgctct tccgatctgt ccgatatgat tgccgctttt     60
tttttttttt tttttvn                                                   78

<210> SEQ ID NO 114
<211> LENGTH: 78
<212> TYPE: DNA
<213> ORGANISM: Artificial Sequence
<220> FEATURE:
<223> OTHER INFORMATION: synthesized Probe 2
<220> FEATURE:
<221> NAME/KEY: misc_feature
<222> LOCATION: (78)..(78)
<223> OTHER INFORMATION: n is a, c, g, t or u

<400> SEQUENCE: 114
uuuuuacact ctttccctac acgacgctct tccgatctat gagccgggtt catcttttt      60 tttttttttt tttttvn                                                   78

<210> SEQ ID NO 115
<211> LENGTH: 78
<212> TYPE: DNA
<213> ORGANISM: Artificial sequence -continued
<220> FEATURE:
<223> OTHER INFORMATION: synthesized Probe 3
<220> FEATURE:
<221> NAME/KEY: misc_feature
<222> LOCATION: (78)..(78)
<223> OTHER INFORMATION: n is a, c, g, t or u

<400> SEQUENCE: 115
uuuuuacact ctttccctac acgacgctct tccgatcttg aggcactctg ttgggatttt    60
tttttttttt tttttttvn                                                 78

<210> SEQ ID NO 116
<211> LENGTH: 78
<212> TYPE: DNA
<213> ORGANISM: Artificial sequence
<220> FEATURE:
<223> OTHER INFORMATION: synthesized Probe 4
<220> FEATURE:
<221> NAME/KEY: misc_feature
<222> LOCATION: (78)..(78)
<223> OTHER INFORMATION: n is a, c, g, t or u

<400> SEQUENCE: 116
uuuuuacact ctttccctac acgacgctct tccgatctat gattagtcgc cattcgtttt    60
tttttttttt tttttttvn                                                 78

<210> SEQ ID NO 117
<211> LENGTH: 78
<212> TYPE: DNA
<213> ORGANISM: Artificial sequence
<220> FEATURE:
<223> OTHER INFORMATION: synthesized Probe 5
<220> FEATURE:
<221> NAME/KEY: misc_feature
<222> LOCATION: (78)..(78)
<223> OTHER INFORMATION: n is a, c, g, t or u

<400> SEQUENCE: 117
uuuuuacact ctttccctac acgacgctct tccgatctac ttgagggtag atgttttttt    60
tttttttttt tttttttvn                                                 78

<210> SEQ ID NO 118
<211> LENGTH: 78
<212> TYPE: DNA
<213> ORGANISM: Artificial sequence
<220> FEATURE:
<223> OTHER INFORMATION: synthesized Probe 6
<220> FEATURE:
<221> NAME/KEY: misc_feature
<222> LOCATION: (78)..(78)
<223> OTHER INFORMATION: n is a, c, g, t or u

<400> SEQUENCE: 118
uuuuuacact ctttccctac acgacgctct tccgatctat ggccaatact gttatctttt    60
tttttttttt tttttttvn                                                 78

<210> SEQ ID NO 119
<211> LENGTH: 78
<212> TYPE: DNA
<213> ORGANISM: Artificial sequence
<220> FEATURE:
<223> OTHER INFORMATION: synthesized Probe 7
<220> FEATURE:
<221> NAME/KEY: misc_feature
<222> LOCATION: (78)..(78)
<223> OTHER INFORMATION: n is a, c, g, t or u

```
<400> SEQUENCE: 119
uuuuuacact ctttccctac acgacgctct tccgatctcg ctaccctgat tcgaccttttt    60 tttttttttt tttttttvn                                                 78

<210> SEQ ID NO 120
<211> LENGTH: 78
<212> TYPE: DNA
<213> ORGANISM: Artificial sequence
<220> FEATURE:
<223> OTHER INFORMATION: synthesized Probe 8
<220> FEATURE:
<221> NAME/KEY: misc_feature
<222> LOCATION: (78)..(78)
<223> OTHER INFORMATION: n is a, c, g, t or u

<400> SEQUENCE: 120
uuuuuacact ctttccctac acgacgctct tccgatctgc ccactttcgc cgtagttttt    60
tttttttttt tttttvn                                                   78

<210> SEQ ID NO 121
<211> LENGTH: 78
<212> TYPE: DNA
<213> ORGANISM: Artificial sequence
<220> FEATURE:
<223> OTHER INFORMATION: synthesized Probe 9
<220> FEATURE:
<221> NAME/KEY: misc_feature
<222> LOCATION: (78)..(78)
<223> OTHER INFORMATION: n is a, c, g, t or u

<400> SEQUENCE: 121
uuuuuacact ctttccctac acgacgctct tccgatctag caactttgag caagatttttt    60 tttttttttt tttttvn                                                   78

<210> SEQ ID NO 122
<211> LENGTH: 78
<212> TYPE: DNA
<213> ORGANISM: Artificial sequence
<220> FEATURE:
<223> OTHER INFORMATION: synthesized Probe 10
<220> FEATURE:
<221> NAME/KEY: misc_feature
<222> LOCATION: (78)..(78)
<223> OTHER INFORMATION: n is a, c, g, t or u

<400> SEQUENCE: 122
uuuuuacact ctttccctac acgacgctct tccgatctgc caattcggaa ttccggttttt    60 tttttttttt tttttvn                                                   78

<210> SEQ ID NO 123
<211> LENGTH: 78
<212> TYPE: DNA
<213> ORGANISM: Artificial sequence
<220> FEATURE:
<223> OTHER INFORMATION: synthesized Probe 11
<220> FEATURE:
<221> NAME/KEY: misc_feature
<222> LOCATION: (78)..(78)
<223> OTHER INFORMATION: n is a, c, g, t or u

<400> SEQUENCE: 123
uuuuuacact ctttccctac acgacgctct tccgatcttc gcccaaggta atacattttt    60
tttttttttt tttttvn                                                   78
```

```
<210> SEQ ID NO 124
<211> LENGTH: 78
<212> TYPE: DNA
<213> ORGANISM: Artificial sequence
<220> FEATURE:
<223> OTHER INFORMATION: synthesized Probe 12
<220> FEATURE:
<221> NAME/KEY: misc_feature
<222> LOCATION: (78)..(78)
<223> OTHER INFORMATION: n is a, c, g, t or u

<400> SEQUENCE: 124
uuuuuacact ctttccctac acgacgctct tccgatcttc gcatttccta ttcgagtttt    60
tttttttttt tttttttvn                                                 78

<210> SEQ ID NO 125
<211> LENGTH: 78
<212> TYPE: DNA
<213> ORGANISM: Artificial sequence
<220> FEATURE:
<223> OTHER INFORMATION: synthesized Probe 13
<220> FEATURE:
<221> NAME/KEY: misc_feature
<222> LOCATION: (78)..(78)
<223> OTHER INFORMATION: n is a, c, g, t or u

<400> SEQUENCE: 125
uuuuuacact ctttccctac acgacgctct tccgatcttt gctaaatcta accgcctttt    60
tttttttttt tttttttvn                                                 78

<210> SEQ ID NO 126
<211> LENGTH: 78
<212> TYPE: DNA
<213> ORGANISM: Artificial sequence
<220> FEATURE:
<223> OTHER INFORMATION: synthesized Probe 14
<220> FEATURE:
<221> NAME/KEY: misc_feature
<222> LOCATION: (78)..(78)
<223> OTHER INFORMATION: n is a, c, g, t or u

<400> SEQUENCE: 126
uuuuuacact ctttccctac acgacgctct tccgatctgg aattaaattc tgatggtttt    60
tttttttttt tttttttvn                                                 78

<210> SEQ ID NO 127
<211> LENGTH: 78
<212> TYPE: DNA
<213> ORGANISM: Artificial sequence
<220> FEATURE:
<223> OTHER INFORMATION: synthesized Probe 15
<220> FEATURE:
<221> NAME/KEY: misc_feature
<222> LOCATION: (78)..(78)
<223> OTHER INFORMATION: n is a, c, g, t or u

<400> SEQUENCE: 127
uuuuuacact ctttccctac acgacgctct tccgatctca ttacataggt gctaagtttt    60
tttttttttt tttttttvn                                                 78

<210> SEQ ID NO 128
<211> LENGTH: 78
<212> TYPE: DNA
<213> ORGANISM: Artificial sequence
<220> FEATURE:
<223> OTHER INFORMATION: synthesized Probe 16
<220> FEATURE:
```

```
<221> NAME/KEY: misc_feature
<222> LOCATION: (78)..(78)
<223> OTHER INFORMATION: n is a, c, g, t or u

<400> SEQUENCE: 128
uuuuuacact ctttccctac acgacgctct tccgatctat tgacttgcgc tcgcactttt    60
tttttttttt tttttttvn                                                 78

<210> SEQ ID NO 129
<211> LENGTH: 78
<212> TYPE: DNA
<213> ORGANISM: Artificial sequence
<220> FEATURE:
<223> OTHER INFORMATION: synthesized Probe 17
<220> FEATURE:
<221> NAME/KEY: misc_feature
<222> LOCATION: (78)..(78)
<223> OTHER INFORMATION: n is a, c, g, t or u

<400> SEQUENCE: 129
uuuuuacact ctttccctac acgacgctct tccgatctat agtatctccc aagttctttt    60
tttttttttt tttttttvn                                                 78

<210> SEQ ID NO 130
<211> LENGTH: 78
<212> TYPE: DNA
<213> ORGANISM: Artificial sequence
<220> FEATURE:
<223> OTHER INFORMATION: synthesized Probe 18
<220> FEATURE:
<221> NAME/KEY: misc_feature
<222> LOCATION: (78)..(78)
<223> OTHER INFORMATION: n is a, c, g, t or u

<400> SEQUENCE: 130
uuuuuacact ctttccctac acgacgctct tccgatctgt gcgcctgtaa tccgcatttt    60
tttttttttt tttttttvn                                                 78

<210> SEQ ID NO 131
<211> LENGTH: 78
<212> TYPE: DNA
<213> ORGANISM: Artificial sequence
<220> FEATURE:
<223> OTHER INFORMATION: synthesized Probe 19
<220> FEATURE:
<221> NAME/KEY: misc_feature
<222> LOCATION: (78)..(78)
<223> OTHER INFORMATION: n is a, c, g, t or u

<400> SEQUENCE: 131
uuuuuacact ctttccctac acgacgctct tccgatctgc gccactcttt aggtagtttt    60
tttttttttt tttttttvn                                                 78

<210> SEQ ID NO 132
<211> LENGTH: 78
<212> TYPE: DNA
<213> ORGANISM: Artificial sequence
<220> FEATURE:
<223> OTHER INFORMATION: synthesized Probe 20
<220> FEATURE:
<221> NAME/KEY: misc_feature
<222> LOCATION: (78)..(78)
<223> OTHER INFORMATION: n is a, c, g, t or u

<400> SEQUENCE: 132
uuuuuacact ctttccctac acgacgctct tccgatctta tgcaagtgat tggctttttt    60
```
tttttttttt tttttvn    78

<210> SEQ ID NO 133
<211> LENGTH: 78
<212> TYPE: DNA
<213> ORGANISM: Artificial sequence
<220> FEATURE:
<223> OTHER INFORMATION: synthesized Probe 21
<220> FEATURE:
<221> NAME/KEY: misc_feature
<222> LOCATION: (78)..(78)
<223> OTHER INFORMATION: n is a, c, g, t or u

<400> SEQUENCE: 133
uuuuuacact ctttccctac acgacgctct tccgatctcc aagccacgtt tatacgtttt    60
tttttttttt tttttvn    78

<210> SEQ ID NO 134
<211> LENGTH: 78
<212> TYPE: DNA
<213> ORGANISM: Artificial sequence
<220> FEATURE:
<223> OTHER INFORMATION: synthesized Probe 22
<220> FEATURE:
<221> NAME/KEY: misc_feature
<222> LOCATION: (78)..(78)
<223> OTHER INFORMATION: n is a, c, g, t or u

<400> SEQUENCE: 134
uuuuuacact ctttccctac acgacgctct tccgatctac ctgattgctg tataactttt    60
tttttttttt tttttvn    78

<210> SEQ ID NO 135
<211> LENGTH: 78
<212> TYPE: DNA
<213> ORGANISM: Artificial sequence
<220> FEATURE:
<223> OTHER INFORMATION: synthesized Probe 23
<220> FEATURE:
<221> NAME/KEY: misc_feature
<222> LOCATION: (78)..(78)
<223> OTHER INFORMATION: n is a, c, g, t or u

<400> SEQUENCE: 135
uuuuuacact ctttccctac acgacgctct tccgatctca gcgcatctat cctctatttt    60
tttttttttt tttttvn    78

<210> SEQ ID NO 136
<211> LENGTH: 78
<212> TYPE: DNA
<213> ORGANISM: Artificial sequence
<220> FEATURE:
<223> OTHER INFORMATION: synthesized Probe 24
<220> FEATURE:
<221> NAME/KEY: misc_feature
<222> LOCATION: (78)..(78)
<223> OTHER INFORMATION: n is a, c, g, t or u

<400> SEQUENCE: 136
uuuuuacact ctttccctac acgacgctct tccgatcttc cacgcgtagg actagtttt    60 tttttttttt tttttvn    78

<210> SEQ ID NO 137
<211> LENGTH: 78
<212> TYPE: DNA

```
<213> ORGANISM: Artificial sequence
<220> FEATURE:
<223> OTHER INFORMATION: synthesized Probe 25
<220> FEATURE:
<221> NAME/KEY: misc_feature
<222> LOCATION: (78)..(78)
<223> OTHER INFORMATION: n is a, c, g, t or u

<400> SEQUENCE: 137
uuuuuacact ctttccctac acgacgctct tccgatctcg actaagtatg tagcgctttt      60 ttttttttt tttttvn                                                      78

<210> SEQ ID NO 138
<211> LENGTH: 30
<212> TYPE: DNA
<213> ORGANISM: Artificial sequence
<220> FEATURE:
<223> OTHER INFORMATION: synthesized Frame probe

<400> SEQUENCE: 138
aaatttcgtc tgctatcgcg cttctgtacc                                       30

<210> SEQ ID NO 139
<211> LENGTH: 21
<212> TYPE: DNA
<213> ORGANISM: Artificial sequence
<220> FEATURE:
<223> OTHER INFORMATION: synthesized Fluorescent marker probe
<220> FEATURE:
<221> NAME/KEY: misc_feature
<222> LOCATION: (21)..(21)
<223> OTHER INFORMATION: Coupled to cyanine 3 fluorescent dye

<400> SEQUENCE: 139
ggtacagaag cgcgatagca g                                                21
```

METHODS AND PRODUCT FOR OPTIMISING LOCALISED OR SPATIAL DETECTION OF GENE EXPRESSION IN A TISSUE SAMPLE

CROSS-REFERENCE TO RELATED APPLICATIONS

This application is a 371 of PCT/EP2013/071645 filed Oct. 16, 2013, which claims the benefit of priority to Great Britain provisional application Nos. 1218654.0, filed on Oct. 17, 2012 and 1304585.1 filed on Mar. 14, 2013 under the provisions of 35 U.S.C. 119 and the International Convention for the protection of Industrial Property, which are incorporated herein by reference.

The present invention relates generally to the localised or spatial detection of nucleic acid in a tissue sample or a portion thereof. Particularly, the present invention provides methods for detecting and/or analysing RNA, e.g. RNA transcripts, so as to obtain spatial information about the localisation, distribution or expression of genes in a tissue sample, for example in an individual cell. The present invention thus enables spatial transcriptomics.

More particularly, the present invention relates to a method for localised or spatial detection of transcripts in a tissue sample or a portion thereof, e.g. for determining and/or analysing a transcriptome, and especially the global transcriptome, of a tissue sample or a portion thereof. In particular the method relates to a quantitative and/or qualitative method for analysing the distribution, location or expression of nucleic acid molecules in a tissue sample wherein the spatial expression or distribution or location pattern within the tissue sample is retained. Thus, the method provides a process for performing "spatial transcriptomics", which enables the user to determine simultaneously the expression pattern, or the location/distribution pattern of the genes expressed, present in a tissue sample or a portion thereof. The present invention also provides methods for determining the optimum conditions for localized or spatial detection of (e.g. for capturing) nucleic acids from a tissue sample on a substrate, thereby allowing the maximum amount of nucleic acid molecules to be captured, whilst retaining the distribution or location pattern that originated within the tissue sample.

The invention is particularly based on array technology and may be coupled with high throughput DNA sequencing technologies. The methods of the invention allow the nucleic acid molecules (e.g. RNA molecules) in the tissue sample, particularly mRNA, to be captured on an object substrate (e.g. a slide or chip, which may be an array) and labelled, which may include the incorporation of a positional tag. The labelled molecules may be visualised to determine or assess the efficacy of the conditions used to capture the nucleic acid molecules. Alternatively or additionally, the captured nucleic acid molecules (or a subset thereof, e.g. a portion of the nucleic acid molecules captured from the tissue sample) may be analysed further, e.g. by sequence analysis. For instance, the captured nucleic acid molecules may be used to template the synthesis of DNA molecules which are sequenced and analysed to determine which genes are expressed in all or one or more parts of the tissue sample. Advantageously, the individual, separate and specific transcriptome of each cell in the tissue sample may be obtained at the same time. Hence, the methods of the invention may be said to provide highly parallel comprehensive transcriptome signatures from individual cells (or groups of cells) within a tissue sample, or a portion thereof, without losing spatial information within said investigated tissue sample. The invention also provides an object substrate, such as a chip or slide (e.g. an array) for performing the method of the invention and methods for making the object substrate e.g. chip or slide, of the invention.

The human body comprises over 100 trillion cells and is organized into more than 250 different organs and tissues. The development and organization of complex organs, such as the brain, are far from understood and there is a need to dissect the expression of genes expressed in such tissues using quantitative methods to investigate and determine the genes that control the development and function of such tissues. The organs are in themselves a mixture of differentiated cells that enable all bodily functions, such as nutrient transport, defense etc. to be coordinated and maintained. Consequently, cell function is dependent on the position of the cell within a particular tissue structure and the interactions it shares with other cells within that tissue, both directly and indirectly. Hence, there is a need to disentangle how these interactions influence each cell within a tissue at the transcriptional level.

Recent findings by deep RNA sequencing have demonstrated that a majority of the transcripts can be detected in a human cell line and that a large fraction (75%) of the human protein-coding genes are expressed in most tissues. Similarly, a detailed study of 1% of the human genome showed that chromosomes are ubiquitously transcribed and that the majority of all bases are included in primary transcripts. The transcription machinery can therefore be described as promiscuous at a global level.

It is well-known that transcripts are merely a proxy for protein abundance, because the rates of RNA translation, degradation etc will influence the amount of protein produced from any one transcript. In this respect, a recent antibody-based analysis of human organs and tissues suggests that tissue specificity is achieved by precise regulation of protein levels in space and time, and that different tissues in the body acquire their unique characteristics by controlling not which proteins are expressed but how much of each is produced.

However, in subsequent global studies transcriptome and proteome correlations have been compared demonstrating that the majority of all genes were shown to be expressed. Interestingly, there was shown to be a high correlation between changes in RNA and protein levels for individual gene products which is indicative of the biological usefulness of studying the transcriptome in individual cells in the context of the functional role of proteins.

Indeed, analysis of the histology and expression pattern in tissues is a cornerstone in biomedical research and diagnostics. Histology, utilizing different staining techniques, first established the basic structural organization of healthy organs and the changes that take place in common pathologies more than a century ago. Developments in this field resulted in the possibility of studying protein distribution by immunohistochemistry and gene expression by in situ hybridization.

However, the parallel development of increasingly advanced histological and gene expression techniques has resulted in the separation of imaging and transcriptome analysis and, until the methods of the present invention, there has not been any feasible method available for global transcriptome analysis with spatial resolution.

As an alternative, or in addition, to in situ techniques, methods have developed for the in vitro analysis of proteins and nucleic acids, i.e. by extracting molecules from whole tissue samples, single cell types, or even single cells, and quantifying specific molecules in said extracts, e.g. by ELISA, qPCR etc.

Recent developments in the analysis of gene expression have resulted in the possibility of assessing the complete transcriptome of tissues using microarrays or RNA sequencing, and such developments have been instrumental in our understanding of biological processes and for diagnostics. However, transcriptome analysis typically is performed on mRNA extracted from whole tissues (or even whole organisms), and methods for collecting smaller tissue areas or individual cells for transcriptome analysis are typically labour intensive, costly and have low precision.

Hence, the majority of gene expression studies based on microarrays or next generation sequencing of RNA use a representative sample containing many cells. Thus the results represent the average expression levels of the investigated genes. The separation of cells that are phenotypically different has been used in some cases together with the global gene expression platforms (Tang F et al, Nat Protoc. 2010; 5: 516-35; Wang D & Bodovitz S, Trends Biotechnol. 2010; 28:281-90) and resulted in very precise information about cell-to-cell variations. However, high throughput methods to study transcriptional activity with high resolution in intact tissues have not, until now, been available.

Thus, existing techniques for the analysis of gene expression patterns provide spatial transcriptional information only for one or a handful of genes at a time or offer transcriptional information for all of the genes in a sample at the cost of losing positional information. Hence, it is evident that methods to determine simultaneously, separately and specifically the transcriptome of each cell in a sample are required, i.e. to enable global gene expression analysis in tissue samples that yields transcriptomic information with spatial resolution, and the present invention addresses this need. The present invention may also be seen to provide alternative methods for the analysis of gene expression patterns that provide spatial transcriptional information for one or a handful of genes.

The novel approach of the methods and products of the present invention utilizes now conventional array technology and may utilise well established sequencing technology, which may yield transcriptional information for all of the genes in a sample, whilst retaining positional information for the transcripts. It will be evident to the person of skill in the art that this represents a milestone in the life sciences. The new technology opens a new field of so-called "spatial transcriptomics", which is likely to have profound consequences for our understanding of tissue development and tissue and cellular function in all multicellular organisms. It will be apparent that such techniques will be particularly useful in our understanding of the cause and progress of disease states and in developing effective treatments for such diseases, e.g. cancer. The methods of the invention will also find uses in the diagnosis of numerous medical conditions.

Array technology, particularly microarrays, arose from research at Stanford University where small amounts of DNA oligonucleotides were successfully attached to a glass surface in an ordered arrangement, a so-called "array", and used it to monitor the transcription of 45 genes (Schena M et al, Science. 1995; 270: 368-9, 371).

Since then, researchers around the world have published more than 30,000 papers using microarray technology. Multiple types of microarray have been developed for various applications, e.g. to detect single nucleotide polymorphisms (SNPs) or to genotype or re-sequence mutant genomes, and an important use of microarray technology has been for the investigation of gene expression. Indeed, the gene expression microarray was created as a means to analyze the level of expressed genetic material in a particular sample, with the real gain being the possibility to compare expression levels of many genes simultaneously. Several commercial microarray platforms are available for these types of experiments but it has also been possible to create custom made gene expression arrays.

Whilst the use of microarrays in gene expression studies is now commonplace, it is evident that new and more comprehensive so-called "next-generation DNA sequencing" (NGS) technologies are starting to replace DNA microarrays for many applications, e.g. in-depth transcriptome analysis.

The development of NGS technologies for ultra-fast genome sequencing represents a milestone in the life sciences (Petterson E et al, Genomics. 2009; 93: 105-11). These new technologies have dramatically decreased the cost of DNA sequencing and enabled the determination of the genome of higher organisms at an unprecedented rate, including those of specific individuals (Wade C M et al Science. 2009; 326: 865-7; Rubin J et al, Nature 2010; 464: 587-91). The new advances in high-throughput genomics have reshaped the biological research landscape and in addition to complete characterization of genomes it is possible also to study the full transcriptome in a digital and quantitative fashion. The bioinformatics tools to visualize and integrate these comprehensive sets of data have also been significantly improved during recent years.

However, it has surprisingly been found that a unique combination of histological and microarray techniques, which may also be coupled with NGS techniques, can yield comprehensive transcriptional information from multiple cells in a tissue sample which information is characterised by a two-dimensional spatial resolution. Thus, at one extreme the methods of the present invention can be used to analyse the expression of a single gene in a single cell in a sample, whilst retaining the cell within its context in the tissue sample. At the other extreme, and in a preferred aspect of the invention, the methods can be used to determine the expression of every gene in each and every cell, or substantially all cells, in a tissue sample (or portion thereof) simultaneously, i.e. the global spatial expression pattern of a tissue sample or portion thereof. It will be apparent that the methods of the invention also enable intermediate analyses to be performed. For instance, the methods may be used to determine or quantify the transcriptional activity of cells in a tissue sample (e.g. the relative abundance of transcripts in different cell or tissue types), which would allow transcriptome analysis to focus on specific regions of a tissue sample, e.g. regions or portions of tissues samples with high (or low) transcriptional activity.

It will be evident that the efficacy of the step of capturing nucleic acid molecules from tissue samples may be dependent on the source of the tissue and/or the methods used to prepare the tissue sample. Accordingly, the methods and arrays of the invention may be used to determine the optimum conditions to capture the nucleic acid molecules from a tissue sample on an object substrate, e.g. an array.

In its simplest form, the invention may be illustrated by the following summary. The invention requires reverse transcription (RT) primers to be immobilised on an object substrate, e.g. a glass slide or chip. Thin tissue sections are placed onto the substrate and a reverse transcription reaction is performed in the tissue section on the substrate. The RT primers, to which the RNA in the tissue sample binds (or hybridizes), are extended using the bound RNA as a template to obtain cDNA, which is therefore bound to the surface of the substrate. The synthesized part of the cDNA is labelled, e.g. with a visibly detectable label, such as a fluorescently labelled nucleotide which may be incorporated into the synthesized cDNA molecules. A consequence of labelling the synthesized cDNA is that each cDNA strand provides a detectable signal that corresponds to the presence of a RNA molecule in the tissue section, and the location of the cDNA on the surface of the substrate corresponds to its original location in the tissue section. The signal from the labelled cDNA is detected, e.g. the surface of the substrate is imaged, and accordingly, the relative abundance of transcript present in each part of the tissue section, e.g. each cell, can be detected and quantified. Optionally, the tissue section may be visualised or imaged, e.g. stained and photographed, before or after the cDNA synthesis step to enable the labelled cDNA molecule to be correlated with a position within the tissue sample.

Thus, in one aspect the method may be viewed as a method for capturing and/or labelling the transcriptome of a tissue sample on an object substrate and it will be evident from the discussion below that this method may find a variety of utilities, particularly in methods for detecting and/or analysing the transcriptome of a tissue sample or a portion thereof.

For instance, quantifying the relative abundance of the labelled cDNA may be used to determine the transcriptional activity of different regions of a tissue sample, e.g. to identify cells with high or no transcriptional activity. The method can be used to determine the optimum reaction conditions for detecting, e.g. capturing, the transcriptome of a tissue sample on an object substrate, e.g. by repeating the method using different conditions (e.g. conditions for permeabilizing the tissue to allow the nucleic acids in the tissue sample to interact with the immobilized primers on the substrate), comparing the intensity and/or resolution of the signal obtained from labelled cDNA molecules on the imaged substrates and optionally selecting the conditions that provide the optimum image intensity and/or resolution.

In some embodiments, the method may be viewed as a method for localized or spatial detection, e.g. quantification, of the relative abundance of one or more transcripts in a tissue sample, e.g. the RT primer may be specific for one or more transcripts thereby enabling a specific transcript (or set of transcripts) to be captured and labelled on the object surface, wherein subsequent detection, e.g. imaging, of the intensity and distribution of the signal from labelled transcript is representative of the amount of transcript (or set of transcripts) present in the tissue sample in specific locations.

In a related embodiment the method may be viewed as a method for localized or spatial detection and/or analysis of the transcriptome of one or more portions of a tissue sample, e.g. the RT primer may be capable of capturing all of the transcripts on the object surface, which are then labelled as described above. Subsequent detection, e.g. imaging, of the intensity and distribution of the signal from labelled transcriptome can be used to select one or more portions of the substrate for further analysis, e.g. sequence analysis. The labelled transcripts on portions of the substrate that are not selected for further analysis may be removed from the surface of the substrate, e.g. by laser ablation, and discarded. The remaining subset of labelled transcripts may be analysed, e.g. sequenced, and the sequence information may be correlated with the portion(s) of the substrate from which the labelled transcripts were not removed and that correspond(s) to a position in the tissue sample.

In yet another aspect of the invention the reverse transcription (RT) primers comprise also unique positional tags (domains) and the RT primers may be arrayed on the object substrate, e.g. a glass slide or chip, to generate an "array". The unique positional tags correspond to the location of the RT primers on the array (the features of the array). Thin tissue sections are placed onto the array and a reverse transcription reaction is performed in the tissue section on the substrate. The RT primers, to which the RNA in the tissue sample binds (or hybridizes), are extended using the bound RNA as a template to obtain cDNA, which is therefore bound to the surface of the array. The synthesized part of the cDNA is labelled, e.g. a detectable label, such as a fluorescently labelled nucleotide, may be incorporated into the synthesized cDNA. As consequence of the unique positional tags in the RT primers, each cDNA strand carries information about the position of the template RNA in the tissue section. The labelled cDNA is imaged, which enables the efficacy of the transcriptome capture step to be assessed. In some embodiments, the visualisation of the cDNA molecules also allows areas of the substrate to be targeted for removal of surface bound material, e.g. by laser ablation, such that only transcripts from portions of tissue sample that are of interest may be analysed further, as described above. The tissue section may be visualised or imaged, e.g. stained and photographed, before or after the cDNA synthesis step to enable the positional tag in the cDNA molecule to be correlated with a position within the tissue sample. The cDNA is sequenced, which results in a transcriptome with exact positional information. The sequence data can then be matched to a position in the tissue sample, which enables the visualization, e.g. using a computer, of the sequence data together with the tissue section, for instance to display the expression pattern of any gene of interest across the tissue. Similarly, it would be possible to mark different areas of the tissue section on the computer screen and obtain information on differentially expressed genes between any selected areas of interest. It will be evident that the methods of the invention may result in data that is in stark contrast to the data obtained using current methods to study mRNA populations. For example, methods based on in situ hybridization provide only relative information of single mRNA transcripts. Thus, the methods of the present invention have clear advantages over current in situ technologies. The global gene expression information obtainable from the methods of the invention also allows co-expression information and quantitative estimates of transcript abundance. It will be evident that this is a generally applicable strategy available for the analysis of any tissue in any species, e.g. animal, plant, fungus.

It will be seen from the above explanation that there is an immense value in coupling positional information to transcriptome information. For instance, it enables global gene expression mapping at high resolution, which will find utility in numerous applications, including e.g. cancer research and diagnostics.

Furthermore, it is evident that the methods described herein differ significantly from the previously described methods for analysis of the global transcriptome of a tissue sample and these differences result in numerous advantages. The present invention is predicated on the surprising discovery that the use of tissue sections does not interfere with synthesis of DNA (e.g. cDNA) primed by primers (e.g. reverse transcription primers) that are coupled to the surface of an object substrate, e.g. an array. Moreover, labelling the cDNA synthesized on the object substrate allows specific portions of a tissue sample to be selected for further analysis, which enables resources, e.g. sequencing resources, to be focussed on the analysis of specific cell or tissue types within a tissue sample. This may result in reduced costs and a less complex data set which may be analysed more efficiently and robustly than a data from the analysis of the transcriptome of the whole tissue sample.

Thus, in its first and broadest aspect, the present invention provides a method for localized or spatial detection and/or analysis of RNA, and particularly of transcripts, in a tissue sample or a portion thereof, comprising:

(a) providing an object substrate on which at least one species of capture probe is directly or indirectly immobilized such that the probes are oriented to have a free 3' end to enable said probe to function as a reverse transcriptase (RT) primer;

(b) contacting said substrate with a tissue sample and allowing RNA of the tissue sample to hybridise to the capture probes;

(c) generating cDNA molecules from the captured RNA molecules using said capture probes as RT primers;

(d) labelling the cDNA molecules generated in step (c), wherein said labelling step may be contemporaneous with, or subsequent to, said generating step, preferably wherein the label is incorporated into the synthesized part of the cDNA molecules;

(e) detecting a signal from the labelled cDNA molecules, e.g. imaging the substrate such that the signal from the labelled cDNA molecules is detected; and optionally (f) imaging the tissue sample, wherein the tissue sample is imaged before or after step (c).

The method may alternatively or additionally be viewed as a method for determining and/or analysing a transcriptome of a tissue sample or a portion thereof or a method for capturing and/or labelling the transcriptome of a tissue sample on an object substrate, e.g. an array.

Thus, in a second more particular aspect of the invention, the present invention can be seen to provide a method for determining the optimum conditions for localised or spatial detection of RNA (e.g. transcripts) in a tissue sample on an object substrate, comprising steps (a)-(e), and optionally step (f), described above on a first object substrate and further steps:

(g) repeating steps (a)-(e), and optionally step (f), with a second object substrate, using different conditions in step (b);

(h) comparing the intensity and/or resolution of the signal from the labelled cDNA molecules immobilized on said first and second object substrate; and optionally (i) selecting the conditions that provide the optimum signal intensity and/or resolution of the labelled cDNA molecules.

In a third aspect, the present invention can be seen to provide a method for determining and/or analysing RNA or a transcriptome of a tissue sample or a portion thereof comprising steps (a)-(e), and optionally step (f), described above and further steps:

(g') removing the labelled cDNA from at least one portion of the surface of the object substrate;

(h') optionally amplifying the remaining cDNA molecules immobilized on the surface of the object substrate;

(i') releasing at least part of the remaining cDNA molecules and/or optionally their amplicons from the surface of the object substrate, wherein said released molecules may be a first strand and/or second strand cDNA molecule or an amplicon thereof;

(j') directly or indirectly analysing the sequence of the released molecules.

It will be understood that this third aspect allows a part of the RNA or transcriptome to be determined and/or analysed, and in particular to be selectively analysed; by removing the labelled cDNA from at least a portion of the object substrate surface, it may be selected which of the cDNA (and hence which of the captured RNA) to be analysed. The removal step is discussed further below, but it will be understood that this could be achieved by removing a portion of the tissue sample from the substrate (which will concomitantly remove the labelled cDNA)

In a particularly preferred embodiment of the third aspect of the invention, the object substrate is an array and the capture probes each comprise a positional domain that corresponds to the position of each capture probe on the array. Accordingly, the method may be viewed as comprising:

(a") providing an object substrate (e.g. an array) on which multiple species of capture probes are directly or indirectly immobilized such that each species occupies a distinct position on the object substrate and is oriented to have a free 3' end to enable said probe to function as a reverse transcriptase (RT) primer, wherein each species of said capture probe comprises a nucleic acid molecule with 5' to 3':

(i) a positional domain that corresponds to the position of the capture probe on the object substrate, and (ii) a capture domain;

(b") contacting said object substrate with a tissue sample such that the position of a capture probe on the object substrate may be correlated with a position in the tissue sample and allowing RNA of the tissue sample to hybridise to the capture domain in said capture probes;

(c") generating cDNA molecules from the captured RNA molecules using said capture probes as RT primers, (d") labelling the cDNA molecules generated in step (c'), wherein said labelling step may be contemporaneous with, or subsequent to, said generating step, preferably wherein the label is incorporated into the synthesized part of the cDNA molecules;

(e") detecting a signal from the labelled cDNA molecules;

(f") optionally imaging the tissue sample, wherein the tissue sample is imaged before or after step (c").

(g") optionally removing the labelled cDNA from at least one portion of the surface of the object substrate;

(h") optionally amplifying the cDNA molecules immobilized on the surface of the object substrate;

(i") releasing at least part of the cDNA molecules and/or optionally their amplicons from the surface of the object substrate, wherein said released molecules may be a first strand and/or second strand cDNA molecule or an amplicon thereof and wherein said part includes the positional domain or a complement thereof;

(j") directly or indirectly analysing the sequence of the released molecules.

The methods allow the abundance of the transcripts from a tissue sample to visualised directly, e.g. by fluorescence, akin to a standard microarray. However, unlike a standard microarray, the abundance of the transcripts can be correlated directly with their position in the tissue sample. Advantageously, the detection of the labelled cDNA molecules in situ on the surface of the object substrate (i.e. such that their distribution the object substrate corresponds directly their distribution in the tissue sample) also allows for a portion or portions of the tissue sample of interest to be selected for analysis, thereby minimising the amount of data to be evaluated. Furthermore, the detection of the labelled cDNA molecules in situ on the surface of the object substrate enables the provision of a method for determining the optimum conditions for capturing the transcriptome of a tissue sample on an object substrate, wherein the spatial distribution of the transcripts in the tissue sample is transferred directly to the surface of the object substrate. The object substrates used for optimising the conditions for capturing a transcriptome (e.g. wherein the capture probes do not contain a positional domain and/or the probes are immobilized uniformly on the surface of the object substrate) are relatively inexpensive in comparison to an object substrate on which capture probes comprising a positional domain are arrayed, such that each feature comprises a species of capture probe with a unique positional domain. However, the optimum conditions determined using the inexpensive object substrate can be used to perform analyses using the expensive arrays. Hence the methods may also be seen to reduce costs over other spatial transcriptomics methods. Thus, this aspect of the method may be viewed as providing or enabling a so-called "quality control" (QC) step to determine the optimum or most appropriate, e.g. cost-effective, conditions in which to perform a more detailed analysis using more expensive arrays.

The methods of the invention also represent a significant advance over other methods for spatial transcriptomics known in the art. For example the methods described herein may result in a global and spatial profile of all transcripts in the tissue sample or a portion thereof. Moreover, the methods may enable the expression of every gene to be quantified for each position or feature on an array, which enables a multiplicity of analyses to be performed based on data from a single assay. Thus, the methods of the present invention make it possible to detect and/or quantify the spatial expression of all genes in single tissue sample or a portion thereof. In some aspects of the invention the abundance of the transcripts also may be visualised both directly and indirectly. When the methods include methods of indirect detection, e.g. sequence analysis, it is possible to measure the expression of genes in a single sample simultaneously even wherein said transcripts are present at vastly different concentrations in the same sample.

As described in more detail below, any method of nucleic acid analysis may be used in the analysis step (j). Typically this may involve sequencing, but it is not necessary to perform an actual sequence determination. For example sequence-specific methods of analysis may be used. For example a sequence-specific amplification reaction may be performed, for example using primers which are specific for the positional domain and/or for a specific target sequence, e.g. a particular target DNA to be detected (i.e. corresponding to a particular cDNA/RNA etc). An exemplary analysis method is a sequence-specific PCR reaction.

The sequence analysis information obtained in step (j) may be used to obtain spatial information as to the RNA in the sample or a portion of the sample. In other words the sequence analysis information may provide information as to the location of the RNA in the tissue sample. This spatial information may be derived from the nature of the sequence analysis information determined, for example it may reveal the presence of a particular RNA which may itself be spatially informative in the context of the tissue sample used, and/or the spatial information (e.g. spatial localisation) may be derived from the position of the tissue sample on the array, coupled with the sequencing information. Thus, the method may involve simply correlating the sequence analysis information to a position in the tissue sample e.g. by virtue of the positional tag and its correlation to a position in the tissue sample. However, as described above, spatial information may conveniently be obtained by correlating the expression data, e.g. the intensity of the signal from the labelled cDNA detected, e.g. imaged, in step (e) or the sequence analysis data obtained from step (j), to an image of the tissue sample and this represents one preferred embodiment of the invention. Accordingly, in a preferred embodiment the method also includes a step of:

(f) imaging the tissue sample wherein the tissue sample is imaged before or after step (c), preferably wherein the image of the labelled cDNA is correlated with an image of said tissue sample.

Hence, the method described in the third aspect of the invention may comprise a step of:

(k) correlating said sequence analysis information with an image of said tissue sample, wherein the tissue sample is imaged before or after step (c).

In its broadest sense, the method of the invention may be used for localized or spatial detection of a nucleic acid, specifically RNA, in a tissue sample. Thus, in one embodiment, the method of the invention may be used for determining and/or analysing all of the transcriptome of a tissue sample e.g. the global transcriptome of a tissue sample. However, the method is not limited to this and encompasses determining and/or analysing all or part of the transcriptome of a tissue sample or a portion thereof. Thus, the method may involve determining and/or analysing a part or subset of the transcriptome, e.g. a transcriptome corresponding to one gene or a subset of genes, e.g. a set of particular genes, for example related to a particular disease or condition, tissue type etc. Alternatively or additionally, the method may involve determining and/or analysing all of the transcriptome of a portion of a tissue sample.

Viewed from another aspect, the method steps set out above can be seen as providing a method of obtaining a spatially defined transcriptome, and in particular the spatially defined global transcriptome, of a tissue sample or portion thereof.

Alternatively viewed, the method of the invention may be seen as a method for localised or spatial detection of nucleic acid, e.g. RNA, in a tissue sample or a portion thereof, or for localised or spatial determination and/or analysis of nucleic acid (e.g. RNA) in a tissue sample or a portion thereof. In particular, the method may be used for the localised or spatial detection or determination and/or analysis of gene expression in a tissue sample or a portion thereof. The localised/spatial detection/determination/analysis means that the RNA may be localised to its native position or location within a cell or tissue in the tissue sample. Thus for example, the RNA may be localised to a cell or group of cells, or type of cells in the sample, or to particular regions of areas within a tissue sample. The native location or position of the RNA (or in other words, the location or position of the RNA in the tissue sample), e.g. an expressed gene, may be determined.

The invention may also be viewed as providing methods for determining the optimum conditions for localised detection and/or analysis of nucleic acids in a tissue sample on an object substrate, i.e. for capturing and/or labelling nucleic acids from a tissue sample on an object substrate, e.g. a slide or chip.

The invention can also be seen to provide an object substrate, e.g. a slide or chip, for use in the methods of the invention comprising a substrate on which one or more species of capture probe is directly or indirectly immobilized such that each probe is oriented to have a free 3' end to enable said probe to function as a reverse transcriptase (RT) primer.

Optionally the probes are immobilised uniformly on the object substrate, i.e. the probes are not arrayed as distinct features. Hence, in some embodiments the object substrate of the invention may be viewed as a featureless array, i.e. a microarray without distinct features, which are defined below. In a particular embodiment of the invention, one species of capture probe is immobilized on the object surface, i.e. the capture probes are identical.

In some embodiments of the invention the probes are capable of hybridizing to (i.e. capturing) all mRNA, i.e. RNA molecules with a polyA tail. Hence, in particularly preferred embodiments of the invention the probes may comprise sequences of consecutive dTTP or dUTP nucleotides, e.g. oligoT and/or oligoU, as described in more detail below. In a preferred embodiment of the invention, the object substrate of the invention is for use in methods for determining the optimum conditions for the localised or spatial detection of transcripts from a tissue sample on an object substrate, e.g. array.

In some embodiments of the invention the probes may be capable of hybridizing to (i.e. capturing) specific types of mRNA, i.e. RNA expressed from a specific gene of set of genes. Hence, in some embodiments of the invention the probes may comprise gene specific sequences or sequences that are degenerate for a family of genes. In a preferred embodiment of the invention, the object substrate of the invention is for use in methods for determining and/or analysing one or more transcripts from a tissue sample or a portion thereof.

It will be seen therefore that the object substrate of the present invention may be used to capture RNA, e.g. mRNA, of a tissue sample that is contacted with said array. The array may also be used for determining and/or analysing a partial or global transcriptome of a tissue sample or for obtaining a spatially defined partial or global transcriptome of a tissue sample. The object substrate may be for use in methods of the invention that may be considered as methods of determining, e.g. quantifying, the localised or spatial expression of one or more genes in a tissue sample or portion thereof. Expressed another way, the object substrate may be for use in methods used to detect the spatial expression of one or more genes in a tissue sample or portion thereof. In yet another way, the object substrate may be for use in methods used to determine simultaneously the expression of one or more genes at one or more positions within a tissue sample or a portion thereof. Still further, the object substrate may be for use in methods for partial or global transcriptome analysis of a tissue sample or portion thereof with two-dimensional spatial resolution.

The RNA may be any RNA molecule which may occur in a cell. Thus it may be mRNA, tRNA, rRNA, viral RNA, small nuclear RNA (snRNA), small nucleolar RNA (snoRNA), microRNA (miRNA), small interfering RNA (sRNA), piwi-interacting RNA (piRNA), ribozymal RNA, antisense RNA or non-coding RNA. Preferably however it is mRNA.

Step (c) in the methods above of generating cDNA from the captured RNA will be seen as relating to the synthesis of the cDNA. This will involve a step of reverse transcription of the captured RNA, extending the capture probe, which functions as the RT primer, using the captured RNA as template. Such a step generates so-called first strand cDNA. As will be described in more detail below, second strand cDNA synthesis may optionally take place on the array, or it may take place in a separate step, after release of first strand cDNA from the array. As also described in more detail below, in certain embodiments second strand synthesis may occur in the first step of amplification of a released first strand cDNA molecule.

Step (d) in the methods above of labelling the cDNA molecules generated in step (c) will be seen as relating to any suitable method of labelling the cDNA molecules. In particular, the label will be provided to, e.g. as part of, or on, the generated cDNA molecule. In preferred embodiments of the invention, the labelling step is performed contemporaneously with, i.e. at the same time as, the generating step. Thus, labelling the may involve the incorporation of labelled nucleotides into the synthesized cDNA molecule directly. As discussed in more detail below, the nucleotides may be labelled with directly or indirectly signal giving molecules. For instance, directly signal giving labels may be fluorescent molecules, i.e. the labelled nucleotides may be fluorescently labelled nucleotides. Indirectly signal giving labels may be, for example, biotin molecules, i.e. the labelled nucleotides may be biotin labelled nucleotides, which require additional steps to provide a signal, e.g. the addition of streptavidin conjugated to an enzyme which may act on a chemical substrate to provide a detectable signal, e.g. a visibly detectable colour change.

In some embodiments the cDNA generated in step (c) may be labelled after its synthesis, e.g. stained. Various methods for labelling nucleic acid molecules are known in the art and could be employed in the methods of the invention. For instance, the cDNA may be stained with a nucleic acid stain. If the cDNA generating step only creates a first strand of cDNA, it may be advantageous to use a strain capable of detecting single stranded nucleic acid such as SYBR Gold® or GelStar®, as the RNA template may degrade. However, if a second strand of cDNA is generated a stain capable of detecting double stranded nucleic acid, such as ethidium bromide or SYBR Green® may be used. In some embodiments it may be advantageous to remove the tissue sample from the object substrate before labelling the cDNA, e.g. to avoid background signals from nucleic acid material remaining in the tissue sample, e.g. genomic DNA etc. In embodiments where it is desirable to image the tissue sample to be able to correlate the detection, e.g. image, of the labelled cDNA with an image of the tissue sample, it may be desirable to image the tissue sample before the step of generating the cDNA and particularly before the step of labelling the cDNA.

The "object substrate" or "substrate" of the invention may be any solid substrate on which nucleic acid molecules can be immobilized directly or indirectly, e.g. a slide or chip. In preferred embodiments the object substrate may be viewed as being an array substrate, i.e. any substrate that could be used to generate a nucleic acid array, e.g. a microarray substrate. In many embodiments the capture probes may be immobilized on the object substrate in the form of an array, i.e. in some embodiments the object substrate is an array, e.g. a microarray. In other embodiments the capture probes are not immobilized on the object substrate in an array format, i.e. the substrate may have no distinct features and the capture probes may be immobilized on the object substrate uniformly. Hence, in some embodiments the object substrate is not an array. Alternatively, the object subject may be viewed as a featureless array or alternatively as an array comprising a single large feature. Array substrates, i.e. object substrates, for use in the context of nucleic acid analysis are discussed and described below.

As used herein the term "multiple" means two or more, or at least two, e.g. 3, 5, 10, 15, 20, 30, 40, 50, 60, 70, 80, 90, 100, 150, 200, 400, 500, 1000, 2000, 5000, 10,000, or more etc. Thus for example, the number of distinct capture probes (i.e. capture probes with different sequences, e.g. different positional domains) may be any integer in any range between any two of the aforementioned numbers. It will be appreciated however that it is envisaged that conventional-type arrays with many hundreds, thousands, tens of thousands, hundreds of thousands or even millions of capture probes may be used.

Thus, the methods outlined herein may utilise, but are not limited to, high density nucleic acid arrays comprising "capture probes" for capturing and labelling transcripts from all of the single cells within a tissue sample e.g. a thin tissue sample slice, or "section". The tissue samples or sections for analysis are produced in a highly parallelized fashion, such that the spatial information in the section is retained. The captured RNA (preferably mRNA) molecules for each cell, or "transcriptomes", are transcribed into cDNA and the resultant cDNA molecules are labelled and detected and/or analyzed. In the first instance the labelled cDNA molecules are detected and/or analysed by detecting the signal from the labelled molecules, e.g. by imaging the object substrate such that the signal from the label can be detected, e.g. quantified. The labelled cDNA molecules, or a portion thereof, may be subject to analysis, e.g. by high throughput sequencing. The resultant data from the first and/or subsequent detection and/or analysis may be correlated to images of the original tissue samples. For instance, an overlay of the two images may be used to determine areas of high, low or no expression, which may enable portions of the tissue sample to be selected for further analysis. The data from the further analyses may be correlated to images of the tissue sample by, e.g. so-called barcode sequences (or ID tags, defined herein as positional domains) incorporated into the arrayed nucleic acid probes.

High density nucleic acid arrays or microarrays form a core component of some of the spatial transcriptome labelling methods described herein. A microarray is a multiplex technology used in molecular biology. A typical microarray consists of an arrayed series of microscopic spots of oligonucleotides (hundreds of thousands of spots, generally tens of thousands, can be incorporated on a single array). The distinct position of each nucleic acid (oligonucleotide) spot (each species of oligonucleotide/nucleic acid molecule) is known as a "feature" (and hence in some of the methods set out above each species of capture probe may be viewed as a specific feature of the array; each feature occupies a distinct position on the array), and typically each separate feature contains in the region of picomoles ($10^{-12}$ moles) of a specific DNA sequence (a "species"), which are known as "probes" (or "reporters"). Typically, these can be a short section of a gene or other nucleic acid element to which a cDNA or cRNA sample (or "target") can hybridize under high-stringency hybridization conditions. However, as described below, the probes of the present invention and/or their distribution on the array may differ from the probes of standard microarrays.

In gene expression microarrays, probe-target hybridization is usually detected and quantified by detection of visual signal, e.g. a fluorophore, silver ion, or chemiluminescence-label, which has been incorporated into all of the targets before the targets are contacted with the array. The intensity of the visual signal correlates to the relative abundance of each target nucleic acid in the sample, but does not provide any spatial information about the origin of the target nucleic acid in the sample. Since an array can contain tens of thousands of probes, a microarray experiment can accomplish many genetic tests in parallel.

In standard microarrays, the probes are attached to a solid surface or substrate by a covalent bond to a chemical matrix, e.g. epoxy-silane, amino-silane, lysine, polyacrylamide etc. The substrate typically is a glass, plastic or silicon chip or slide, although other microarray platforms are known, e.g. microscopic beads.

The probes may be attached to the object substrate, e.g. array, of the invention by any suitable means. In a preferred embodiment the probes are immobilized to the substrate by chemical immobilization. This may be an interaction between the substrate (support material) and the probe based on a chemical reaction. Such a chemical reaction typically does not rely on the input of energy via heat or light, but can be enhanced by either applying heat, e.g. a certain optimal temperature for a chemical reaction, or light of certain wavelength. For example, a chemical immobilization may take place between functional groups on the substrate and corresponding functional elements on the probes. Such corresponding functional elements in the probes may either be an inherent chemical group of the probe, e.g. a hydroxyl group or be additionally introduced. An example of such a functional group is an amine group. Typically, the probe to be immobilized comprises a functional amine group or is chemically modified in order to comprise a functional amine group. Means and methods for such a chemical modification are well known.

The localization of said functional group within the probe to be immobilized may be used in order to control and shape the binding behaviour and/or orientation of the probe, e.g. the functional group may be placed at the 5' or 3' end of the probe or within sequence of the probe. A typical substrate for a probe to be immobilized comprises moieties which are capable of binding to such probes, e.g. to amine-functionalized nucleic acids. Examples of such substrates are carboxy, aldehyde or epoxy substrates. Such materials are known to the person skilled in the art. Functional groups, which impart a connecting reaction between probes that are chemically reactive by the introduction of an amine group, and array substrates are known to the person skilled in the art.

Alternative substrates on which probes may be immobilized may have to be chemically activated, e.g. by the activation of functional groups, available on the object substrate, e.g. array substrate. The term "activated substrate" relates to a material in which interacting or reactive chemical functional groups were established or enabled by chemical modification procedures as known to the person skilled in the art. For example, a substrate comprising carboxyl groups has to be activated before use. Furthermore, there are substrates available that contain functional groups that can react with specific moieties already present in the nucleic acid probes.

In some embodiments the probes may be immobilized on beads, e.g. plastic microbeads, which can be used to immobilize the probes on the substrate. Suitable techniques for immobilizing the nucleic acid molecules on beads may be selected from the techniques discussed above or selected from methods known in the art. The beads may be contacted with, and immobilized on, an object substrate, thereby indirectly immobilizing the probes on the surface of the substrate. For example, after contacting the beads with the substrate, the substrate may be treated crosslink the beads to each other and/or the surface of the substrate, e.g. the substrate may heated to partially melt the beads which are allowed to solidify, to generate an object substrate on which probes are indirectly immobilized.

Alternatively, the probes may be synthesized directly on the substrate. Suitable methods for such an approach are known to the person skilled in the art. Examples are manufacture techniques developed by Agilent Inc., Affymetrix Inc., Roche Nimblegen Inc. or Flexgen BV. Typically, lasers and a set of mirrors that specifically activate the spots where nucleotide additions are to take place are used. Such an approach may provide, for example, spot sizes (i.e. features) of around 30 µm or larger. However, in some embodiments the probes may be immobilized uniformly on the substrate, i.e. a uniform, consistent or homogeneous distribution of probes across the surface of the substrate. Hence, it may be necessary simply to activate a portion or area of the substrate on which the probes will be immobilized. A "portion" of the substrate is described below.

The object substrate therefore may be any suitable substrate known to the person skilled in the art. The substrate may have any suitable form or format, e.g. it may be flat, curved, e.g. convexly or concavely curved towards the area where the interaction between the tissue sample and the substrate takes place. Particularly preferred is the where the substrate is a flat, i.e. planar, such as a chip or slide.

Typically, the substrate is a solid support and thereby allows for an accurate and traceable positioning of the probes on the substrate. An example of a substrate is a solid material or a substrate comprising functional chemical groups, e.g. amine groups or amine-functionalized groups. A substrate envisaged by the present invention is a non-porous substrate. Preferred non-porous substrates are glass, silicon, poly-L-lysine coated material, nitrocellulose, polystyrene, cyclic olefin copolymers (COCs), cyclic olefin polymers (COPs), polypropylene, polyethylene and polycarbonate.

Any suitable material known to the person skilled in the art may be used. Typically, glass or polystyrene is used. Polystyrene is a hydrophobic material suitable for binding negatively charged macromolecules because it normally contains few hydrophilic groups. For nucleic acids immobilized on glass slides, it is furthermore known that by increasing the hydrophobicity of the glass surface the nucleic acid immobilization may be increased. Such an enhancement may permit a relatively more densely packed formation, which is advantageous when the probes are arranged in an array format. In addition to a coating or surface treatment with poly-L-lysine, the substrate, in particular glass, may be treated by silanation, e.g. with epoxy-silane or amino-silane or by silynation or by a treatment with polyacrylamide.

A number of standard arrays and array substrates are commercially available and both the number and size of the features may be varied. In the present invention, when the probes are distributed uniformly on the surface of the substrate, the concentration of the probes immobilized may be altered to correspond to the size and/or density of the cells present in different tissues or organisms. Similarly, when the probes are in an array format the arrangement of the features may be altered to correspond to the size and/or density of the cells present in different tissues or organisms. For instance, animal cells typically have a cross-section in the region of 1-100 µm, whereas the cross-section of plant cells typically may range from 1-10000 µm. Hence, in embodiments where the probes are arrayed on the substrate, Nimblegen® arrays, which are available with up to 2.1 million features, or 4.2 million features, and feature sizes of 13 micrometers, may be preferred for tissue samples from an animal or fungus, whereas other formats, e.g. with 8×130 k features, may be sufficient for plant tissue samples. Commercial arrays are also available or known for use in the context of sequence analysis and in particular in the context of NGS technologies. Such arrays may also be used as the substrate, e.g. array substrate in the context of the present invention, e.g. an Illumina bead array. In addition to commercially available arrays, which can themselves be customized, it is possible to make custom or non-standard "in-house" arrays and methods for generating arrays are well-established. The methods of the invention may utilise both standard and non-standard arrays that comprise probes as defined below.

The probes on a substrate may be immobilized, i.e. attached or bound, to the substrate, e.g. array, via the 5' or 3' end, depending on the chemical matrix of the array. Typically, for commercially available arrays, the probes are attached via a 3' linkage, thereby leaving a free 5' end. However, substrates, e.g. arrays, comprising probes attached to the substrate via a 5' linkage, thereby leaving a free 3' end, are available and may be synthesized using standard techniques that are well known in the art and are described elsewhere herein.

The covalent linkage used to couple a nucleic acid probe to a substrate may be viewed as both a direct and indirect linkage, in that the although the probe is attached by a "direct" covalent bond, there may be a chemical moiety or linker separating the "first" nucleotide of the nucleic acid probe from the, e.g. glass or silicon, substrate i.e. an indirect linkage. For the purposes of the present invention probes that are immobilized to the substrate by a covalent bond and/or chemical linker are generally seen to be immobilized or attached directly to the substrate.

As will be described in more detail below, the capture probes of the invention may be immobilized on, or interact with, the substrate, e.g. array, directly or indirectly. Thus the capture probes need not bind directly to the substrate, but may interact indirectly, for example by binding to a molecule which itself binds directly or indirectly to the array (e.g. the capture probe may interact with (e.g. bind or hybridize to) a binding partner for the capture probe, i.e. a surface probe, which is itself bound to the substrate directly or indirectly). Generally speaking, however, the capture probe will be, directly or indirectly (by one or more intermediaries), bound to, or immobilized on, the substrate.

The method and object substrate, e.g. slide or chip, of the invention may comprise probes that are immobilized via their 5' or 3' end. However, when the capture probe is immobilized directly to the array substrate, it may be immobilized only such that the 3' end of the capture probe is free to be extended, e.g. it is immobilized by its 5' end. The capture probe may be immobilized indirectly, such that it has a free, i.e. extendible, 3' end.

By extended or extendible 3' end, it is meant that further nucleotides may be added to the most 3' nucleotide of the nucleic acid molecule, e.g. capture probe, to extend the length of the nucleic acid molecule, i.e. the standard polymerization reaction utilized to extend nucleic acid molecules, e.g. templated polymerization catalyzed by a polymerase.

Thus, in one embodiment, the substrate, e.g. array, comprises probes that are immobilized directly via their 3' end, so-called surface probes, which are defined below. Each species of surface probe comprises a region of complementarity to each species of capture probe, such that the capture probe may hybridize to the surface probe, resulting in the capture probe comprising a free extendible 3' end. In a preferred aspect of the invention, when the substrate comprises surface probes, the capture probes are synthesized in situ on the substrate.

The probes may be made up of ribonucleotides and/or deoxyribonucleotides as well as synthetic nucleotide residues that are capable of participating in Watson-Crick type or analogous base pair interactions. Thus, the nucleic acid domain may be DNA or RNA or any modification thereof, e.g. PNA or other derivatives containing non-nucleotide backbones. However, the capture probe, e.g. the capture domain of the capture probe, must capable of priming a reverse transcription reaction to generate cDNA that is complementary to the captured RNA molecules.

In a preferred embodiment of the invention at least the capture domain of the capture probe comprises or consists of deoxyribonucleotides (dNTPs). In a particularly preferred embodiment the whole of the capture probe comprises or consists of deoxyribonucleotides.

In a preferred embodiment of the invention the capture probes are immobilized on the substrate directly, i.e. by their 5' end, resulting in a free extendible 3' end.

The capture probes of the invention comprise at least one domain, a capture domain, which is capable of interacting with (i.e. binding or hybridizing to) the RNA from the tissue, i.e. to capture the RNA. In some embodiments in which the capture probes are arrayed on the substrate, the probes preferably comprise at least two domains, a capture domain and a positional domain (or a feature identification tag or domain; the positional domain may alternatively be defined as an identification (ID) domain or tag, or as a positional tag). The capture probe may further comprise a universal domain as defined further below. Where the capture probe is indirectly attached to the array surface via hybridization to a surface probe, the capture probe requires a sequence (e.g. a portion or domain) which is complementary to the surface probe. Such a complementary sequence may be complementary to a positional/identification domain (if present in the capture probe) and/or a universal domain on the surface probe. In other words the positional domain and/or universal domain may constitute the region or portion of the probe which is complementary to the surface probe. However, the capture probe may also comprise an additional domain (or region, portion or sequence) which is complementary to the surface probe. For ease of synthesis, as described in more detail below, such a surface probe-complementary region may be provided as part of, or as an extension of, the capture domain (such a part or extension not itself being used for, or capable of, binding to the target nucleic acid, e.g. RNA).

Thus, in their simplest form the capture probes for use in the invention may comprise or consist of a capture domain. However, in some embodiments of the invention the capture probes may comprise or consist of: (i) a capture domain and a positional domain; (ii) a capture domain and a universal domain; (iii) a capture domain and a domain that is complementary to a surface probe; (iv) a capture domain, positional domain and a universal domain, and so forth.

In some embodiments a single species of capture probe is immobilized to the substrate, preferably wherein the capture probe is immobilized on the substrate uniformly. However, a single species of capture probe may be arrayed on the substrate, such that each feature on the array comprises the same probe. In some embodiments multiple species of capture probe are immobilized to the substrate, preferably wherein each species of capture probe is immobilized at a different position on the substrate (i.e. each species forms a feature in an array), although a single capture probe may in some embodiments be immobilized at more than one position (a single species of capture probe may be used to form more than one feature). In some embodiments multiple species of capture probe may be combined to form a mixture which is immobilized on the substrate uniformly, i.e. such that there is an even distribution of each species of capture probe on the surface of the substrate.

The capture domain is typically located at the 3' end of the capture probe and comprises a free 3' end that can be extended, e.g. by template dependent polymerization. The capture domain comprises a nucleotide sequence that is capable of hybridizing to nucleic acid, e.g. RNA (preferably mRNA) present in the cells of the tissue sample contacted with the array.

Advantageously, the capture domain may be selected or designed to bind (or put more generally may be capable of binding) selectively or specifically to the particular nucleic acid, e.g. RNA, it is desired to detect or analyse. For example the capture domain may be selected or designed for the selective capture of mRNA. As is well known in the art, this may be on the basis of hybridisation to the poly-A tail of mRNA. Thus, in a preferred embodiment the capture domain comprises a poly-T DNA oligonucleotide, i.e. a series of consecutive deoxythymidine residues linked by phosphodiester bonds, which is capable of hybridizing to the poly-A tail of mRNA. Alternatively, the capture domain may comprise nucleotides which are functionally or structurally analogous to poly-T, i.e. are capable of binding selectively to poly-A, for example a poly-U oligonucleotide or an oligonucleotide comprised of deoxythymidine analogues, wherein said oligonucleotide retains the functional property of binding specifically to poly-A. In a particularly preferred embodiment the capture domain, or more particularly the poly-T element of the capture domain, comprises at least 10 nucleotides, preferably at least 11, 12, 13, 14, 15, 16, 17, 18, 19 or 20 nucleotides. In such embodiments, the poly-T element of the capture domain may comprise up to 30 or up to 35 nucleotides. In a further embodiment, the capture domain, or more particularly the poly-T element of the capture domain comprises at least 25, 30 or 35 nucleotides. For instance, the poly-T element of the capture domain may comprise 10-14 nucleotides, 15-25 nucleotides or 25-35 nucleotides.

Random sequences may also be used in the capture of nucleic acid, as is known in the art, e.g. random hexamers or similar sequences, and hence such random sequences may be used to form all or a part of the capture domain. For example, random sequences may be used in conjunction with poly-T (or poly-T analogue etc.) sequences. Thus where a capture domain comprises a poly-T (or a "poly-T-like") oligonucleotide, it may also comprise a random oligonucleotide sequence. This may for example be located 5' or 3' of the poly-T sequence, e.g. at the 3' end of the capture probe, but the positioning of such a random sequence is not critical. Such a construct may facilitate the capturing of the initial part of the poly-A of mRNA. Alternatively, the capture domain may be an entirely random sequence. Degenerate capture domains may also be used, according to principles known in the art.

The capture domain may be capable of binding selectively to a desired sub-type or subset of nucleic acid, e.g. RNA, for example a particular type of RNA such mRNA or rRNA etc. as listed above, or to a particular subset of a given type of RNA, for example, a particular mRNA species e.g. corresponding to a particular gene or group of genes. Such a capture probe may be selected or designed based on sequence of the RNA it is desired to capture. Thus it may be a sequence-specific capture probe, specific for a particular RNA target or group of targets (target group etc). Thus, it may be based on a particular gene sequence or particular motif sequence or common/conserved sequence etc., according to principles well known in the art.

In embodiments where the capture probe is immobilized on the substrate indirectly, e.g. via hybridization to a surface probe, the capture domain may further comprise an upstream sequence (5' to the sequence that hybridizes to the nucleic acid, e.g. RNA of the tissue sample) that is capable of hybridizing to 5' end of the surface probe. Alone, the capture domain of the capture probe may be seen as a capture domain oligonucleotide, which may be used in the synthesis of the capture probe in embodiments where the capture probe is immobilized on the array indirectly.

The positional domain (feature identification domain or tag) of the capture probe, if present, is located directly or indirectly upstream, i.e. closer to the 5' end of the capture probe nucleic acid molecule, of the capture domain. Preferably the positional domain is directly adjacent to the capture domain, i.e. there is no intermediate sequence between the capture domain and the positional domain. In some embodiments the positional domain forms the 5' end of the capture probe, which may be immobilized directly or indirectly on the substrate of the array.

As discussed above, when the capture probes are arrayed on the substrate, each feature (distinct position) of the array comprises a spot of a species of nucleic acid probe, preferably wherein the positional domain at each feature is unique. In some embodiments, the same positional domain may be used for a group of features, preferably a group of features in close proximity to each other. For instance, when multiple species of capture probes that contain different capture domains are used on the same substrate, it may be advantageous to use the same positional domain for each type of capture domain that is immobilized in a group of directly or indirectly adjacent features.

Directly adjacent features are neighbouring features on the array, for instance if the features are arrayed in a standard grid formation, any single feature will have 8 features that are directly adjacent. Indirectly adjacent features may be viewed as features that are in close proximity to each other, i.e. they are immobilized within a specific area on the array surface, but may have one or more features separating them, e.g. 1, 2, 3, 4 or 5 features may separate indirectly adjacent features. In some cases, e.g. on high density arrays, indirectly adjacent features may be separated by up to 10, 20, 30, 40 or 50 features.

A "species" of capture probe is defined with reference to the sequence of the capture domain and, if present, its positional domain; a single species of capture probe will have a unique capture domain sequence and/or unique combination of capture domain sequence and positional domain sequence. However, it is not required that each member of a species of capture probe has the same sequence in its entirety. In particular, since the capture domain may be or may comprise a random or degenerate sequence, the capture domains of individual probes within a species may vary. Accordingly, in some embodiments where the capture domains of the capture probes are the same, each feature comprises a single probe sequence. However in other embodiments where the capture domain varies, members of a species of probe will not have the exact same sequence, although the sequence of the positional domain of each member in the species will be the same. What is required is that each feature or position of the array carries a capture probe of a single species (specifically each feature or position carries a capture probe which has an identical positional tag, i.e. there is a single positional domain at each feature or position, although probes immobilized at directly or indirectly adjacent features may comprise the same positional domain if they comprise different capture domains). Each species has a different capture domain, positional domain and/or combination of capture domain and positional domain which identifies the species. However, each member of a species, may in some cases, as described in more detail herein, have a different capture domain, as the capture domain may be random or degenerate or may have a random or degenerate component. This means that within a given feature, or position, the capture domain of the probes may differ.

Thus in some, but not necessarily in all embodiments, the nucleotide sequence of any one probe molecule immobilized at a particular feature is the same as the other probe molecules immobilized at the same feature, but the nucleotide sequence of the probes at each feature is different, distinct or distinguishable from the probes immobilized at every other feature. Preferably each feature comprises a different species of probe. However, in some embodiments it may be advantageous for a group of features to comprise the same species of probe, i.e. effectively to produce a feature covering an area of the array that is greater than a single feature, e.g. to lower the resolution of the array. In other embodiments of the array, the nucleotide sequence of the positional domain of any one probe molecule immobilized at a particular feature may be the same as the other probe molecules immobilized at the same feature but the capture domain may vary. The capture domain may nonetheless be designed to capture the same type of molecule, e.g. mRNA in general.

The positional domain (or tag), when present in the capture probe, comprises the sequence which is unique to each feature or a group of directly or indirectly adjacent features, and acts as a positional or spatial marker (the identification tag). In this way each region or domain of the tissue sample, e.g. each cell in the tissue, may be identified by spatial resolution across the array linking the nucleic acid, e.g. RNA (e.g. the transcripts) from a certain cell to a unique positional domain sequence in the capture probe. The positional domain of a capture probe in the array is one aspect of the methods of the invention that allows a specific transcript (or group of transcripts) to be correlated to a position in the tissue sample, for example it may be correlated to a cell in the sample. Thus, the positional domain of the capture domain may be seen as a nucleic acid tag (identification tag) and enables the position of a transcript to be correlated to a position in the sample indirectly, e.g. by analysis of the sequence of the captured transcript.

In some embodiments of the present invention, the methods allow a specific transcript (or group of transcripts) to be correlated to a position in the tissue sample directly, i.e. without the need for sequence analysis. For instance, a species of capture probe may be immobilized on a substrate (either in an array format or uniformly), wherein the capture domain of the capture probe is specific for a transcript (or group of transcripts). Only the specific transcript(s) will interact with (hybridize to) the capture probes. The transcripts will be captured on the substrate in a position relative to where the transcript is expressed in the tissue sample. The steps of generating and labelling the cDNA molecules using the captured transcript as a template and subsequent detection, e.g. imaging, of the labelled cDNA will allow the spatial expression pattern of the transcript to be determined directly. The information obtained from the spatial detection, e.g. image, of the labelled cDNA may be correlated with an image the tissue sample to determine the precise areas of expression in the tissue sample.

It will be evident that multiple species of capture probe, each specific for a different transcript could be used to determine the expression pattern of multiple genes simultaneously. In a preferred embodiment the species of capture probe are arrayed on the substrate and the capture probes comprise a positional domain. In some embodiments groups of adjacent features (i.e. defining a small area on the array) may comprise capture probes with the same positional domain and different capture domains. The step of detecting, e.g. imaging, the labelled cDNA will provide a preliminary analysis of where the transcripts are expressed in the tissue sample. If more specific expression analysis is required or desirable, the immobilized cDNA molecules may be processed and analysed further, as described below. Sequence analysis of the immobilised cDNA allows the position of a particular transcript to be correlated to a position in the tissue sample, e.g. a cell, by virtue of the positional domain in the capture probe.

Alternatively or additionally, the labelled cDNA may be used to as a marker to select areas of cDNA immobilized on the substrate (which are representative of expression activity in the tissue sample) for further analysis. For instance, immobilized cDNA molecules may be removed from all areas of the substrate except the area of interest, e.g. by laser ablation, and the remaining immobilized cDNA molecules may be processed and analysed as described in more detail below. The removal of immobilized cDNA molecules from the surface of the substrate, e.g. from regions that correspond to cell or tissues in the tissue sample that are not of interest or from regions where the signal from the labelled cDNA molecules indicates that the transcripts are expressed above or below a specific threshold level, reduces the amount of further analysis required, i.e. fewer cDNA molecules for analysis means that less sequence analysis is required, which may result in a reduction in the amount of reagents and/or time required to perform the analysis.

Any suitable sequence may be used as the positional domain in the capture probes of the invention. By a suitable sequence, it is meant that the positional domain should not interfere with (i.e. inhibit or distort) the interaction between the RNA of the tissue sample and the capture domain of the capture probe. For example, the positional domain should be designed such that nucleic acid molecules in the tissue sample do not hybridize specifically to the positional domain. Preferably, the nucleic acid sequence of the positional domain of the capture probes has less than 80% sequence identity to the nucleic acid sequences in the tissue sample. Preferably, the positional domain of the capture probe has less than 70%, 60%, 50% or less than 40% sequence identity across a substantial part of the nucleic acids molecules in the tissue sample. Sequence identity may be determined by any appropriate method known in the art, e.g. using the BLAST alignment algorithm.

In a preferred embodiment the positional domain of each species of capture probe contains a unique barcode sequence. The barcode sequences may be generated using random sequence generation. The randomly generated sequences may be followed by stringent filtering by mapping to the genomes of all common reference species and with pre-set Tm intervals, GC content and a defined distance of difference to the other barcode sequences to ensure that the barcode sequences will not interfere with the capture of the nucleic acid, e.g. RNA from the tissue sample and will be distinguishable from each other without difficulty.

As mentioned above, in some embodiments, the capture probe may comprise a universal domain (or linker domain or tag). The universal domain of the capture probe is located directly or indirectly upstream, i.e. closer to the 5' end of the capture probe nucleic acid molecule, of the capture domain or, if present, the positional domain. Preferably the universal domain is directly adjacent to the capture domain or, if present, the positional domain, i.e. there is no intermediate sequence between the capture domain and the universal domain or the positional domain and the universal domain. In embodiments where the capture probe comprises a universal domain, the domain will form the 5' end of the capture probe, which may be immobilized directly or indirectly on the substrate of the array.

The universal domain may be utilized in a number of ways in the methods of the invention. For example, in some embodiments the methods of the invention comprise a step of releasing (e.g. removing) at least part of the synthesised (i.e. extended) nucleic acid, e.g. cDNA molecules from the surface of the array. As described elsewhere herein, this may be achieved in a number of ways, of which one comprises cleaving the nucleic acid, e.g. cDNA molecule from the surface of the array. Thus, the universal domain may itself comprise a cleavage domain, i.e. a sequence that can be cleaved specifically, either chemically or preferably enzymatically.

Thus, the cleavage domain may comprise a sequence that is recognised by one or more enzymes capable of cleaving a nucleic acid molecule, i.e. capable of breaking the phosphodiester linkage between two or more nucleotides. For instance, the cleavage domain may comprise a restriction endonuclease (restriction enzyme) recognition sequence. Restriction enzymes cut double-stranded or single stranded DNA at specific recognition nucleotide sequences known as restriction sites and suitable enzymes are well known in the art. For example, it is particularly advantageous to use rare-cutting restriction enzymes, i.e. enzymes with a long recognition site (at least 8 base pairs in length), to reduce the possibility of cleaving elsewhere in the immobilized nucleic acid, e.g. cDNA molecule. In this respect, it will be seen that removing or releasing at least part of the nucleic acid, e.g. cDNA molecule requires releasing a part comprising the capture domain of the nucleic acid, e.g. cDNA, and all of the sequence downstream of the capture domain, e.g. all of the sequence that is 3' to the first nucleotide in the capture domain. Hence, cleavage of the nucleic acid, e.g. cDNA molecule should take place 5' to the capture domain. In preferred embodiments, removing or releasing at least part of the nucleic acid, e.g. cDNA, molecule requires releasing a part comprising the positional domain of the nucleic acid, e.g. cDNA and all of the sequence downstream of the positional domain, e.g. all of the sequence that is 3' to the first nucleotide in the positional domain. Hence, cleavage of the nucleic acid, e.g. cDNA molecule should take place 5' to the positional domain.

By way of example, the cleavage domain may comprise a poly-U sequence which may be cleaved by a mixture of Uracil DNA glycosylase (UDG) and the DNA glycosylase-lyase Endonuclease VIII, commercially known as the USER™ enzyme.

A further example of a cleavage domain can be utilised in embodiments where the capture probe is immobilized to the array substrate indirectly, i.e. via a surface probe. The cleavage domain may comprise one or more mismatch nucleotides, i.e. when the complementary parts of the surface probe and the capture probe are not 100% complementary. Such a mismatch is recognised, e.g. by the MutY and T7 endonuclease I enzymes, which results in cleavage of the nucleic acid molecule at the position of the mismatch.

In some embodiments of the invention, the capture domain of the capture probe comprises a cleavage domain, wherein the said cleavage domain is located at the 5' end of the capture domain. This cleavage domain may be viewed as a universal domain or part of the universal domain. In some embodiments of the invention, the positional domain of the capture probe comprises a cleavage domain, wherein the said cleavage domain is located at the 5' end of the positional domain. This cleavage domain may be viewed as a universal domain or part of the universal domain.

The universal domain may comprise also an amplification domain. This may be in addition to, or instead of, a cleavage domain. In some embodiments of the invention, as described elsewhere herein, it may be advantageous to amplify the nucleic acid, e.g. cDNA molecules, for example after they have been released (e.g. removed or cleaved) from the substrate. It will be appreciated however, that the initial cycle of amplification, or indeed any or all further cycles of amplification may also take place in situ on the substrate. The amplification domain comprises a distinct sequence to which an amplification primer may hybridize. The amplification domain of the universal domain of the capture probe is preferably identical for each species of capture probe. Hence a single amplification reaction will be sufficient to amplify all of the nucleic acid, e.g. cDNA, molecules (which may or may not be released from the substrate prior to amplification).

Any suitable sequence may be used as the amplification domain in the capture probes of the invention. By a suitable sequence, it is meant that the amplification domain should not interfere with (i.e. inhibit or distort) the interaction between the nucleic acid, e.g. RNA of the tissue sample, and the capture domain of the capture probe. Furthermore, the amplification domain should comprise a sequence that is not the same or substantially the same as any sequence in the nucleic acid, e.g. RNA of the tissue sample, such that the primer used in the amplification reaction can hybridize only to the amplification domain under the amplification conditions of the reaction.

For example, the amplification domain should be designed such that nucleic acid molecules in the tissue sample do not hybridize specifically to the amplification domain or the complementary sequence of the amplification domain. Preferably, the nucleic acid sequence of the amplification domain of the capture probes and the complement thereof has less than 80% sequence identity to the nucleic acid sequences in the tissue sample. Preferably, the positional domain of the capture probe has less than 70%, 60%, 50% or less than 40% sequence identity across a substantial part of the nucleic acid molecules in the tissue sample. Sequence identity may be determined by any appropriate method known in the art, e.g. the using BLAST alignment algorithm.

Thus, alone, the universal domain of the capture probe may be seen as a universal domain oligonucleotide, which may be used in the synthesis of the capture probe in embodiments where the capture probe is immobilized on the array indirectly.

In some embodiments, the capture domain of the capture probe may be used as an amplification domain. For instance, in embodiments in which the capture probe does not contain a positional domain or universal domain. In a representative embodiment, the capture probe may be used to capture mRNA from a tissue sample, e.g. using a poly-T oligonucleotide. The signal from the labelled cDNA may be detected, e.g. imaged, and a portion of the array may be selected for further analysis. Thus, the unwanted cDNA molecules may be removed from the substrate, e.g. using laser ablation, and the remaining immobilized cDNA molecules may be released and/or amplified using the capture domain as a primer site, i.e. amplified using a poly-A oligonucleotide primer. The sequence analysis may provide positional information even when the captures probes do not contain positional domains because the sequence information is derived from nucleic acid molecules amplified only from a specific region of the substrate, which correlates to a specific region or portion of the tissue sample.

In one representative embodiment of the invention only the positional domain of each species of capture probe is unique. Hence, the capture domains and universal domains (if present) are in one embodiment the same for every species of capture probe for any particular array to ensure that the capture of the nucleic acid, e.g. RNA, from the tissue sample is uniform across the array. However, as discussed above, in some embodiments the capture domains may differ by virtue of including random or degenerate sequences or gene specific sequences.

In embodiments where the capture probe is immobilized on the substrate indirectly, e.g. via hybridisation to a surface probe, the capture probe may be synthesised on the substrate as described below.

The surface probes are immobilized on the substrate directly by or at, e.g. their 3' end. In embodiments where the probes are arrayed on the substrate each species of surface probe may be unique to each feature (distinct position) or groups of features (directly or indirectly adjacent features) of the array and is partly complementary to the capture probe, defined above.

Hence the surface probe comprises at its 5' end a domain (complementary capture domain) that is complementary to a part of the capture domain that does not bind to the nucleic acid, e.g. RNA, of the tissue sample. In other words, it comprises a domain that can hybridize to at least part of a capture domain oligonucleotide. The surface probe may further comprise a domain (complementary positional domain or complementary feature identification domain) that is complementary to the positional domain of the capture probe, if present. The complementary positional domain is located directly or indirectly downstream (i.e. at the 3' end) of the complementary capture domain, i.e. there may be an intermediary or linker sequence separating the complementary positional domain and the complementary capture domain. In embodiments where the capture probe is synthesized on the array surface, the surface probes of the array always comprise a domain (complementary universal domain) at the 3' end of the surface probe, i.e. directly or indirectly downstream of the positional domain (if present), which is complementary to the universal domain of the capture probe. In other words, it comprises a domain that can hybridize to at least part of the universal domain oligonucleotide.

In some embodiments of the invention the sequence of the surface probe shows 100% complementarity or sequence identity to the positional domain (if present) and the universal domain and to the part of the capture domain that does not bind to the nucleic acid, e.g. RNA, of the tissue sample. In other embodiments the sequence of the surface probe may show less than 100% sequence identity to the domains of the capture probe, e.g. less than 99%, 98%, 97%, 96%, 95%, 94%, 93%, 92%, 91% or 90%. In a particularly preferred embodiment of the invention, the complementary universal domain shares less than 100% sequence identity to the universal domain of the capture probe.

In one embodiment of the invention, the capture probe is synthesized or generated on the substrate. In a representative embodiment (see FIG. 1), the substrate comprises surface probes as defined above. Oligonucleotides that correspond to the capture domain and universal domain of the capture probe are contacted with the substrate and allowed to hybridize to the complementary domains of the surface probes. Excess oligonucleotides may be removed by washing the substrate under standard hybridization conditions. The resultant substrate comprises partially single stranded probes, wherein both the 5' and 3' ends of the surface probe are double stranded and the complementary positional domain is single stranded. The substrate may be treated with a polymerase enzyme to extend the 3' end of the universal domain oligonucleotide, in a template dependent manner, so as to synthesize the positional domain of the capture probe. The 3' end of the synthesized positional domain is then ligated, e.g. using a ligase enzyme, to the 5' end of the capture domain oligonucleotide to generate the capture probe. It will be understood in this regard that the 5' end of the capture domain oligonucleotide is phosphorylated to enable ligation to take place. As each species of surface probe comprises a unique complementary positional domain, each species of capture probe will comprise a unique positional domain.

It will be evident that in embodiments of the invention where the capture probe does not comprise a positional domain, the polymerase extension step described above may be omitted. Hence, the capture domain and universal domain may be allowed to hybridize to the complementary domains of the surface probes. Excess oligonucleotides may be removed by washing the substrate under standard hybridization conditions. The 3' end of the universal domain is then ligated, e.g. using a ligase enzyme, to the 5' end of the capture domain oligonucleotide to generate the capture probe.

The term "hybridisation" or "hybridises" as used herein refers to the formation of a duplex between nucleotide sequences which are sufficiently complementary to form duplexes via Watson-Crick base pairing. Two nucleotide sequences are "complementary" to one another when those molecules share base pair organization homology. "Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G and C of one sequence is then aligned with a T(U), A, C and G, respectively, of the other sequence. RNA sequences can also include complementary G=U or U=G base pairs. Thus, two sequences need not have perfect homology to be "complementary" under the invention. Usually two sequences are sufficiently complementary when at least about 90% (preferably at least about 95%) of the nucleotides share base pair organization over a defined length of the molecule. The domains of the capture and surface probes thus contain a region of complementarity. Furthermore the capture domain of the capture probe contains a region of complementarity for the nucleic acid, e.g. RNA (preferably mRNA), of the tissue sample.

The capture probe may also be synthesised on the substrate using polymerase extension (similarly to as described above) and a terminal transferase enzyme to add a "tail" which may constitute the capture domain. This is described further in Example 5 below. The use of terminal transferases to add nucleotide sequences to the end of an oligonucleotide is known in the art, e.g. to introduce a homopolymeric tail, e.g. a poly-T tail. Accordingly, in such a synthesis an oligonucleotide that corresponds to the universal domain of the capture probe may be contacted with the substrate and allowed to hybridize to the complementary domain of the surface probes. Excess oligonucleotides may be removed by washing the substrate under standard hybridization conditions. The resultant substrate comprises partially single stranded probes, wherein the 3' ends of the surface probes are double stranded and the complementary positional domain is single stranded. The substrate may be treated with a polymerase enzyme to extend the 3' end of the universal domain oligonucleotide, in a template dependent manner, so as to synthesize the positional domain of the capture probe. The capture domain, e.g. comprising a poly-T sequence, may then be introduced using a terminal transferase to add a poly-T tail to the positional domain to generate the capture probe. As described above, in embodiments where the capture probe does not comprise a positional domain, the polymerase extension step may be omitted and the capture domain may be introduced using a terminal transferase to add a poly-T tail to the universal domain to generate the capture probe.

The object substrate (often simply referred to as the "substrate") of, and for use in the methods of, the invention may contain multiple spots, or "features". Accordingly, in some embodiments of the invention the object substrate may be an array, i.e. an object substrate, e.g. slide or chip, on which the immobilized probes are arrayed on the surface of the substrate. A feature may be defined as an area or distinct position on the array substrate at which a single species of capture probe is immobilized. Hence each feature will comprise a multiplicity of probe molecules, of the same species. It will be understood in this context that whilst it is encompassed that each capture probe of the same species may have the same sequence, this need not necessarily be the case. Each species of capture probe may have the same positional domain (i.e. each member of a species and hence each probe in a feature may be identically "tagged"), but the sequence of each member of the feature (species) may differ, because the sequence of a capture domain may differ. As described above, random, degenerate or sequence specific capture domains may be used. Thus the capture probes within a feature may comprise different random or degenerate sequences. The number and density of the features on the substrate, e.g. array, will determine the resolution of the array, i.e. the level of detail at which the transcriptome of a tissue sample can be analysed. Hence, a higher density of features will typically increase the resolution of the array.

As discussed above, the size and number of the features on the substrate, e.g. array, of the invention will depend on the nature of the tissue sample and required resolution. Thus, if it is desirable to determine a transcriptome only for regions of cells within a tissue sample (or the sample contains large cells) then the number and/or density of features on the array may be reduced (i.e. lower than the possible maximum number of features) and/or the size of the features may be increased (i.e. the area of each feature may be greater than the smallest possible feature), e.g. an array comprising few large features. Alternatively, if it is desirable to determine a transcriptome of individual cells within a sample, it may be necessary to use the maximum number of features possible, which would necessitate using the smallest possible feature size, e.g. an array comprising many small features.

In some embodiments the capture probes immobilized on the substrate are not in an array format, i.e. the capture probes may be distributed uniformly on the substrate. In these embodiments, it is not necessary for the capture probes to comprise a positional domain, because the capture probes are not immobilized at specific positions on the substrate. However, the capture probes may comprise a universal domain.

By distributed uniformly on the substrate it is meant that the capture probes are immobilized on at least a portion of the substrate and there is an even amount of capture probe immobilized in any specific area in that portion, i.e. the mean amount of probe immobilized per unit area is consistent across the portion of substrate on which the probe is immobilized. The mean amount of probe immobilized per unit area may be controlled by the concentration of probe contacted with the substrate to immobilize the probe or the conditions used to immobilize the probe. For instance, when the capture probe is immobilized to the substrate indirectly, e.g. by hybridisation to a surface probe, the hybridisation and/or wash conditions may be modified such that not all of the surface probes are bound to a capture probe, i.e. in some embodiments not all of the surface probes are occupied by (i.e. bound to) a capture probe. Substrates on which the amount of probe immobilized per unit area is high will have a higher resolution.

A portion of the substrate may be at least 10% of the total substrate area. In some embodiments, a portion may be at least 20, 30, 40, 50, 60, 70, 80, 90, 95, 99 or 100% of the total substrate area. The portion of the substrate on which capture probes may be immobilized will be dependent on the size of the substrate and the size of the tissue sample to be contacted with the substrate. Advantageously, the area of the portion of the substrate on which probe is immobilized will be larger than the total area of the tissue sample. Preferably the area of the portion will be at least 1, 2, 3, 4 or 5% larger than the area of the tissue sample. In some embodiments the area of the portion will be least 10, 15, 20, 30, 40, 50% larger than the area of the tissue sample.

Whilst single cell resolution may be a preferred and advantageous feature of the present invention, it is not essential to achieve this, and resolution at the cell group level is also of interest, for example to detect or distinguish a particular cell type or tissue region, e.g. normal vs tumour cells.

In representative embodiments of the invention where the substrate is an array, the array may contain at least 2, 5, 10, 50, 100, 500, 750, 1000, 1500, 3000, 5000, 10000, 20000, 40000, 50000, 75000, 100000, 150000, 200000, 300000, 400000, 500000, 750000, 800000, 1000000, 1200000, 1500000, 1750000, 2000000, 2100000. 3000000, 3500000, 4000000, 4200000 or 4300000 features. Whilst 4300000 represents the maximum number of features presently available on a commercial array, it is envisaged that arrays with features in excess of this may be prepared and such arrays are of interest in the present invention. For instance, commercially available arrays allow for more than one array to be provided on a single substrate, e.g. slide or chip. Hence, the number of features on a substrate may be multiples of the above figures. For instance, the substrate, e.g. array, may comprise at least 8600000, 12900000 or 17200000 features. Given that array technology is continually developing, the array could contain even larger numbers of features, e.g. it has been postulated that is may be possible to include as many as $3.3 \times 10^9$ features on an array. As noted above, feature size may be decreased and this may allow greater numbers of features to be accommodated within the same or a similar area. By way of example these features may be comprised in an area of less than about 20 cm$^2$, 10 cm$^2$, 5 cm$^2$, 1 cm$^2$, 1 mm$^2$, or 100 µm$^2$.

Thus, in some embodiments of the invention the area of each feature may be from about 1 µm$^2$, 2 µm$^2$, 3 µm$^2$, 4 µm$^2$, 5 µm$^2$, 10 µm$^2$, 12 µm$^2$, 15 µm$^2$, 20 µm$^2$, 50 µm$^2$, 75 µm$^2$, 100 µm$^2$, 150 µm$^2$, 200 µm$^2$, 250 µm$^2$, 300 µm$^2$, 400 µm$^2$, or 500 µm$^2$. In some embodiments the area of a feature may be less than about 1 µm$^2$, e.g. less than 0.5, 0.4, 0.2 or 0.1 µm$^2$. In some embodiments, e.g. when the object substrate comprises a single feature, the feature (e.g. the area on which a capture probe is immobilized on the substrate with a homogeneous distribution, i.e. uniformly) may be from about 100 µm$^2$-20 cm$^2$, 1 mm$^2$-10 cm$^2$, 0.5 cm$^2$-5 cm$^2$, 0.6 cm$^2$-4 cm$^2$, 0.7 cm$^2$-3 cm$^2$, 0.8 cm$^2$-2 cm$^2$ or 0.9 cm$^2$-1 cm$^2$. e.g. at least about 0.5 cm$^2$, 0.6 cm$^2$, 0.7 cm$^2$, 0.8 cm$^2$, 0.9 cm$^2$, 1 cm$^2$, 2 cm$^2$, 3 cm$^2$, 4 cm$^2$ or 5 cm$^2$.

It will be evident that a tissue sample from any organism could be used in the methods of the invention, e.g. plant, animal or fungal. The substrate, e.g. array, of the invention allows the capture of any nucleic acid, e.g. mRNA molecules, which are present in cells that are capable of transcription and/or translation. The substrates, e.g. arrays, and methods of the invention are particularly suitable for isolating and analysing the transcriptome of cells within a sample, wherein spatial resolution of the transcriptomes is desirable, e.g. where the cells are interconnected or in contact directly with adjacent cells. However, it will be apparent to a person of skill in the art that the methods of the invention may also be useful for the analysis of the transcriptome of different cells or cell types within a sample even if said cells do not interact directly, e.g. a blood sample. In other words, the cells do not need to present in the context of a tissue and can be applied to the array as single cells (e.g. cells isolated from a non-fixed tissue). Such single cells, whilst not necessarily fixed to a certain position in a tissue, are nonetheless applied to a certain position on the substrate, e.g. array, and can be individually identified. Thus, in the context of analysing cells that do not interact directly, or are not present in a tissue context, the spatial properties of the described methods may be applied to obtaining or retrieving unique or independent transcriptome information from individual cells. Thus, a tissue sample may be defined as a sample of tissue comprising one or more cells. It may include a suspension of cells.

The sample may thus be a harvested or biopsied tissue sample, or possibly a cultured sample. Representative samples include clinical samples e.g. whole blood or blood-derived products, blood cells, tissues, biopsies, or cultured tissues or cells etc. including cell suspensions. In some embodiments, the sample may be enriched for one or more types of cell, e.g. specific types of blood cell or tumour cells. Techniques for cell isolation or enrichment are known in the art, and may include positive or negative selection based on expression of particular cell markers. Artificial tissues may for example be prepared from cell suspension (including for example blood cells). Cells may be captured in a matrix (for example a gel matrix e.g. agar, agarose, etc) and may then be sectioned in a conventional way. Such procedures are known in the art in the context of immunohistochemistry (see e.g. Andersson et al 2006, J. Histochem. Cytochem. 54(12): 1413-23. Epub 2006 Sep. 6).

The methods of the invention may find particular utility in the identification of tumour cells, especially transcriptionally active, e.g. metastatic, tumour cells or tumour cells with metastatic potential. In this respect, tumour cells may be found in blood. Whilst about 90% of the population of circulating tumour cells may show no or little gene activity, because apoptosis or necrosis pathways are activated in this population, the remaining 10% are transcriptionally active. At least some of the transcriptionally active cells are likely to give rise to metastasis and it would be useful to be able to identify these cells. Accordingly, the tissue sample may be a suspension of cells containing tumour cells (e.g. a sample of tumour cells isolated from a blood sample, or a blood sample in which the tumour cells have been enriched, or a biopsy or tissue sample, or tumour cells enriched from such a sample). The method may be performed as described above, wherein the detection of labelled cDNA will correlate to transcriptionally active, e.g. metastatic or potentially metastatic, tumour cells. Thus, in some embodiments the invention may be seen as providing a method for the identification of tumour cells, especially transcriptionally active, e.g. potentially metastatic, tumour cells.

The mode of tissue preparation and how the resulting sample is handled may affect the transcriptomic analysis of the methods of the invention. Moreover, various tissue samples will have different physical characteristics and it is well within the skill of a person in the art to perform the necessary manipulations to yield a tissue sample for use with the methods of the invention. However, it is evident from the disclosures herein that any method of sample preparation may be used to obtain a tissue sample that is suitable for use in the methods of the invention. For instance any layer of cells with a thickness of approximately 1 cell or less may be used in the methods of the invention. In one embodiment, the thickness of the tissue sample may be less than 0.9, 0.8, 0.7, 0.6, 0.5, 0.4, 0.3, 0.2 or 0.1 of the cross-section of a cell. However, since as noted above, the present invention is not limited to single cell resolution and hence it is not a requirement that the tissue sample has a thickness of one cell diameter or less; thicker tissue samples may, if desired, be used. For example cryostat sections may be used, which may be e.g. 10-20 μm thick.

The tissue sample may be prepared in any convenient or desired way and the invention is not restricted to any particular type of tissue preparation. Fresh, frozen, fixed or unfixed tissues may be used. Any desired convenient procedure may be used for fixing or embedding the tissue sample, as described and known in the art. Thus any known fixatives or embedding materials may be used.

As a first representative example of a tissue sample for use in the invention, the tissue may prepared by deep freezing at temperature suitable to maintain or preserve the integrity (i.e. the physical characteristics) of the tissue structure, e.g. less than −20° C. and preferably less than −25, −30, −40, −50, −60, −70 or −80° C. The frozen tissue sample may be sectioned, i.e. thinly sliced, onto the substrate surface by any suitable means. For example, the tissue sample may be prepared using a chilled microtome, a cryostat, set at a temperature suitable to maintain both the structural integrity of the tissue sample and the chemical properties of the nucleic acids in the sample, e.g. to less than −15° C. and preferably less than −20 or −25° C. Thus, the sample should be treated so as to minimize the degeneration or degradation of the nucleic acid, e.g. RNA in the tissue. Such conditions are well-established in the art and the extent of any degradation may be monitored through nucleic acid extraction, e.g. total RNA extraction and subsequent quality analysis at various stages of the preparation of the tissue sample.

In a second representative example, the tissue may be prepared using standard methods of formalin-fixation and paraffin-embedding (FFPE), which are well-established in the art. Following fixation of the tissue sample and embedding in a paraffin or resin block, the tissue samples may sectioned, i.e. thinly sliced, onto the substrate, e.g. array. As noted above, other fixatives and/or embedding materials can be used.

It will be apparent that the tissue sample section will need to be treated to remove the embedding material, e.g. to deparaffinize, i.e. to remove the paraffin or resin, from the sample prior to carrying out the methods of the invention. This may be achieved by any suitable method and the removal of paraffin or resin or other material from tissue samples is well established in the art, e.g. by incubating the sample (on the surface of the array) in an appropriate solvent e.g. xylene, e.g. twice for 10 minutes, followed by an ethanol rinse, e.g. 99.5% ethanol for 2 minutes, 96% ethanol for 2 minutes, and 70% ethanol for 2 minutes.

It will be evident to the skilled person that the RNA in tissue sections prepared using methods of FFPE or other methods of fixing and embedding is more likely to be partially degraded than in the case of frozen tissue. However, without wishing to be bound by any particular theory, it is believed that this may be advantageous in the methods of the invention. For instance, if the RNA in the sample is partially degraded the average length of the RNA polynucleotides will be less and more randomized than a non-degraded sample. It is postulated therefore that partially degraded RNA would result in less bias in the various processing steps, described elsewhere herein, e.g. ligation of adaptors (amplification domains), amplification of the cDNA molecules and sequencing thereof.

Hence, in one embodiment of the invention the tissue sample, i.e. the section of the tissue sample contacted with the substrate, e.g. array, is prepared using FFPE or other methods of fixing and embedding. In other words the sample may be fixed, e.g. fixed and embedded. In an alternative embodiment of the invention the tissue sample is prepared by deep-freezing. In another embodiment a touch imprint of a tissue may be used, according to procedures known in the art. In other embodiments an unfixed sample may be used.

The thickness of the tissue sample section for use in the methods of the invention may be dependent on the method used to prepare the sample and the physical characteristics of the tissue. Thus, any suitable section thickness may be used in the methods of the invention. In representative embodiments of the invention the thickness of the tissue sample section will be at least 0.1 μm, further preferably at least 0.2, 0.3, 0.4, 0.5, 0.7, 1.0, 1.5, 2, 3, 4, 5, 6, 7, 8, 9 or 10 μm. In other embodiments the thickness of the tissue sample section is at least 10, 12, 13, 14, 15, 20, 30, 40 or 50 μm. However, the thickness is not critical and these are representative values only. Thicker samples may be used if desired or convenient e.g. 70 or 100 μm or more. Typically, the thickness of the tissue sample section is between 1-100 μm, 1-50 μm, 1-30 μm, 1-25 μm, 1-20 μm, 1-15 μm, 1-10 μm, 2-8 μm, 3-7 μm or 4-6 μm, but as mentioned above thicker samples may be used.

On contact of the tissue sample section with the substrate, e.g. following removal of the embedding material e.g. deparaffinization, the nucleic acid, e.g. RNA, molecules in the tissue sample will bind to the immobilized capture probes on the substrate. In some embodiments it may be advantageous to facilitate the hybridization of the nucleic acid, e.g. RNA molecules to the capture probes. Typically, facilitating the hybridization comprises modifying the conditions under which hybridization occurs. The primary conditions that can be modified are the time and temperature of the incubation of the tissue section on the array prior to the reverse transcription step, which is described elsewhere herein.

It will be evident that tissue samples from different sources may require different treatments to allow the nucleic acids to interact with, i.e. hybridize to, the capture probes immobilized on the substrate. For instance, it may be useful to permeabilize the tissue sample to facilitate the transfer of nucleic acid to the substrate surface. If the tissue sample is not permeabilized sufficiently the amount of nucleic acid captured on the substrate may be too low to enable further analysis (see FIG. 2A), i.e. the signal from the labelled cDNA molecules may be of low intensity. Conversely, if the tissue sample is too permeable, the nucleic acid may diffuse away from its origin in the tissue sample. Hence, the nucleic acid may be captured on the substrate, but may not correlate accurately with its original spatial distribution in the tissue sample (see FIG. 2C), i.e. the signal from the labelled cDNA molecules may have low spatial resolution. Hence, there must be a balance between permeabilizing the tissue sample enough to obtain a good signal intensity whilst maintaining the spatial resolution of the nucleic acid distribution in the tissue sample (see FIG. 2B). The methods used to fix the tissue sample may also impact on the nucleic acid transfer from tissue sample to substrate.

Suitable methods and agents for permeabilizing and/or fixing cells and tissues are well known in the art and any appropriate method may be selected for use in the methods of the invention. In this respect, the methods of the invention may be used to determine the optimum conditions, e.g. the optimum combination of permeabilizing and/or fixative agents, for the capture of nucleic acids from a particular tissue sample. The inventors have found that some proteases are particularly useful in permeabilizing cells in a tissue sample, e.g. pepsin. Particularly useful fixatives include, e.g. methanol.

Thus, the methods and substrate of the invention are particularly useful for determining the optimum conditions for localised or spatial detection of the transcriptome of a tissue sample. In this respect, the step of labelling the cDNA generated on the substrate is particularly important because it enables the efficacy of the nucleic acid molecule capture to be assessed. Labelling the cDNA allows it to be detected, e.g. visualised, directly and the intensity and/or resolution of the detected signal can be quantified. The signal intensity and/or resolution may be compared with the signal obtained from cDNA generated on a substrate prepared using different methods, e.g. tissue permeabilization and/or fixation methods. The methods that result in the best signal intensity and/or resolution may be selected for use in future analyses and/or may be optimised further. The methods do not require the capture probes to comprise positional domains and/or universal domains (although the capture probes may comprise these domains in some embodiments). Furthermore, the capture probes do not need to be arrayed on the substrate (although the capture probes may be arrayed in some embodiments). Consequently, the methods and substrates of the invention are particularly advantageous because they can be performed cheaply and using commonly available instrumentation or apparatus. Once optimum conditions have been determined for capturing nucleic acid molecules on a substrate from a particularly type of tissue sample and/or tissue sample prepared using a particular method, the optimum conditions can be used to analyse similar tissue samples, wherein further analysis, such as sequence analysis may be performed. The methods of the invention therefore obviate the need to use expensive substrates to optimise the nucleic acid capture conditions, i.e. arrays comprising multiple species of immobilized capture probes, which contain positional and/or universal domains.

As conditions for localised or spatial detection of nucleic acid molecules from a tissue sample on a substrate vary depending on the tissue sample, a typical range of parameters is discussed herein. For instance, on contacting the tissue sample section with the substrate, e.g. an array, the substrate may be incubated for at least 1 hour to allow the nucleic acid, e.g. RNA, to hybridize to the capture probes. This may be particularly useful for FFPE tissue samples before the paraffin is removed. Preferably the substrate may be incubated for at least 2, 3, 5, 10, 12, 15, 20, 22 or 24 hours or until the tissue sample section has dried. In other embodiments, e.g. for FFPE tissue samples after the paraffin has been removed or fresh frozen tissue, the substrate may be incubated for less time, e.g. at least 5 minutes, e.g. at least 10, 15, 20, 25 or 30 minutes. The substrate incubation time is not critical and any convenient or desired time may be used. Typical substrate, e.g. array, incubations may be up to 72 hours. Thus, the incubation may occur at any suitable temperature, for instance at room temperature, although in a preferred embodiment the tissue sample section is incubated on the array at a temperature of at least 25, 26, 27, 28, 29, 30, 31, 32, 33, 34, 35, 36 or 37° C. Incubation temperatures of up to 55° C., e.g. 40, 45 or 50° C. are commonplace in the art. In a particularly preferred embodiment the tissue sample section is allowed to dry on the substrate, e.g. array, at 37° C. for 24 hours. In another preferred embodiment, the tissue sample section is allowed to dry on the substrate, e.g. array, at 50° C. for 15 minutes. It will be understood therefore that the precise conditions and methods for contacting the tissue sample with the array are not critical and may vary according to the nature of the sample and the fixation. Once the tissue sample section has dried the substrate may be stored at room temperature before performing the reverse transcription step. It will be understood that the if the tissue sample section is allowed to dry on the substrate surface, it will need to be rehydrated before further manipulation of the captured nucleic acid can be achieved, e.g. the step of reverse transcribing the captured RNA.

Hence, the method of the invention may comprise a further step of rehydrating the tissue sample after contacting the sample with the substrate, e.g. array.

In some embodiments, the tissue sample, e.g. tissue section, may be treated or modified prior to the step of contacting the tissue sample with the substrate and/or prior to generating the cDNA molecules on the substrate, e.g. to select one or more portions of the tissue sample for analysis. For instance, the tissue sample may be dissected to isolate one or more portions for analysis. Alternatively viewed, the tissue sample may be dissected to discard one or more portions for which analysis is not required. Any suitable method for dissecting the tissue sample may be utilised in the methods of the invention. In some embodiments, the tissue sample is dissected using laser capture microdissection (LCM). Accordingly, the method of the invention may comprise a step of dissecting the tissue sample. This aspect of the method comprise a step of retaining one or more portions of tissue sample for analysis and/or discarding one or more portions of tissue sample.

In a preferred aspect of the invention, the tissue sample may be dissected on the substrate. For instance, the tissue sample may be contacted with (e.g. fixed to) a LCM membrane. The LCM membrane:tissue sample composite may be further contacted with the object substrate to form a "sandwich", in which the tissue sample is the central layer in the sandwich. One or more portions of the tissue sample may be dissected using a laser, wherein the one or more portions of the tissue sample that are not required for analysis are removed from the substrate (e.g. peeled off along with the LCM membrane) and optionally discarded. The LCM membrane may be removed from the remaining one or more portions of tissue sample on the substrate and the method of the invention may be performed as described herein. In some embodiments, the one or more portions of tissue sample removed from the substrate may be used for analysis. Thus, in some embodiments capture probes may be immobilized on the surface of the LCM membrane and/or the substrate. Alternatively viewed, the LCM membrane may be an object substrate as described herein. Thus, the step of dissecting the tissue sample may comprise contacting the tissue sample with more than one substrate, wherein RNA is captured from one or more portions of the tissue sample on each substrate.

In some embodiments it may be advantageous to block (e.g. mask or modify) the capture probes prior to contacting the tissue sample with the substrate, particularly when the nucleic acid in the tissue sample, or the tissue sample itself, is subject to a process of modification prior to its capture on the substrate. Specifically, it may be advantageous to block or modify the free 3' end of the capture probe. It may be necessary to block or modify the capture probes, particularly the free 3' end of the capture probe, prior to contacting the tissue sample with the substrate to avoid modification of the capture probes, e.g. to avoid the removal or modification of the free 3' OH group on the end of the capture probes. Preferably the incorporation of a blocking domain may be incorporated into the capture probe when it is synthesised. However, the blocking domain may be incorporated to the capture probe after its synthesis.

In some embodiments the capture probes may be blocked by any suitable and reversible means that would prevent modification of the capture domains during the process of modifying the nucleic acid and/or the tissue sample, which occurs after the tissue sample has been contacted with the substrate. In other words, the capture probes may be reversibly masked or modified such that the capture domain of the capture probe does not comprise a free 3' end, i.e. such that the 3' end is removed or modified, or made inaccessible so that the capture probe is not susceptible to the process or reaction which is used to modify the nucleic acid and/or the tissue sample. Alternatively, if the capture probes are not blocked prior to the process or reaction used to modify the nucleic acid and/or tissue sample, capture probe may be modified after the process or reaction to reveal and/or restore the 3' end of the capture domain of the capture probe.

For example, blocking probes may be hybridised to the capture probes to mask the free 3' end of the capture domain, e.g. hairpin probes or partially double stranded probes, suitable examples of which are known in the art. The free 3' end of the capture domain may be blocked by chemical modification, e.g. addition of an azidomethyl group as a chemically reversible capping moiety such that the capture probes do not comprise a free 3' end. Suitable alternative capping moieties are well known in the art, e.g. the terminal nucleotide of the capture domain could be a reversible terminator nucleotide, which could be included in the capture probe during or after probe synthesis.

Alternatively or additionally, the capture domain of the capture probe could be modified so as to allow the removal of any modifications of the capture probe, e.g. additional nucleotides, that occur when the nucleic acid molecules and/or the tissue sample are modified. For instance, the capture probes may comprise an additional sequence downstream of the capture domain, i.e. 3' to capture domain, namely a blocking domain. This could be in the form of, e.g. a restriction endonuclease recognition sequence or a sequence of nucleotides cleavable by specific enzyme activities, e.g. uracil. Following the modification of the nucleic acid and/or the tissue sample, the capture probes could be subjected to an enzymatic cleavage, which would allow the removal of the blocking domain and any of the additional nucleotides that are added to the 3' end of the capture probe during the modification process. The removal of the blocking domain would reveal and/or restore the free 3' end of the capture domain of the capture probe. The blocking domain could be synthesised as part of the capture probe or could be added to the capture probe in situ (i.e. as a modification of an existing substrate), e.g. by ligation of the blocking domain.

The capture probes may be blocked using any combination of the blocking mechanisms described above.

Once the nucleic acid and/or tissue sample has been modified or processed to enable the nucleic acid to hybridise to the capture domain of the capture probe, the capture probe must be unblocked, e.g. by dissociation of the blocking oligonucleotide, removal of the capping moiety and/or blocking domain.

In order to correlate the transcriptome information, e.g. signal intensity and/or resolution of the labelled cDNA, sequence analysis etc., obtained from the substrate, e.g. by imaging the substrate and/or sequence analysis of the immobilized cDNA at one or more features of the array, with the region (i.e. an area or cell) of the tissue sample the tissue sample is oriented in relation to the immobilized probes on the substrate, e.g. oriented in relation to the features on the array. In other words, the tissue sample is placed on the substrate, e.g. array, such that the position of a capture probe on the substrate, e.g. array, may be correlated with a position in the tissue sample. Thus it may be identified where in the tissue sample the position of each species of capture probe (or each feature of the array) corresponds. In other words, it may be identified to which location in the tissue sample the position of each species of capture probe corresponds. This may be done by virtue of positional markers present on the array, as described below.

Conveniently, but not necessarily, the tissue sample may be imaged following its contact with the array. This may be performed before or after the nucleic acid of the tissue sample is processed, e.g. before or after the cDNA generation step of the method, in particular the step of generating the first strand cDNA by reverse transcription. In some embodiments, the tissue sample is imaged before the immobilized cDNA is labelled. However, the tissue sample may be imaged at the same time as the labelled cDNA is imaged. In embodiments in which the cDNA is released from the surface of the substrate, the tissue sample may be imaged prior to the release of the captured and synthesised (i.e. extended) cDNA from the substrate, e.g. array. In a particularly preferred embodiment the tissue is imaged after the nucleic acid of the tissue sample has been processed, e.g. after the reverse transcription step, and any residual tissue is removed (e.g. washed) from the array prior to detecting, e.g. imaging, the labelled cDNA and/or the release of molecules from the substrate, e.g. array. In some embodiments, the step of processing the captured nucleic acid, e.g. the reverse transcription step, may act to remove residual tissue from the array surface, e.g. when using tissue preparing by deep-freezing. In such a case, imaging of the tissue sample may take place prior to the processing step, e.g. the cDNA synthesis step. Generally speaking, imaging may take place at any time after contacting the tissue sample with the substrate, but before any step which degrades or removes the tissue sample. As noted above, this may depend on the tissue sample.

Advantageously, the substrate, e.g. array, may comprise markers to facilitate the orientation of the tissue sample or the image thereof in relation to the immobilized capture probes on the substrate, e.g. the features of the array. Any suitable means for marking the array may be used such that they are detectable when the tissue sample is imaged. For instance, a molecule, e.g. a fluorescent molecule, that generates a signal, preferably a visible signal, may be immobilized directly or indirectly on the surface of the array. Preferably, the array comprises at least two markers in distinct positions on the surface of the substrate, further preferably at least 3, 4, 5, 6, 7, 8, 9, 10, 12, 15, 20, 30, 40, 50, 60, 70, 80, 90 or 100 markers. Conveniently several hundred or even several thousand markers may be used. In some embodiments, tens of thousands of markers may be used. The markers may be provided in a pattern, for example the markers may make up an outer edge of the portion of the substrate on which the capture probes are immobilized, e.g. the markers may be a row of features on the outer border of the portion on which the capture probes are immobilized on the substrate, e.g. an entire outer row of features on an array. Other informative patterns may be used, e.g. lines sectioning the array. This may facilitate aligning an image of the tissue sample to the signal detected from the labelled cDNA molecules, (e.g. the image of the labelled cDNA molecules) i.e. to the portion on which the capture probes are immobilized on the substrate, e.g. an array, or indeed generally in correlating the features of the array to the tissue sample. Thus, the marker may be an immobilized molecule to which a signal giving molecule may interact to generate a signal. In a representative example, the substrate, e.g. array, may comprise a marker feature, e.g. a nucleic acid probe immobilized on the substrate to which a labelled nucleic acid may hybridize. For instance, a labelled nucleic acid molecule, or marker nucleic acid, may be linked or coupled to a chemical moiety capable of fluorescing when subjected to light of a specific wavelength (or range of wavelengths), i.e. excited. Such a marker nucleic acid molecule may be contacted with the array before, contemporaneously with or after the tissue sample is stained in order to visualize or image the tissue sample. However, the marker must be detectable when the tissue sample is imaged. Thus, in a preferred embodiment the marker may be detected using the same imaging conditions used to visualize the tissue sample. Furthermore, it is advantageous that the marker is detectable when the labelled cDNA is detected, e.g. imaged. Hence, in some embodiments the marker may be detected using the same conditions e.g. imaging conditions, used to detect the signal from the labelled cDNA.

In a particularly preferred embodiment of the invention, the substrate, e.g. array, comprises marker features to which a labelled, preferably fluorescently labelled, marker nucleic acid molecule, e.g. oligonucleotide, is hybridized.

The step of detecting, e.g. imaging, the labelled cDNA may use any convenient means known in the art, but typically will comprise microscopy e.g. light, bright field, dark field, phase contrast, fluorescence, reflection, interference, confocal microscopy or a combination thereof. However, the method used will be dependent on the method used to label the cDNA synthesized on the surface of the substrate. Numerous methods for labelling nucleic acid molecules, both single stranded and double stranded molecules are known in the art. The label must result in a visibly detectable signal. Whilst the label does not have to be directly signal giving, this is preferred as it reduces the number of processing steps require to generate a signal. If several steps are required to generate a signal from the labelled cDNA, the resulting signal may be inconsistent, i.e. signals from different areas of the substrate may be non-uniform.

A directly detectable label is one that can be directly detected without the use of additional reagents, while an indirectly detectable label is one that is detectable by employing one or more additional reagents, e.g., where the label is a member of a signal producing system made up of two or more components. In many embodiments, the label is a directly detectable label, where directly detectable labels of interest include, but are not limited to: fluorescent labels, coloured labels, radioisotopic labels, chemiluminescent labels, and the like. Any spectrophotometrically or optically-detectable label may be used. In other embodiments the label may provide a signal indirectly, i.e. it may require the addition of further components to generate signal. For instance, the label may be capable of binding a molecule that is conjugated to a signal giving molecule.

The label is incorporated into the synthesized part of the cDNA molecules, i.e. as part of the synthesized molecules, e.g. a labelled nucleotide, or binds to the newly synthesized part of the nucleic acid molecule. Hence, the capture probe, or a part thereof (such as a positional or universal domain), is not a label for the purpose of this aspect of the invention. The function of the label is to indicate areas on the substrate at which transcript has been captured and cDNA has been synthesized. Accordingly, a capture probe, or part thereof, cannot achieve this function as its presence on the surface of the substrate is not conditional on the presence of transcript captured on the surface of the substrate.

In preferred embodiments, the cDNA is labelled by the incorporation of a labelled nucleotide when the cDNA is synthesized. The labelled nucleotide may be incorporated in the first and/or second strand synthesis. In a particularly preferred embodiment, the labelled nucleotide is a fluorescently labelled nucleotide. Thus, the labelled cDNA may be imaged by fluorescence microscopy. Whilst fluorescent labels require excitation to provide a detectable signal, as the source of excitation is derived from the instrument/apparatus used to detect the signal, fluorescent labels may be viewed as directly signal giving labels. Fluorescent molecules that may be used to label nucleotides are well known in the art, e.g. fluorescein, the cyanine dyes, such as Cy3, Cy5, Alexa 555, Bodipy 630/650, and the like. Other labels, such as those described below, may also be employed as are known in the art. In preferred embodiments fluorescently tagged CTP (such as Cy3-CTP, Cy5-CTP) is incorporated into the cDNA molecules synthesized on the surface of the array.

As mentioned above, labels may be incorporated into the synthesized cDNA by binding to the molecules, e.g., via intercalation. Representative detectable molecules that may find use in such embodiments include fluorescent nucleic acid stains, such as phenanthridinium dyes, including monomers or homo- or heterodimers thereof, that give an enhanced fluorescence when complexed with nucleic acids. Examples of phenanthridinium dyes include ethidium homodimer, ethidium bromide, propidium iodide, and other alkyl-substituted phenanthridinium dyes. In another embodiment of the invention, the nucleic acid stain is or incorporates an acridine dye, or a homo- or heterodimer thereof, such as acridine orange, acridine homodimer, ethidium-acridine heterodimer, or 9-amino-6-chloro-2-methoxyacridine. In yet another embodiment of the invention, the nucleic acid stain is an indole or imidazole dye, such as Hoechst 33258, Hoechst 33342, Hoechst 34580 (BIOPROBES 34, Molecular Probes, Inc. Eugene, Oreg., (May 2000)) DAPI (4',6-diamidino-2-phenylindole) or DIPI (4',6-(diimidazolin-2-yl)-2-phenylindole). Other permitted nucleic acid stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating $Tb^{3+}$ and $Eu^{3+}$, for example). In certain embodiments of the invention, the nucleic acid stain is a cyanine dye or a homo- or heterodimer of a cyanine dye that gives an enhanced fluorescence when associated with nucleic acids. Any of the dyes described in U.S. Pat. No. 4,883,867 to Lee (1989), U.S. Pat. No. 5,582,977 to Yue et al. (1996), U.S. Pat. No. 5,321,130 to Yue et al. (1994), and U.S. Pat. No. 5,410,030 to Yue et al. (1995) (all four patents incorporated by reference) may be used, including nucleic acid stains commercially available under the trademarks TOTO, BOBO, POPO, YOYO, TO-PRO, BO-PRO, PO-PRO and YO-PRO from Molecular Probes, Inc., Eugene, Oreg. Any of the dyes described in U.S. Pat. No. 5,436,134 to Haugland et al. (1995), U.S. Pat. No. 5,658,751 to Yue et al. (1997), and U.S. Pat. No. 5,863,753 to Haugland et al. (1999) (all three patents incorporated by reference) may be used, including nucleic acid stains commercially available under the trademarks SYBR Green, SYBR Gold, EvaGreen, SYTO, SYTOX, PICOGREEN, OLIGREEN, and RIBOGREEN from Molecular Probes, Inc., Eugene, Oreg. In yet other embodiments of the invention, the nucleic acid stain is a monomeric, homodimeric or heterodimeric cyanine dye that incorporates an aza- or polyazabenzazolium heterocycle, such as an azabenzoxazole, azabenzimidazole, or azabenzothiazole, that gives an enhanced fluorescence when associated with nucleic acids, including nucleic acid stains commercially available under the trademarks SYTO, SYTOX, JOJO, JO-PRO, LOLO, LO-PRO from Molecular Probes, Inc., Eugene, Oreg. The type of nucleic acid stain may be selected based on its capacity to bind to single or double stranded nucleic acid. In embodiments where the first cDNA strand is labelled, it may be preferable to use nucleic acid stains capable of labelling single stranded nucleic acid molecules as the RNA transcript captured on the substrate and used to template cDNA synthesis may be partially or fully degraded.

In a particularly advantageous embodiment of the invention, the methods may include a step of removing a portion of the nucleic acid molecules immobilized on the surface of the substrate. This step may be particularly advantageous for analysing the transcriptome of part or portion of a tissue sample, e.g. an area of interest, particular cell or tissue type etc. Removing nucleic acid molecules immobilized on the surface of the substrate that are not of interest may reduce costs and/or time required for further analysis steps. Fewer reagents are needed to perform sequence analysis on cDNA molecules from a portion of the tissue sample in comparison to the reagents required to perform sequence analysis on cDNA molecules from the whole of the tissue sample. Correspondingly, less sequence analysis is required for cDNA molecules from a portion of the tissue sample. A further benefit derived from removing a portion of the nucleic acid molecules from the surface of the substrate is that it is not necessary to include a positional domain in the capture probe to correlate the sequence analysis with a position in the tissue sample. In this respect, because cDNA molecules that are not of interest (i.e. from areas of the tissue sample that are not of interest) have been removed from the substrate, the sequences analysed will have been derived from the specific area of the tissue sample that correlates to the portion of cDNA molecules that were not removed from the substrate. Accordingly, it is not necessary to immobilize the capture probes on the substrate in the form of an array. However, in many embodiments of the invention, the capture probes comprise a positional domain and/or are immobilized on the substrate in an array format, i.e. the substrate is an array.

The signal obtained from the step of detecting, e.g. imaging, the labelled cDNA molecules enables areas of the tissue sample to be selected for further analysis. In its simplest form, a single discrete portion of the immobilized cDNA on the substrate (corresponding to a portion of the tissue sample) may be selected for further analysis and all other immobilized nucleic acid molecules on the surface of the substrate may be removed. It will evident that more than one portion may be selected for further analysis, e.g. 2, 3, 4, 5, 6, 7, 8, 9, 10 or more portions. In some embodiments 15, 20, 25, 30, 40, 50 or more portions may be selected. Accordingly, cDNA molecules from one or more portions may be selected for removal, e.g. 2, 3, 4, 5, 6, 7, 8, 9, 10 or more portions. In some embodiments 15, 20, 25, 30, 40, 50 or more portions may be selected. In some embodiments, the portions selected for further analysis (or removal) may be based cell or tissue types, by reference an image of the tissue sample and correlating the position in the tissue sample with the position on the substrate. In still further embodiments, the portions selected for further analysis (or removal) may be based on the amount of cDNA immobilized in a particular area. For instance, portions of the substrate in which the intensity of the signal from the immobilized labelled cDNA molecules is above and/or below specific threshold limits may be targeted for removal (or further analysis). Hence, portions on the substrate that correlate to parts of the tissue sample with high levels of transcription may be removed to enrich the proportion of the transcriptome analysed for parts of the tissue sample with moderate or low levels of transcription. Similarly, the analysis may be focussed on parts of the tissue sample with high levels of transcription.

The step of removing a portion of the nucleic acid molecules immobilized on the surface of the substrate may be achieved using any convenient means. In some embodiments the immobilized cDNA molecules may be removed by laser ablation, e.g. the portion(s) of the substrate from which the cDNA molecules are to be removed may be identified by detecting, e.g. imaging, the labelled cDNA molecules and those areas subjected to treatment with a laser that is sufficient to remove the cDNA molecules from the surface of the substrate. Advantageously, the laser ablation may also remove the tissue sample from the targeted areas. In some embodiments the tissue sample may be removed from the substrate, as described elsewhere herein, prior to the removal of a portion the immobilized cDNA molecules. Suitable instruments and apparatus for removing cDNA molecules from the surface of an array are known in the art, e.g. a MMI Cell cut instrument (Molecular Machines and Industries AG, Glattburg, Switzerland). Other means for removing cDNA molecules from the surface of the substrate may include cleavage, e.g. enzymatic cleavage. For instance, the portion(s) of the substrate for further analysis may be masked (e.g. using standard array mask apparatus) and the non-masked areas of the substrate subjected to a cleavage agent, e.g. an enzyme, to release the capture probes (and attached cDNA molecules) from the surface of the substrate, as described above. The portion of the substrate selected for further analysis may be unmasked and subsequent analysis performed according to the remaining method steps described herein.

The step of imaging the tissue may use any convenient histological means known in the art, e.g. light, bright field, dark field, phase contrast, fluorescence, reflection, interference, confocal microscopy or a combination thereof. Typically the tissue sample is stained prior to visualization to provide contrast between the different regions, e.g. cells, of the tissue sample. The type of stain used will be dependent on the type of tissue and the region of the cells to be stained. Such staining protocols are known in the art. In some embodiments more than one stain may be used to visualize (image) different aspects of the tissue sample, e.g. different regions of the tissue sample, specific cell structures (e.g. organelles) or different cell types. In other embodiments, the tissue sample may be visualized or imaged without staining the sample, e.g. if the tissue sample contains already pigments that provide sufficient contrast or if particular forms of microscopy are used.

In a preferred embodiment, the tissue sample is visualized or imaged using fluorescence microscopy. Accordingly, in some embodiments, the tissue sample and the labelled cDNA may be visualized or imaged at the same time or sequentially using the same imaging apparatus.

The tissue sample, i.e. any residual tissue that remains in contact with the substrate following the reverse transcription step and detecting, e.g. imaging, the labelled cDNA, and optionally imaging the tissue sample if imaging the tissue sample is desired and was not carried out before reverse transcription, preferably is removed prior to the step of releasing the cDNA molecules from the substrate. Thus, the methods of the invention may comprise a step of washing the substrate. Removal of the residual tissue sample may be performed using any suitable means and will be dependent on the tissue sample. In the simplest embodiment, the substrate may be washed with water. The water may contain various additives, e.g. surfactants (e.g. detergents), enzymes etc to facilitate to removal of the tissue. In some embodiments, the substrate is washed with a solution comprising a proteinase enzyme (and suitable buffer) e.g. proteinase K. In other embodiments, the solution may comprise also or alternatively cellulase, hemicellulase or chitinase enzymes, e.g. if the tissue sample is from a plant or fungal source. In further embodiments, the temperature of the solution used to wash the substrate may be, e.g. at least 30° C., preferably at least 35, 40, 45, 50 or 55° C. It will be evident that the wash solution should minimize the disruption of the immobilized nucleic acid molecules. For instance, in some embodiments the nucleic acid molecules may be immobilized on the substrate indirectly, e.g. via hybridization of the capture probe and the RNA and/or the capture probe and the surface probe, thus the wash step should not interfere with the interaction between the molecules immobilized on the substrate, i.e. should not cause the nucleic acid molecules to be denatured.

Following the step of contacting the substrate with a tissue sample, under conditions sufficient to allow hybridization to occur between the nucleic acid, e.g. RNA (preferably mRNA), of the tissue sample to the capture probes, the step of securing (acquiring) the hybridized nucleic acid takes place. Securing or acquiring the captured nucleic acid involves extending the capture probe to produce a copy of the captured nucleic acid, e.g. generating cDNA from the captured (hybridized) RNA. It will be understood that this refers to the synthesis of a complementary strand of the hybridized nucleic acid, e.g. generating cDNA based on the captured RNA template (the RNA hybridized to the capture domain of the capture probe). Thus, in an initial step of extending the capture probe, e.g. the cDNA generation, the captured (hybridized) nucleic acid, e.g. RNA acts as a template for the extension, e.g. reverse transcription, step. In some embodiments, securing or acquiring the capture nucleic acid may be viewed as tagging or marking the captured nucleic acid with the positional domain specific to the feature on which the nucleic acid is captured. In many embodiments, the step of securing or acquiring the captured nucleic acid involves the directly incorporating a signal giving label into the synthesized copy of the captured nucleic acid molecule.

Reverse transcription concerns the step of synthesizing cDNA (complementary or copy DNA) from RNA, preferably mRNA (messenger RNA), by reverse transcriptase. Thus cDNA can be considered to be a copy of the RNA present in a cell at the time at which the tissue sample was taken, i.e. it represents all or some of the genes that were expressed in said cell at the time of isolation.

The capture probe, specifically the capture domain of the capture probe, acts as a primer for producing the complementary strand of the nucleic acid hybridized to the capture probe, e.g. a primer for reverse transcription. Hence, the nucleic acid, e.g. cDNA, molecules generated by the extension reaction, e.g. reverse transcription reaction, incorporate the sequence of the capture probe, i.e. the extension reaction, e.g. reverse transcription reaction. Advantageously the molecules generated by the extension reaction incorporate directly a label such that the amount of transcript in the tissue sample that is in contact with the substrate may be determined, e.g. by measuring the intensity of the signal generated by the label. As mentioned above, in some embodiments each species of capture probe may comprise a positional domain (feature identification tag) that represents a unique sequence for each feature of the array. Thus, in some embodiments all of the nucleic acid, e.g. cDNA, molecules synthesized at a specific feature will comprise the same nucleic acid "tag".

The nucleic acid, e.g. cDNA, molecules synthesized at a specific position or area on the surface of the substrate, e.g. each feature of an array, may represent the genes expressed from the region or area of the tissue sample in contact with that position or area, e.g. feature. For instance, a tissue or cell type or group or sub-group thereof, and may further represent genes expressed under specific conditions, e.g. at a particular time, in a specific environment, at a stage of development or in response to stimulus etc. Hence, the cDNA at any single position or area, e.g. feature, may represent the genes expressed in a single cell, or if the position or area, e.g. feature, is in contact with the sample at a cell junction, the cDNA may represent the genes expressed in more than one cell. Similarly, if a single cell is in contact with a large area of the substrate, e.g. multiple features, then each position within the area, e.g. each feature, may represent a proportion of the genes expressed in said cell.

The step of extending the capture probe, e.g. reverse transcription, may be performed using any suitable enzymes and protocol of which many exist in the art, as described in detail below. However, it will be evident that it is not necessary to provide a primer for the synthesis of the first nucleic acid, e.g. cDNA, strand because the capture domain of the capture probe acts as the primer, e.g. reverse transcription primer.

Preferably, in the context of the present invention the secured nucleic acid (i.e. the nucleic acid covalently attached to the capture probe), e.g. cDNA, is treated to comprise double stranded DNA. Treatment of the captured nucleic acid to produce double stranded DNA may be achieved in a single reaction to generate only a second DNA, e.g. cDNA, strand, i.e. to produce double stranded DNA molecules without increasing the number of double stranded DNA molecules, or in an amplification reaction to generate multiple copies of the second strand, which may be in the form of single stranded DNA (e.g. linear amplification) or double stranded DNA, e.g. cDNA (e.g. exponential amplification).

The step of second strand DNA, e.g. cDNA, synthesis may take place in situ on the substrate, either as a discrete step of second strand synthesis, for example using random primers as described in more detail below, or in the initial step of an amplification reaction. Alternatively, the first strand DNA, e.g. cDNA (the strand comprising, i.e. incorporating, the capture probe) may be released from the array and second strand synthesis, whether as a discrete step or in an amplification reaction may occur subsequently, e.g. in a reaction carried out in solution.

Where second strand synthesis takes place on the substrate (i.e. in situ) the method may include an optional step of removing the captured nucleic acid, e.g. RNA, before the second strand synthesis, for example using an RNA digesting enzyme (RNase) e.g. RNase H. Procedures for this are well known and described in the art. However, this is generally not necessary, and in most cases the RNA degrades naturally. Removal of the tissue sample from the array will generally remove the RNA from the array. RNase H can be used if desired to increase the robustness of RNA removal. RNA removal may be useful in embodiments where the cDNA is labelled after it has been generated, e.g. labelled with a nucleic acid stain. Removal of the RNA may provide a consistent target to which the nucleic acid stain can interact (bind), i.e. all of the immobilized molecules will be single stranded after RNA removal. Prior to a step of RNA removal, the immobilized molecules may be a mixture of fully or partially double stranded molecules (RNA:DNA hybrids) and single stranded molecules (where the RNA has already degraded). Some nucleic acid stains may provide a stronger signal when interacting with double stranded nucleic acid, when compared to the signal from single stranded nucleic acid. Thus, it is preferable when using a nucleic acid stain to label the immobilised cDNA that the molecules are either all fully single stranded or double stranded.

In tissue samples that comprise large amounts of RNA, the step of generating the double stranded cDNA may yield a sufficient amount of cDNA that it may be sequenced directly (following release from the substrate). In this case, second strand cDNA synthesis may be achieved by any means known in the art and as described below. The second strand synthesis reaction may be performed on the substrate directly, i.e. whilst the cDNA is immobilized on the substrate, or preferably after the cDNA has been released from the substrate, as described below.

In other embodiments it will be necessary to enhance, i.e. amplify, the amount of secured nucleic acid, e.g. synthesized cDNA, to yield quantities that are sufficient for DNA sequencing. In this embodiment, the first strand of the secured nucleic acid, e.g. cDNA molecules, which comprise also the capture probe of the substrate, acts as a template for the amplification reaction, e.g. a polymerase chain reaction. The first reaction product of the amplification will be a second strand of DNA, e.g. cDNA, which itself will act as a template for further cycles of the amplification reaction.

In either of the above described embodiments, the second strand of DNA, e.g. cDNA, will comprise a complement of the capture probe. If the capture probe comprises a universal domain, and particularly an amplification domain within the universal domain, then this may be used for the subsequent amplification of the DNA, e.g. cDNA, e.g. the amplification reaction may comprise a primer with the same sequence as the amplification domain, i.e. a primer that is complementary (i.e. hybridizes) to the complement of the amplification domain. In view of the fact that the amplification domain is upstream of the positional domain (if present) of the capture probe (in the secured nucleic acid, e.g. the first cDNA strand), the complement of the positional domain (if the position domain is present in the capture probe) will be incorporated in the second strand of the DNA, e.g. cDNA molecules.

In embodiments where the second strand of DNA, e.g. cDNA, is generated in a single reaction, the second strand synthesis may be achieved by any suitable means. For instance, the first strand cDNA, preferably, but not necessarily, released from the substrate, may be incubated with random primers, e.g. hexamer primers, and a DNA polymerase, preferably a strand displacement polymerase, e.g. klenow (exo⁻), under conditions sufficient for templated DNA synthesis to occur. This process will yield double stranded cDNA molecules of varying lengths and is unlikely to yield full-length cDNA molecules, i.e. cDNA molecules that correspond to entire mRNA from which they were synthesized. The random primers will hybridise to the first strand cDNA molecules at a random position, i.e. within the sequence rather than at the end of the sequence.

If it is desirable to generate full-length DNA, e.g. cDNA, molecules, i.e. molecules that correspond to the whole of the captured nucleic acid, e.g. RNA molecule (if the nucleic acid, e.g. RNA, was partially degraded in the tissue sample then the captured nucleic acid, e.g. RNA, molecules will not be "full-length" transcripts), then the 3' end of the secured nucleic acid, e.g. first stand cDNA, molecules may be modified. For example, a linker or adaptor may be ligated to the 3' end of the cDNA molecules. This may be achieved using single stranded ligation enzymes such as T4 RNA ligase or Circligase™ (Epicentre Biotechnologies).

Alternatively, a helper probe (a partially double stranded DNA molecule capable of hybridising to the 3' end of the first strand cDNA molecule), may be ligated to the 3' end of the secured nucleic acid, e.g. first strand cDNA, molecule using a double stranded ligation enzyme such as T4 DNA ligase. Other enzymes appropriate for the ligation step are known in the art and include, e.g. Tth DNA ligase, Taq DNA ligase, *Thermococcus* sp. (strain 9° N) DNA ligase (9° N™ DNA ligase, New England Biolabs), and Ampligase™ (Epicentre Biotechnologies). The helper probe comprises also a specific sequence from which the second strand DNA, e.g. cDNA, synthesis may be primed using a primer that is complementary to the part of the helper probe that is ligated to the secured nucleic acid, e.g. first cDNA strand. A further alternative comprises the use of a terminal transferase active enzyme to incorporate a polynucleotide tail, e.g. a poly-A tail, at the 3' end of the secured nucleic acid, e.g. first strand of cDNA, molecules. The second strand synthesis may be primed using a poly-T primer, which may also comprise a specific amplification domain for further amplification. Other methods for generating "full-length" double stranded DNA, e.g. cDNA, molecules (or maximal length second strand synthesis) are well-established in the art.

In some embodiments, second strand synthesis may use a method of template switching, e.g. using the SMART™ technology from Clontech®. SMART (Switching Mechanism at 5' End of RNA Template) technology is well established in the art and is based that the discovery that reverse transcriptase enzymes, e.g. Superscript® II (Invitrogen), are capable of adding a few nucleotides at the 3' end of an extended cDNA molecule, i.e. to produce a DNA/RNA hybrid with a single stranded DNA overhang at the 3' end. The DNA overhang may provide a target sequence to which an oligonucleotide probe can hybridise to provide an additional template for further extension of the cDNA molecule. Advantageously, the oligonucleotide probe that hybridises to the cDNA overhang contains an amplification domain sequence, the complement of which is incorporated into the synthesised first strand cDNA product. Primers containing the amplification domain sequence, which will hybridise to the complementary amplification domain sequence incorporated into the cDNA first strand, can be added to the reaction mix to prime second strand synthesis using a suitable polymerase enzyme and the cDNA first strand as a template. This method avoids the need to ligate adaptors to the 3' end of the cDNA first strand. Whilst template switching was originally developed for full-length mRNAs, which have a 5' cap structure, it has since been demonstrated to work equally well with truncated mRNAs without the cap structure. Thus, template switching may be used in the methods of the invention to generate full length and/or partial or truncated cDNA molecules. Thus, in a preferred embodiment of the invention, the second strand synthesis may utilise, or be achieved by, template switching. In a particularly preferred embodiment, the template switching reaction, i.e. the further extension of the cDNA first strand to incorporate the complementary amplification domain, is performed in situ (whilst the capture probe is still attached, directly or indirectly, to the substrate, e.g. array). Preferably, the second strand synthesis reaction is also performed in situ.

As mentioned above, in some embodiments the immobilized cDNA may be labelled by incorporating label into the second strand of the cDNA, e.g. incorporating labelled nucleotides into the cDNA second strand. This may be in addition to, or as an alternative to, incorporating labelled nucleotides into the first cDNA strand.

In embodiments where it may be necessary or advantageous to enhance, enrich or amplify the DNA, e.g. cDNA, molecules, amplification domains may be incorporated in the DNA, e.g. cDNA, molecules. As discussed above, a first amplification domain may be incorporated into the secured nucleic acid molecules, e.g. the first strand of the cDNA molecules, when the capture probe comprises a universal domain comprising an amplification domain. In these embodiments, the second strand synthesis may incorporate a second amplification domain. For example, the primers used to generate the second strand cDNA, e.g. random hexamer primers, poly-T primer, the primer that is complementary to the helper probe, may comprise at their 5' end an amplification domain, i.e. a nucleotide sequence to which an amplification primer may hybridize. Thus, the resultant double stranded DNA may comprise an amplification domain at or towards each 5' end of the double stranded DNA, e.g. cDNA, molecules. These amplification domains may be used as targets for primers used in an amplification reaction, e.g. PCR. Alternatively, the linker or adaptor which is ligated to the 3' end of the secured nucleic acid molecules, e.g. first strand cDNA molecules, may comprise a second universal domain comprising a second amplification domain. Similarly, a second amplification domain may be incorporated into the first strand cDNA molecules by template switching.

In embodiments where the capture probe does not comprise a universal domain, particularly comprising an amplification domain, the second strand of the cDNA molecules may be synthesised in accordance with the above description. The resultant double stranded DNA molecules may be modified to incorporate an amplification domain at the 5' end of the first DNA, e.g. cDNA, strand (a first amplification domain) and, if not incorporated in the second strand DNA, e.g. cDNA synthesis step, at the 5' end of the second DNA, e.g. cDNA, strand (a second amplification domain). Such amplification domains may be incorporated, e.g. by ligating double stranded adaptors to the ends of the DNA, e.g. cDNA, molecules. Enzymes appropriate for the ligation step are known in the art and include, e.g. Tth DNA ligase, Taq DNA ligase, *Thermococcus* sp. (strain 9° N) DNA ligase (9° N™ DNA ligase, New England Biolabs), Ampligase™ (Epicentre Biotechnologies) and T4 DNA ligase. In a preferred embodiment the first and second amplification domains comprise different sequences.

From the above, it is therefore apparent that universal domains, which may comprise an amplification domain, may be added to the secured (i.e. extended) DNA molecules, for example to the cDNA molecules, or their complements (e.g. second strand) by various methods and techniques and combinations of such techniques known in the art, e.g. by use of primers which include such a domain, ligation of adaptors, use of terminal transferase enzymes and/or by template switching methods. As is clear from the discussion herein, such domains may be added before or after release of the DNA molecules from the array.

It will be apparent from the above description that all of the DNA, e.g. cDNA, molecules from a single substrate that have been synthesized by the methods of the invention may all comprise the same first and second amplification domains. Consequently, a single amplification reaction, e.g. PCR, may be sufficient to amplify all of the DNA, e.g. cDNA, molecules. Thus in a preferred embodiment, the method of the invention may comprise a step of amplifying the DNA, e.g. cDNA, molecules. In one embodiment the amplification step is performed after the release of the DNA, e.g. cDNA molecules from the substrate. In other embodiments amplification may be performed on the substrate (i.e. in situ on the substrate). It is known in the art that amplification reactions may be carried out on substrates, such as arrays, and on-chip thermocyclers exist for carrying out such reactions. Thus, in one embodiment arrays which are known in the art as sequencing platforms or for use in any form of sequence analysis (e.g. in or by next generation sequencing technologies) may be used as the basis of the substrates of the present invention (e.g. Illumina bead arrays etc.)

For the synthesis of the second strand of DNA, e.g. cDNA, it is preferable to use a strand displacement polymerase (e.g. Φ29 DNA polymerase, Bst (exo⁻) DNA polymerase, klenow (exo⁻) DNA polymerase) if the cDNA released from the substrate of the array comprises a partially double stranded nucleic acid molecule. For instance, the released nucleic acids will be at least partially double stranded (e.g. DNA:RNA hybrid) in embodiments where the capture probe is immobilized indirectly on the substrate of the array via a surface probe and the step of releasing the DNA, e.g. cDNA molecules comprises a cleavage step. The strand displacement polymerase is necessary to ensure that the second cDNA strand synthesis incorporates the complement of the capture probe including the positional domain (feature identification domain), if present, into the second DNA, e.g. cDNA strand.

It will be evident that the step of releasing at least part of the DNA, e.g. cDNA molecules or their amplicons from the surface of the substrate may be achieved using a number of methods. In some embodiments, it will be evident that the primary aim of the release step is to yield molecules into which the positional domain of the capture probe (or its complement) is incorporated (or included), such that the DNA, e.g. cDNA, molecules or their amplicons are "tagged" according to their feature (or position) on the array. However, as discussed above, a positional domain is not essential, particularly where only a portion of the nucleic acid molecules are released because the other nucleic acid molecules have been removed from the surface of the substrate (and discarded) in an earlier step. The release step thus removes DNA, e.g. cDNA, molecules or amplicons thereof from the substrate, which DNA, e.g. cDNA, molecules or amplicons include the positional information that can be correlated to the tissue sample. For instance, in some embodiments the released DNA comprises a positional domain or its complement (by virtue of it having been incorporated into the secured nucleic acid, e.g. the first strand cDNA by, e.g. extension of the capture probe, and optionally copied in the second strand DNA if second strand synthesis takes place on the array, or copied into amplicons if amplification takes place on the array). Hence, in order to yield sequence analysis data that can be correlated specifically with the various regions in the tissue sample it is advantageous that the released molecules comprise the positional domain of the capture probe (or its complement). However, if the DNA molecules have been released from a specific portion of the substrate, it will be evident that the sequence analysis can be correlated with the region(s) in the tissue sample that were not removed from the substrate.

Since the released molecule may be a first and/or second strand DNA, e.g. cDNA, molecule or amplicon, and since the capture probe may be immobilised indirectly on the substrate, it will be understood that whilst the release step may comprise a step of cleaving a DNA, e.g. cDNA molecule from the array, the release step does not require a step of nucleic acid cleavage; a DNA, e.g. cDNA molecule or an amplicon may simply be released by denaturing a double-stranded molecule, for example releasing the second cDNA strand from the first cDNA strand, or releasing an amplicon from its template or releasing the first strand cDNA molecule (i.e. the extended capture probe) from a surface probe. Accordingly, a DNA, e.g. cDNA, molecule may be released from the substrate by nucleic acid cleavage and/or by denaturation (e.g. by heating to denature a double-stranded molecule). Where amplification is carried out in situ on the substrate, this will of course encompass releasing amplicons by denaturation in the cycling reaction.

In some embodiments, the DNA, e.g. cDNA, molecules are released by enzymatic cleavage of a cleavage domain, which may be located in the universal domain or positional domain of the capture probe. As mentioned above, in some embodiments the cleavage domain must be located upstream (at the 5' end) of the positional domain such that the released DNA, e.g. cDNA, molecules comprise the positional (identification) domain. Suitable enzymes for nucleic acid cleavage include restriction endonucleases, e.g. Rsal. Other enzymes, e.g. a mixture of Uracil DNA glycosylase (UDG) and the DNA glycosylase-lyase Endonuclease VIII (USER™ enzyme) or a combination of the MutY and T7 endonuclease I enzymes, are preferred embodiments of the methods of the invention.

In an alternative embodiment, the DNA, e.g. cDNA, molecules may be released from the surface of the substrate by physical means. For instance, in embodiments where the capture probe is indirectly immobilized on the substrate, e.g. via hybridization to the surface probe, it may be sufficient to disrupt the interaction between the nucleic acid molecules. Methods for disrupting the interaction between nucleic acid molecules, e.g. denaturing double stranded nucleic acid molecules, are well known in the art. A straightforward method for releasing the DNA, e.g. cDNA, molecules (i.e. of stripping the substrate, e.g. array, of the synthesized DNA, e.g. cDNA molecules) is to use a solution that interferes with the hydrogen bonds of the double stranded molecules. In a preferred embodiment of the invention, the DNA, e.g. cDNA, molecules may be released by applying heated water, e.g. water or buffer of at least 85° C., preferably at least 90, 91, 92, 93, 94, 95, 96, 97, 98, 99° C. As an alternative or addition to the use of a temperature sufficient to disrupt the hydrogen bonding, the solution may comprise salts, surfactants etc. that may further destabilize the interaction between the nucleic acid molecules, resulting in the release of the DNA, e.g. cDNA, molecules.

It will be understood that the application of a high temperature solution, e.g. 90-99° C. water may be sufficient to disrupt a covalent bond used to immobilize the capture probe or surface probe to the substrate. Hence, in a preferred embodiment, the DNA, e.g. cDNA, molecules may be released by applying hot water to the substrate to disrupt covalently immobilized capture or surface probes.

It is implicit that the released DNA, e.g. cDNA, molecules (the solution comprising the released DNA, e.g. cDNA, molecules) are collected for further manipulation, e.g. second strand synthesis and/or amplification. Nevertheless, the method of the invention may be seen to comprise a step of collecting or recovering the released DNA, e.g. cDNA, molecules. As noted above, in the context of in situ amplification the released molecules may include amplicons of the secured nucleic acid, e.g. cDNA.

In embodiments of methods of the invention, it may be desirable to remove any unextended capture probes. This may be, for example, after the step of releasing DNA molecules from the substrate. Any desired or convenient method may be used for such removal including, for example, use of an enzyme to degrade the unextended probes, e.g. exonuclease.

The DNA, e.g. cDNA molecules, or amplicons, that have been released from the substrate, which may have been modified as discussed above, are analysed to investigate (e.g. determine their sequence, although as noted above actual sequence determination is not required—any method of analysing the sequence may be used). Thus, any method of nucleic acid analysis may be used. The step of sequence analysis may identify the positional domain and hence allow the analysed molecule to be localised to a position in the tissue sample. Similarly, the nature or identity of the analysed molecule may be determined. In this way the nucleic acid, e.g. RNA, at given position in the substrate, and hence in the tissue sample may be determined. Hence the analysis step may include or use any method which identifies the analysed molecule (and hence the "target" molecule) and its positional domain. Generally such a method will be a sequence-specific method. For example, the method may use sequence-specific primers or probes, particularly primers or probes specific for the positional domain and/or for a specific nucleic acid molecule to be detected or analysed e.g. a DNA molecule corresponding to a nucleic acid, e.g. RNA or cDNA molecule to be detected. Typically in such a method sequence-specific amplification primers e.g. PCR primers may be used.

In some embodiments it may be desirable to analyse a subset or family of target related molecules, e.g. all of the sequences that encode a particular group of proteins which share sequence similarity and/or conserved domains, e.g. a family of receptors. Hence, the amplification and/or analysis methods described herein may use degenerate or gene family specific primers or probes that hybridise to a subset of the captured nucleic acids or nucleic acids derived therefrom, e.g. amplicons. In a particularly preferred embodiment, the amplification and/or analysis methods may utilise a universal primer (i.e. a primer common to all of the captured sequences) in combination with a degenerate or gene family specific primer specific for a subset of target molecules.

Thus in one embodiment, amplification-based, especially PCR-based, methods of sequence analysis are used.

However, the steps of modifying and/or amplifying the released DNA, e.g. cDNA, molecules may introduce additional components into the sample, e.g. enzymes, primers, nucleotides etc. Hence, the methods of the invention may further comprise a step of purifying the sample comprising the released DNA, e.g. cDNA molecules or amplicons prior to the sequence analysis, e.g. to remove oligonucleotide primers, nucleotides, salts etc that may interfere with the sequencing reactions. Any suitable method of purifying the DNA, e.g. cDNA molecules may be used.

As noted above, sequence analysis of the released DNA molecules may be direct or indirect. Thus the sequence analysis material or substrate (which may be viewed as the molecules which are subjected to the sequence analysis step or process) may directly be the molecules which is released from the object substrate, e.g. array, or it may be a molecule which is derived therefrom. Thus, for example in the context of sequence analysis step which involves a sequencing reaction, the sequencing template may be the molecule which is released from the object substrate, e.g. array, or it may be a molecule derived therefrom. For example, a first and/or second strand DNA, e.g. cDNA, molecule released from the substrate, e.g. array, may be directly subjected to sequence analysis (e.g. sequencing), i.e. may directly take part in the sequence analysis reaction or process (e.g. the sequencing reaction or sequencing process, or be the molecule which is sequenced or otherwise identified). In the context of in situ amplification the released molecule may be an amplicon. Alternatively, the released molecule may be subjected to a step of second strand synthesis or amplification before sequence analysis (e.g. sequencing or identification by other means). The sequence analysis substrate (e.g. template) may thus be an amplicon or a second strand of a molecule which is directly released from the object substrate, e.g. array.

Both strands of a double stranded molecule may be subjected to sequence analysis (e.g. sequenced) but the invention is not limited to this and single stranded molecules (e.g. cDNA) may be analysed (e.g. sequenced). For example various sequencing technologies may be used for single molecule sequencing, e.g. the Helicos or Pacbio technologies, or nanopore sequencing technologies which are being developed. Thus, in one embodiment the first strand of DNA, e.g. cDNA may be subjected to sequencing. The first strand DNA, e.g. cDNA may need to be modified at the 3' end to enable single molecule sequencing. This may be done by procedures analogous to those for handling the second DNA, e.g. cDNA strand. Such procedures are known in the art.

In a preferred aspect of the invention the sequence analysis will identify or reveal a portion of captured nucleic acid, e.g. RNA, sequence and optionally the sequence of the positional domain. In some embodiments the sequence of the positional domain (or tag) will identify the feature to which the nucleic acid, e.g. mRNA, molecule was captured. The sequence of the captured nucleic acid, e.g. RNA, molecule may be compared with a sequence database of the organism from which the sample originated to determine the gene to which it corresponds. By determining which region (e.g. cell) of the tissue sample was in contact with the position or area, e.g. feature, of the substrate from which the captured nucleic acid was released, it is possible to determine which region of the tissue sample was expressing said gene. This analysis may be achieved for all of the DNA, e.g. cDNA, molecules generated by the methods of the invention, yielding a spatial transcriptome of the tissue sample. However, in some embodiments only a selection of the transcripts present in the tissue sample may be captured on the substrate (e.g. if the capture domain of the capture probe comprises a sequence specific for a gene or set of genes) and/or only a portion of the captured molecules may be selected for further analysis, e.g. sequence analysis (e.g. a portion of the captured molecules may be removed from the substrate prior to the sequence analysis step).

By way of a representative example, sequencing data may be analysed to sort the sequences into specific species of capture probe, e.g. according to the sequence of the positional domain. This may be achieved by, e.g. using the FastX toolkit FASTQ Barcode splitter tool to sort the sequences into individual files for the respective capture probe positional domain (tag) sequences. The sequences of each species, i.e. from each feature, may be analyzed to determine the identity of the transcripts. For instance, the sequences may be identified using e.g. Blastn software, to compare the sequences to one or more genome databases, preferably the database for the organism from which the tissue sample was obtained. The identity of the database sequence with the greatest similarity to the sequence generated by the methods of the invention will be assigned to said sequence. In general, only hits with a certainty of at least $1e^{-6}$, preferably $1e^{-7}$, $1e^{-8}$, or $1e^{-9}$ will be considered to have been successfully identified.

It will be apparent that any nucleic acid sequencing method may be utilised in the methods of the invention. However, the so-called "next generation sequencing" techniques will find particular utility in the present invention. High-throughput sequencing is particularly useful in the methods of the invention because it enables a large number of nucleic acids to be partially sequenced in a very short period of time. In view of the recent explosion in the number of fully or partially sequenced genomes, it is not essential to sequence the full length of the generated DNA, e.g. cDNA molecules to determine the gene to which each molecule corresponds. For example, the first 100 nucleotides from each end of the DNA, e.g. cDNA molecules should be sufficient to identify the gene expressed and, in embodiments in which the capture probes are arrayed on the substrate, the feature to which the nucleic acid, e.g. mRNA, was captured (i.e. its location on the array). In some embodiments, the sequence reaction from the "capture probe end" of the DNA, e.g. cDNA molecules, yields the sequence of the positional domain and at least about 20 bases, preferably 30 or 40 bases of transcript specific sequence data. However, in embodiments in which the capture probe does not contain a positional domain, the sequence reaction from the "capture probe end" of the DNA, may yield at least about 70 bases, preferably 80, 90, or 100 bases of transcript specific sequence data. The sequence reaction from the "non-capture probe end" may yield at least about 70 bases, preferably 80, 90, or 100 bases of transcript specific sequence data.

As a representative example, the sequencing reaction may be based on reversible dye-terminators, such as used in the Illumina™ technology. For example, DNA molecules are first attached to primers on, e.g. a glass or silicon slide and amplified so that local clonal colonies are formed (bridge amplification). Four types of ddNTPs are added, and non-incorporated nucleotides are washed away. Unlike pyrosequencing, the DNA can only be extended one nucleotide at a time. A camera takes images of the fluorescently labelled nucleotides then the dye along with the terminal 3' blocker is chemically removed from the DNA, allowing a next cycle. This may be repeated until the required sequence data is obtained. Using this technology, thousands of nucleic acids may be sequenced simultaneously on a single slide.

Other high-throughput sequencing techniques may be equally suitable for the methods of the invention, e.g. pyrosequencing. In this method the DNA is amplified inside water droplets in an oil solution (emulsion PCR), with each droplet containing a single DNA template attached to a single primer-coated bead that then forms a clonal colony. The sequencing machine contains many picoliter-volume wells each containing a single bead and sequencing enzymes. Pyrosequencing uses luciferase to generate light for detection of the individual nucleotides added to the nascent DNA and the combined data are used to generate sequence read-outs.

An example of a technology in development is based on the detection of hydrogen ions that are released during the polymerisation of DNA. A microwell containing a template DNA strand to be sequenced is flooded with a single type of nucleotide. If the introduced nucleotide is complementary to the leading template nucleotide it is incorporated into the growing complementary strand. This causes the release of a hydrogen ion that triggers a hypersensitive ion sensor, which indicates that a reaction has occurred. If homopolymer repeats are present in the template sequence multiple nucleotides will be incorporated in a single cycle. This leads to a corresponding number of released hydrogen ions and a proportionally higher electronic signal.

Thus, it is clear that future sequencing formats are slowly being made available, and with shorter run times as one of the main features of those platforms it will be evident that other sequencing technologies will be useful in the methods of the invention, e.g. nanopore sequencing methods.

An essential feature of the present invention, as described above, is a step of securing a complementary strand of the captured nucleic acid molecules to the capture probe, e.g. reverse transcribing the captured RNA molecules. The reverse transcription reaction is well known in the art and in representative reverse transcription reactions, the reaction mixture includes a reverse transcriptase, dNTPs and a suitable buffer. The reaction mixture may comprise other components, e.g. RNase inhibitor(s). The primers and template are the capture domain of the capture probe and the captured RNA molecules, as described above. In the subject methods, each dNTP will typically be present in an amount ranging from about 10 to 5000 µM, usually from about 20 to 1000 µM. It will be evident that an equivalent reaction may be performed to generate a complementary strand of a captured DNA molecule, using an enzyme with DNA polymerase activity. Reactions of this type are well known in the art and are described in more detail below.

In some embodiments, a labelled dNTP may be present in the reaction mix, thereby incorporating a label into the synthesized DNA molecule. In a representative embodiment, the labelled dNTP is a fluorescently labelled dNTP, e.g. Cy3-dCTP.

The desired reverse transcriptase activity may be provided by one or more distinct enzymes, wherein suitable examples are: M-MLV, MuLV, AMV, HIV, ArrayScript™, MultiScribe™, ThermoScript™, and SuperScript® I, II, and III enzymes.

The reverse transcriptase reaction may be carried out at any suitable temperature, which will be dependent on the properties of the enzyme. Typically, reverse transcriptase reactions are performed between 37-55° C., although temperatures outside of this range may also be appropriate. The reaction time may be as little as 1, 2, 3, 4 or 5 minutes or as much as 48 hours. Typically the reaction will be carried out for between 3-12 hours, such as 5-120 minutes, 5-60, 5-45 or 5-30 minutes or 1-10 or 1-5 minutes according to choice. The reaction time is not critical and any desired reaction time may be used. For instance, overnight incubations are commonplace.

As indicated above, certain embodiments of the methods include an amplification step, where the copy number of generated DNA, e.g. cDNA molecules is increased, e.g. in order to enrich the sample to obtain a better representation of the nucleic acids, e.g. transcripts, captured from the tissue sample. The amplification may be linear or exponential, as desired, where representative amplification protocols of interest include, but are not limited to: polymerase chain reaction (PCR); isothermal amplification, etc.

The polymerase chain reaction (PCR) is well known in the art, being described in U.S. Pat. Nos. 4,683,202; 4,683,195; 4,800,159; 4,965,188 and 5,512,462, the disclosures of which are herein incorporated by reference. In representative PCR amplification reactions, the reaction mixture that includes the above released DNA, e.g. cDNA molecules from the substrate, e.g. array, which are combined with one or more primers that are employed in the primer extension reaction, e.g., the PCR primers that hybridize to the first and/or second amplification domains (such as forward and reverse primers employed in geometric (or exponential) amplification or a single primer employed in a linear amplification). The oligonucleotide primers with which the released DNA, e.g. cDNA molecules (hereinafter referred to as template DNA for convenience) is contacted will be of sufficient length to provide for hybridization to complementary template DNA under annealing conditions (described in greater detail below). The length of the primers will depend on the length of the amplification domains, but will generally be at least 10 bp in length, usually at least 15 bp in length and more usually at least 16 bp in length and may be as long as 30 bp in length or longer, where the length of the primers will generally range from 18 to 50 bp in length, usually from about 20 to 35 bp in length. The template DNA may be contacted with a single primer or a set of two primers (forward and reverse primers), depending on whether primer extension, linear or exponential amplification of the template DNA is desired.

In addition to the above components, the reaction mixture produced in the subject methods typically includes a polymerase and deoxyribonucleoside triphosphates (dNTPs). The desired polymerase activity may be provided by one or more distinct polymerase enzymes. In many embodiments, the reaction mixture includes at least a Family A polymerase, where representative Family A polymerases of interest include, but are not limited to: *Thermus aquaticus* polymerases, including the naturally occurring polymerase (Taq) and derivatives and homologues thereof, such as Klentaq (as described in Barnes et al, Proc. Natl. Acad. Sci USA (1994) 91:2216-2220); *Thermus thermophilus* polymerases, including the naturally occurring polymerase (Tth) and derivatives and homologues thereof, and the like. In certain embodiments where the amplification reaction that is carried out is a high fidelity reaction, the reaction mixture may further include a polymerase enzyme having 3'-5' exonuclease activity, e.g., as may be provided by a Family B polymerase, where Family B polymerases of interest include, but are not limited to: *Thermococcus litoralis* DNA polymerase (Vent) as described in Perler et al., Proc. Natl. Acad. Sci. USA (1992) 89:5577-5581; *Pyrococcus* species GB-D (Deep Vent); *Pyrococcus furiosus* DNA polymerase (Pfu) as described in Lundberg et al., Gene (1991) 108:1-6, *Pyrococcus woesei* (Pwo) and the like. Where the reaction mixture includes both a Family A and Family B polymerase, the Family A polymerase may be present in the reaction mixture in an amount greater than the Family B polymerase, where the difference in activity will usually be at least 10-fold, and more usually at least about 100-fold. Usually the reaction mixture will include four different types of dNTPs corresponding to the four naturally occurring bases present, i.e. dATP, dTTP, dCTP and dGTP. In the subject methods, each dNTP will typically be present in an amount ranging from about 10 to 5000 µM, usually from about 20 to 1000 µM.

The reaction mixtures prepared in the reverse transcriptase and/or amplification steps of the subject methods may further include an aqueous buffer medium that includes a source of monovalent ions, a source of divalent cations and a buffering agent. Any convenient source of monovalent ions, such as KCl, K-acetate, $NH_4$-acetate, K-glutamate, $NH_4Cl$, ammonium sulphate, and the like may be employed. The divalent cation may be magnesium, manganese, zinc and the like, where the cation will typically be magnesium. Any convenient source of magnesium cation may be employed, including $MgCl_2$, Mg-acetate, and the like. The amount of $Mg^{2+}$ present in the buffer may range from 0.5 to 10 mM, but will preferably range from about 3 to 6 mM, and will ideally be at about 5 mM. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, where most preferred is pH 7.3 at 72° C. Other agents which may be present in the buffer medium include chelating agents, such as EDTA, EGTA and the like.

In preparing the reverse transcriptase, DNA extension or amplification reaction mixture of the steps of the subject methods, the various constituent components may be combined in any convenient order. For example, in the amplification reaction the buffer may be combined with primer, polymerase and then template DNA, or all of the various constituent components may be combined at the same time to produce the reaction mixture.

As discussed above, a preferred embodiment of the invention the DNA, e.g. cDNA molecules may be modified by the addition of amplification domains to the ends of the nucleic acid molecules, which may involve a ligation reaction. A ligation reaction is also required for the in situ synthesis of the capture probe on the substrate, when the capture probe is immobilized indirectly on the substrate surface.

As is known in the art, ligases catalyze the formation of a phosphodiester bond between juxtaposed 3'-hydroxyl and 5'-phosphate termini of two immediately adjacent nucleic acids. Any convenient ligase may be employed, where representative ligases of interest include, but are not limited to: Temperature sensitive and thermostable ligases. Temperature sensitive ligases include, but are not limited to, bacteriophage T4 DNA ligase, bacteriophage T7 ligase, and *E. coli* ligase. Thermostable ligases include, but are not limited to, Taq ligase, Tth ligase, and Pfu ligase. Thermostable ligase may be obtained from thermophilic or hyperthermophilic organisms, including but not limited to, prokaryotic, eukaryotic, or archael organisms. Certain RNA ligases may also be employed in the methods of the invention.

In this ligation step, a suitable ligase and any reagents that are necessary and/or desirable are combined with the reaction mixture and maintained under conditions sufficient for ligation of the relevant oligonucleotides to occur. Ligation reaction conditions are well known to those of skill in the art. During ligation, the reaction mixture in certain embodiments may be maintained at a temperature ranging from about 4° C. to about 50° C., such as from about 20° C. to about 37° C. for a period of time ranging from about 5 seconds to about 16 hours, such as from about 1 minute to about 1 hour. In yet other embodiments, the reaction mixture may be maintained at a temperature ranging from about 35° C. to about 45° C., such as from about 37° C. to about 42° C., e.g., at or about 38° C., 39° C., 40° C. or 41° C., for a period of time ranging from about 5 seconds to about 16 hours, such as from about 1 minute to about 1 hour, including from about 2 minutes to about 8 hours. In a representative embodiment, the ligation reaction mixture includes 50 mM Tris pH7.5, 10 mM $MgCl_2$, 10 mM DTT, 1 mM ATP, 25 mg/ml BSA, 0.25 units/ml RNase inhibitor, and T4 DNA ligase at 0.125 units/ml. In yet another representative embodiment, 2.125 mM magnesium ion, 0.2 units/ml RNase inhibitor; and 0.125 units/ml DNA ligase are employed. The amount of adaptor in the reaction will be dependent on the concentration of the DNA, e.g. cDNA in the sample and will generally be present at between 10-100 times the molar amount of DNA, e.g. cDNA.

By way of a representative example the method of the invention may comprise the following steps:

(a) contacting an object substrate with a tissue sample, wherein at least one species of capture probe is directly or indirectly immobilized on said substrate such that the probes are oriented to have a free 3' end to enable said probe to function as a reverse transcriptase (RT) primer, such that RNA of the tissue sample hybridises to said capture probes;

(b) imaging the tissue sample on the substrate;

(c) reverse transcribing the captured mRNA molecules to generate cDNA molecules, wherein labelled nucleotides are incorporated into the synthesized part of the cDNA molecules;

(d) washing the substrate to remove residual tissue;

(e) imaging the substrate such that the signal from the labelled cDNA molecules is detected;

(f) removing the labelled cDNA from at least one portion of the surface of the substrate;

(g) releasing at least part of the remaining labelled cDNA molecules from the surface of the array;

(h) performing second strand cDNA synthesis on the released cDNA molecules;

and (i) analysing the sequence of (e.g. sequencing) the cDNA molecules.

By way of an alternative representative example the method of the invention may comprise the following steps:

(a) contacting an object substrate with a tissue sample, wherein at least one species of capture probe is directly or indirectly immobilized on said substrate such that the probes are oriented to have a free 3' end to enable said probe to function as a reverse transcriptase (RT) primer, such that RNA of the tissue sample hybridises to said capture probes;

(b) optionally rehydrating the tissue sample;

(c) reverse transcribing the captured mRNA molecules to generate cDNA molecules;

(d) imaging the tissue sample on the substrate;

(e) washing the substrate to remove residual tissue;

(f) labelling the cDNA molecules with a nucleic acid stain;

(g) imaging the substrate such that the signal from the labelled cDNA molecules is detected;

(h) removing the labelled cDNA from at least one portion of the surface of the substrate;

(i) releasing at least part of the remaining labelled cDNA molecules from the surface of the array;

(j) amplifying the released cDNA molecules;

(k) optionally purifying the cDNA molecules to remove components that may interfere with the sequencing reaction; and (l) analysing the sequence of (e.g. sequencing) the cDNA molecules.

By way of yet a further representative example the method of the invention may comprise the following steps:

(a) contacting an object substrate with a tissue sample, wherein at least one species of capture probe is directly or indirectly immobilized on said substrate such that the probes are oriented to have a free 3' end to enable said probe to function as a reverse transcriptase (RT) primer, such that RNA of the tissue sample hybridises to said capture probes;

(b) imaging the tissue sample on the substrate;

(c) reverse transcribing the captured mRNA molecules to generate cDNA molecules, wherein labelled nucleotides are incorporated into the synthesized part of the cDNA molecules;

(d) washing the substrate to remove residual tissue;

(e) imaging the substrate such that the signal from the labelled cDNA molecules is detected;

(f) repeating steps (a)-(e), with a second object substrate, using different conditions in step (a);

(g) comparing the intensity and/or resolution of the signal from the labelled cDNA molecules immobilized on said first and second object substrate; and (h) selecting the conditions that provide the optimum signal intensity and/or resolution of the labelled cDNA molecules.

By way of a further alternative representative example the method of the invention may comprise the following steps:

(a) contacting an object substrate with a tissue sample, wherein multiple species of capture probes are directly or indirectly immobilized such that each species occupies a distinct position on said substrate and is oriented to have a free 3' end to enable said probe to function as a reverse transcriptase (RT) primer, wherein each species of said capture probe comprises a nucleic acid molecule with 5' to 3':

(i) a positional domain that corresponds to the position of the capture probe on the substrate, and (ii) a capture domain;

such that RNA of the tissue sample hybridises to said capture probes;

(b) optionally rehydrating the tissue sample;

(c) imaging the tissue sample on the substrate;

(d) reverse transcribing the captured mRNA molecules to generate cDNA molecules, wherein labelled nucleotides are incorporated into the synthesized part of the cDNA molecules;

(e) washing the substrate to remove residual tissue;

(f) imaging the substrate such that the signal from the labelled cDNA molecules is detected;

(g) removing the labelled cDNA from at least one portion of the surface of the substrate;

(h) releasing at least part of the remaining labelled cDNA molecules from the surface of the array;

(i) amplifying the released cDNA molecules;

(j) optionally purifying the cDNA molecules to remove components that may interfere with the sequencing reaction; and (k) analysing the sequence of (e.g. sequencing) the cDNA molecules.

The present invention includes any suitable combination of the steps in the above described methods. It will be understood that the invention also encompasses variations of these methods, for example where amplification is performed in situ on the substrate, e.g. array. Also encompassed are methods which omit the step of imaging the tissue sample.

The invention may also be seen to include a method for making or producing an object substrate (i) for use in capturing mRNA from a tissue sample that is contacted with said substrate; (ii) for use in determining and/or analysing a (e.g. the partial or global) transcriptome of a tissue sample; or (iii) for use in determining the optimum conditions for localised or spatial detection of nucleic acid from a tissue sample contacted with a substrate, said method comprising immobilizing, directly or indirectly, at least one species of capture probe to a substrate such that each probe is oriented to have a free 3' end to enable said probe to function as a reverse transcriptase (RT) primer.

Optionally the probes are immobilized uniformly on the object substrate, i.e. the probes are not arrayed as distinct features. In a particular embodiment of the invention, the probes are identical.

In some embodiments of the invention the probes are capable of hybridizing to (i.e. capturing) all mRNA, i.e. RNA molecules with a polyA tail. Hence, in particularly preferred embodiments of the invention the probes may comprise regions of consecutive dTTP or dUTP nucleotides, e.g. oligoT and/or oligoU nucleotides, as described in more detail above.

The method of immobilizing the capture probes on the object substrate may be achieved using any suitable means as described herein. Where the capture probes are immobilized on the array indirectly the capture probe may be synthesized on the object substrate. Said method may comprise any one or more of the following steps:

(a) immobilizing directly or indirectly multiple surface probes to a substrate, wherein the surface probes comprise:

(i) a domain capable of hybridizing to part of the capture domain oligonucleotide (a part not involved in capturing the nucleic acid, e.g. RNA); and (ii) a complementary universal domain;

(b) hybridizing to the surface probes immobilized on the substrate capture domain oligonucleotides and universal domain oligonucleotides;

(c) ligating the universal domain to the capture domain oligonucleotide to produce the capture oligonucleotide.

Thus, in one particular embodiment the method may be viewed as a method for making or producing an object substrate comprising a substrate on which one or more species of capture probe, comprising a capture domain, is directly or indirectly immobilized such that each probe is oriented to have a free 3' end to enable said probe to function as a reverse transcriptase (RT) primer, wherein the probes are immobilised on the object substrate with a homogeneous distribution and said substrate is for use in:
  (i) capturing RNA from a tissue sample that is contacted with said object substrate; or
  (ii) localised or spatial detection of RNA in a tissue sample, said method comprising:
    (a) immobilizing directly or indirectly multiple surface probes to a substrate, wherein the surface probes comprise:
      (i) a domain capable of hybridizing to part of a capture domain oligonucleotide; and
      (ii) a domain that is complementary to a universal domain oligonucleotide;
    (b) hybridizing to the surface probes immobilized on the substrate, capture domain oligonucleotides and universal domain oligonucleotides;
    (c) ligating the universal domain oligonucleotides to the capture domain oligonucleotides to produce the capture probes.

The features of the object substrate produced by the above method of producing the array of the invention, may be further defined in accordance with the above description.

Thus, in one embodiment the invention provides an object substrate for use in the localised or spatial detection of RNA in a tissue sample, comprising a planar substrate on which one or more species of capture probe, comprising a capture domain, is directly or indirectly immobilized such that each probe is oriented to have a free 3' end to enable said probe to function as a reverse transcriptase (RT) primer wherein the probes are immobilised on the object substrate with a homogeneous distribution and wherein the capture probe is selected from an oligonucleotide comprising a poly-T, poly-U and/or random oligonucleotide sequence.

BRIEF DESCRIPTION OF THE DRAWINGS

The invention will be further described with reference to the following non-limiting Examples with reference to the following drawings in which.

EXAMPLES

Example 1

Preparation of the Array

Figure 1:
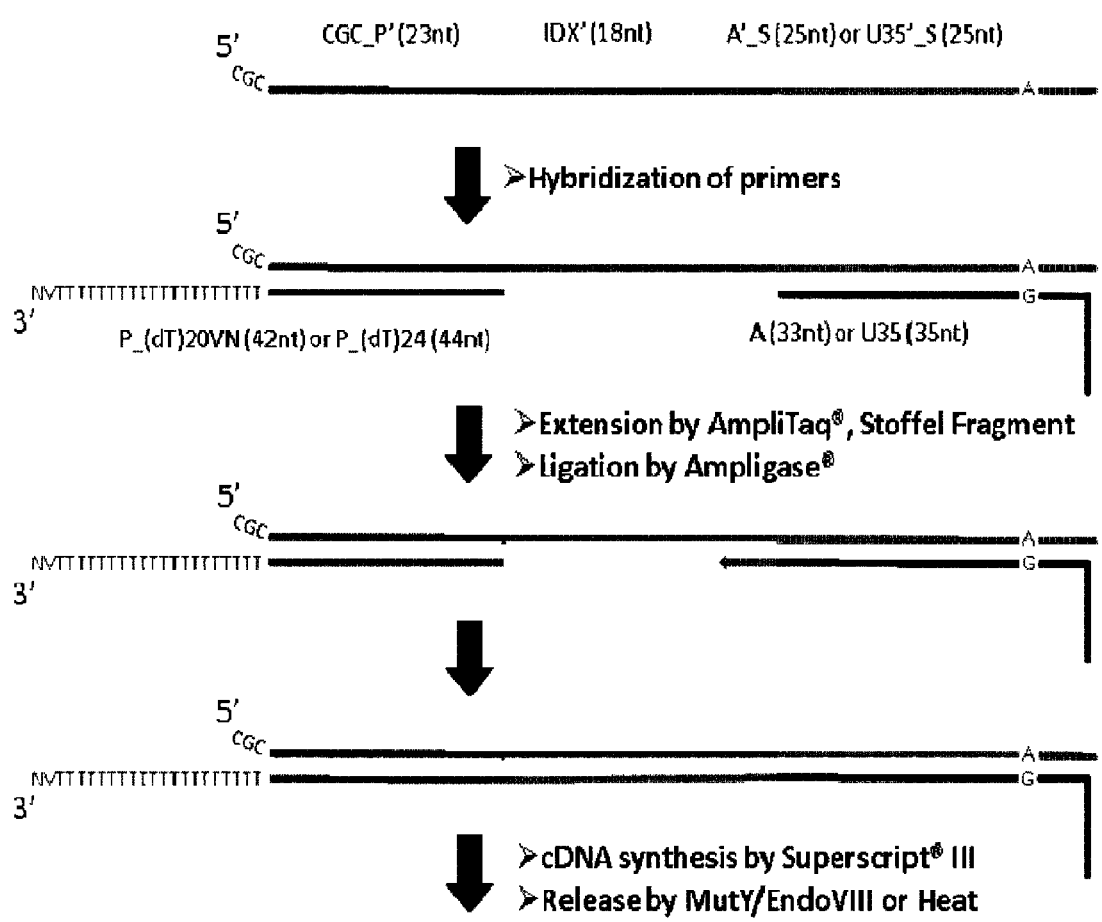
FIG. 1 shows 3' to 5' surface probe composition and synthesis of 5' to 3' oriented capture probes that are indirectly immobilised at the array surface.
Figure 2:
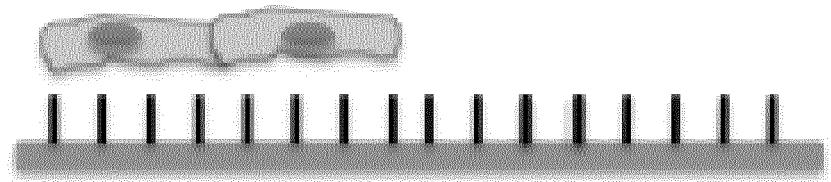
FIG. 2 shows how the methods of the invention can be used to determine the optimum conditions for capturing RNA from a tissue sample on a substrate, wherein: (A) shows a tissue sample that is not permeabilized sufficiently to allow the capture of RNA on the substrate; (B) shows a tissue sample that is permeabilized to allow capture of RNA on the substrate whilst retaining spatial information; and (C) shows a tissue sample that is too permeable such that the RNA has been allowed to diffuse away from its origin in the tissue sample and captured RNA does not correlate accurately with its original spatial distribution in the tissue sample.
Figure 2:
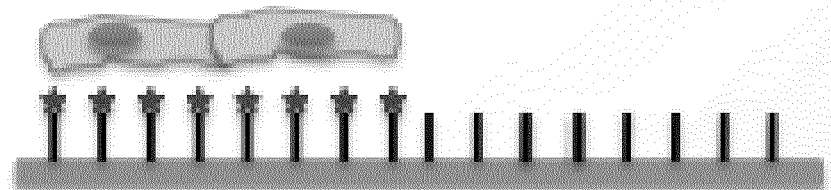
Figure 2:
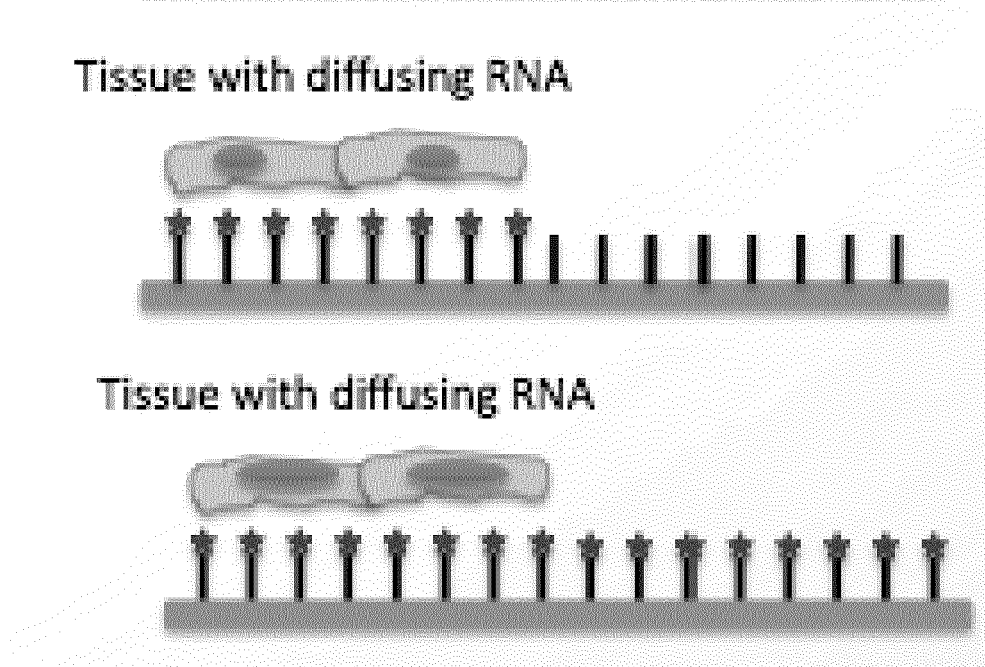

The following experiments demonstrate how oligonucleotide probes may be attached to an array substrate by either the 5' or 3' end to yield an array with capture probes capable of hybridizing to mRNA.

Preparation of In-House Printed Microarray with 5' to 3' Oriented Probes

20 RNA-capture oligonucleotides with individual tag sequences (Tag 1-20, Table 1 were spotted on glass slides to function as capture probes. The probes were synthesized with a 5'-terminus amino linker with a C6 spacer. All probes where synthesized by Sigma-Aldrich (St. Louis, Mo., USA). The RNA-capture probes were suspended at a concentration of 20 μM in 150 mM sodium phosphate, pH 8.5 and were spotted using a Nanoplotter NP2.1/E (Gesim, Grosserkmannsdorf, Germany) onto CodeLink™ Activated microarray slides (7.5 cm×2.5 cm; Surmodics, Eden Prairie, Minn., USA). After printing, surface blocking was performed according to the manufacturer's instructions. The probes were printed in 16 identical arrays on the slide, and each array contained a pre-defined printing pattern. The 16 sub-arrays were separated during hybridization by a 16-pad mask (ChipClip™ Schleicher & Schuell BioScience, Keene, N.H., USA).

TABLE 1

| Name | Sequence | 5' mod | 3' mod | Length |
|---|---|---|---|---|
| Sequences for free 3' capture probes | | | | |
| TAP-ID1 | UUAAGTACAAATCTCGACTGCCACTCTGAACCTTCT CCTTCTCCTTCACCTTTTTTTTTTTTTTTTTTTVN (SEQ ID NO: 1) | | Amino-C6 | 72 |
| Enzymatic recog | UUAAGTACAA (SEQ ID NO: 2) | | | 10 |
| Universal amp handle P | ATCTCGACTGCCACTCTGAA (SEQ ID NO: 3) | | | 20 |
| ID1 | CCTTCTCCTTCTCCTTCACC (SEQ ID NO: 4) | | | 20 |
| Capture sequence | TTTTTTTTTTTTTTTTTTTTVN (SEQ ID NO: 5) | | | 22 |
| ID1 | CCTTCTCCTTCTCCTTCACC (SEQ ID NO: 6) | | | 20 |
| ID2 | CCTTGCTGCTTCTCCTCCTC (SEQ ID NO: 7) | | | 20 |
| ID3 | ACCTCCTCCGCCTCCTCCTC (SEQ ID NO: 8) | | | 20 |
| ID4 | GAGACATACCACCAAGAGAC (SEQ ID NO: 9) | | | 20 |
| ID5 | GTCCTCTATTCCGTCACCAT (SEQ ID NO: 10) | | | 20 |
| ID6 | GACTGAGCTCGAACATATGG (SEQ ID NO: 11) | | | 20 |
| ID7 | TGGAGGATTGACACAGAACG (SEQ ID NO: 12) | | | 20 |
| ID8 | CCAGCCTCTCCATTACATCG (SEQ ID NO: 13) | | | 20 |
| ID9 | AAGATCTACCAGCCAGCCAG (SEQ ID NO: 14) | | | 20 |
| ID10 | CGAACTTCCACTGTCTCCTC (SEQ ID NO: 15) | | | 20 |
| ID11 | TTGCGCCTTCTCCAATACAC (SEQ ID NO: 16) | | | 20 |
| ID12 | CTCTTCTTAGCATGCCACCT (SEQ ID NO: 17) | | | 20 |
| ID13 | ACCACTTCTGCATTACCTCC (SEQ ID NO: 18) | | | 20 |
| ID14 | ACAGCCTCCTCTTCTTCCTT (SEQ ID NO: 19) | | | 20 |
| ID15 | AATCCTCTCCTTGCCAGTTC (SEQ ID NO: 20) | | | 20 |
| ID16 | GATGCCTCCACCTGTAGAAC (SEQ ID NO: 21) | | | 20 |
| ID17 | GAAGGAATGGAGGATATCGC (SEQ ID NO: 22) | | | 20 |
| ID18 | GATCCAAGGACCATCGACTG (SEQ ID NO: 23) | | | 20 |
| ID19 | CCACTGGAACCTGACAACCG (SEQ ID NO: 24) | | | 20 |
| ID20 | CTGCTTCTTCCTGGAACTCA (SEQ ID NO: 25) | | | 20 |
| Sequences for free 5' surface probes and on-chip free 3' capture probe synthesis | | | | |
| Free 5' surface probe-A | GCGTTCAGAGTGGCAGTCGAGATCACGCGGCAATCATATC GGACAGATCGGAAGAGCGTAGTGTAG (SEQ ID NO: 26) | Amino C7 | | 66 |
| Free 5' surface probe-U | GCGTTCAGAGTGGCAGTCGAGATCACGCGGCAATCATATC GGACGGCTGCTGGTAAATAGAGATCA (SEQ ID NO: 27) | Amino C7 | | 66 |
| Nick | GCG | | | 3 |

TABLE 1-continued

| Name | Sequence | 5' mod | 3' mod | Length |
|---|---|---|---|---|
| LP' | TTCAGAGTGGCAGTCGAGATCAC (SEQ ID NO: 28) | | | 23 |
| ID' | GCGGCAATCATATCGGAC (SEQ ID NO: 29) | | | 18 |
| A' 22 bp MutY mismatch | AGATCGGAAGAGCGTAGTGTAG (SEQ ID NO: 30) | | | 22 |
| U' 22 bp MutY mismatch | GGCTGCTGGTAAATAGAGATCA (SEQ ID NO: 31) | | | |
| Hybridized sequences for capture probe synthesis | | | | |
| Illumina amp handle A | ACACTCTTTCCCTACACGACGCTCTTCCGATCT (SEQ ID NO: 32) | | | 33 |
| Universa ampl handle U | AAGTGTGGAAAGTTGATCGCTATTTACCAGCAGCC (SEQ ID NO: 33) | | | 35 |
| Capture_LP_Poly-dTVN | GTGATCTCGACTGCCACTCTGAATTTTTTTTTTTTTTTTTVN (SEQ ID NO: 34) | | Phosphorylated | 45 |
| Capture_LP_Poly-d24T | GTGATCTCGACTGCCACTCTGAATTTTTTTTTTTTTTTTTTTTT (SEQ ID NO: 35) | | Phosphorylated | 47 |
| Additional secondary universal amplification handles | | | | |
| Illumina amp handle B | AGACGTGTGCTCTTCCGATCT (SEQ ID NO: 36) | | | 21 |
| Universal amp handle X | ACGTCTGTGAATAGCCGCAT (SEQ ID NO: 37) | | | 20 |
| B_R6 handle (or X) | AGACGTGTGCTCTTCCGATCTNNNNNNNN (SEQ ID NO: 38) | | | 27 (26) |
| B_R8 handle (or X) | AGACGTGTGCTCTTCCGATCTNNNNNNNNNN (SEQ ID NO: 39) | | | 29 (28) |
| B_polyTVN (or X) | AGACGTGTGCTCTTCCGATCTTTTTTTTTTTTTTTTTTTTVN (SEQ ID NO: 40) | | | 43 (42) |
| B_poly24T (or X) | AGACGTGTGCTCTTCCGATCTTTTTTTTTTTTTTTTTTTTTTT (SEQ ID NO: 41) | | | 45 (44) |
| Amplification handle to incorporate A handle into P handle products | | | | |
| A_P handle | ACACTCTTTCCCTACACGACGCTCTTCCGATCTATCTCGACTGCCACTCTGAA (SEQ ID NO: 42) | | | 53 |

Preparation of In-House Printed Microarray with 3' to 5' Oriented Probes and Synthesis of 5' to 3' Oriented Capture Probes Printing of surface probe oligonucleotides was performed as in the case with 5' to 3' oriented probes above, with an amino-C7 linker at the 3' end, as shown in Table 1.

To hybridize primers for capture probe synthesis, hybridization solution containing 4×SSC and 0.1% SDS, 2 µM extension primer (the universal domain oligonucleotide) and 2 µM thread joining primer (the capture domain oligonucleotide) was incubated for 4 min at 50° C. Meanwhile the in-house array was attached to a ChipClip (Whatman). The array was subsequently incubated at 50° C. for 30 min at 300 rpm shake with 50 µL of hybridization solution per well.

After incubation, the array was removed from the ChipClip and washed with the 3 following steps: 1) 50° C. 2×SSC solution with 0.1% SDS for 6 min at 300 rpm shake; 2) 0.2×SSC for 1 min at 300 rpm shake; and 3) 0.1×SSC for 1 min at 300 rpm shake. The array was then spun dry and placed back in the ChipClip.

For extension and ligation reaction (to generate the positional domain of the capture probe) 50 µL of enzyme mix containing 10× Ampligase buffer, 2.5 U AmpliTaq DNA Polymerase Stoffel Fragment (Applied Biosystems), 10 U Ampligase (Epicentre Biotechnologies), dNTPs 2 mM each (Fermentas) and water, was pipetted to each well. The array was subsequently incubated at 55° C. for 30 min. After incubation the array was washed according to the previously described array washing method but the first step has the duration of 10 min instead of 6 min.

The method is depicted in FIG. 1.

Tissue Preparation

The following experiments demonstrate how tissue sample sections may be prepared for use in the methods of the invention.

Preparation of Fresh Frozen Tissue and Sectioning onto Capture Probe Arrays

Fresh non-fixed mouse brain tissue was trimmed if necessary and frozen down in −40° C. cold isopentane and subsequently mounted for sectioning with a cryostat at 10 µm. A slice of tissue was applied onto each capture probe array to be used.

Preparation of Formalin-Fixed Paraffin-Embedded (FFPE) Tissue

Mouse brain tissue was fixed in 4% formalin at 4° C. for 24 h. After that it was incubated as follows: 3× incubation in 70% ethanol for 1 hour; 1× incubation in 80% ethanol for 1 hour; 1× incubation in 96% ethanol for 1 hour; 3× incubation in 100% ethanol for 1 hour; and 2× incubation in xylene at room temperature for 1 h.

The dehydrated samples were then incubated in liquid low melting paraffin 52-54° C. for up to 3 hours, during which the paraffin was changed once to wash out residual xylene. Finished tissue blocks were then stored at RT. Sections were then cut at 4 µm in paraffin with a microtome onto each capture probe array to be used.

The sections were dried at 37° C. on the array slides for 24 hours and stored at RT.

Deparaffinization of FFPE Tissue

Formalin fixed paraffinized mouse brain 10 µm sections attached to CodeLink slides were deparaffinized in xylene twice for: 10 min, 99.5% ethanol for 2 min; 96% ethanol for 2 min; 70% ethanol for 2 min; and were then air dried.

cDNA Synthesis

The following experiments demonstrate that mRNA captured on the array from the tissue sample sections may be used as template for cDNA synthesis.

cDNA Synthesis on Chip

A 16 well mask and Chip Clip slide holder from Whatman was attached to a CodeLink slide. The SuperScript™ III One-step RT-PCR System with Platinum® Taq DNA Polymerase from Invitrogen was used when performing the cDNA synthesis. For each reaction 25 µl 2× reaction mix (SuperScript™ III One-step RT-PCR System with Platinum® Taq DNA Polymerase, Invitrogen), 22.5 µl $H_2O$ and 0.5 µl 100×BSA were mixed and heated to 50° C. SuperScript III/Platinum Taq enzyme mix was added to the reaction mix, 2 µl per reaction, and 50 µl of the reaction mix was added to each well on the chip. The chip was incubated at 50° C. for 30 min (Thermomixer Comfort, Eppendorf).

The reaction mix was removed from the wells and the slide was washed with: 2×SSC, 0.1% SDS at 50° C. for 10 min; 0.2×SSC at room temperature for 1 min; and 0.1×SSC at room temperature for 1 min. The chip was then spin dried.

In the case of FFPE tissue sections, the sections could now be stained and visualized before removal of the tissue, see below section on visualization.

Visualization

Hybridization of Fluorescent Marker Probes Prior to Staining

Prior to tissue application fluorescent marker probes were hybridized to features comprising marker oligonucleotides printed on the capture probe array. The fluorescent marker probes aid in the orientation of the resulting image after tissue visualization, making it possible to combine the image with the resulting expression profiles for individual capture probe "tag" (positional domain) sequences obtained after sequencing. To hybridize fluorescent probes a hybridization solution containing 4×SSC and 0.1% SDS, 2 µM detection probe (P) was incubated for 4 min at 50° C. Meanwhile the in-house array was attached to a ChipClip (Whatman). The array was subsequently incubated at 50° C. for 30 min at 300 rpm shake with 50 µL of hybridization solution per well.

After incubation, the array was removed from the Chip-Clip and washed with the 3 following steps: 1) 50° C. 2×SSC solution with 0.1% SDS for 6 min at 300 rpm shake, 2) 0.2×SSC for 1 min at 300 rpm shake and 3) 0.1×SSC for 1 min at 300 rpm shake. The array was then spun dry.

General Histological Staining of FFPE Tissue Sections Prior to or Post cDNA Synthesis FFPE tissue sections immobilized on capture probe arrays were washed and rehydrated after deparaffinization prior to cDNA synthesis as described previously, or washed after cDNA synthesis as described previously. They are then treated as follows: incubate for 3 minutes in Hematoxylin; rinse with deionized water; incubate 5 minutes in tap water; rapidly dip 8 to 12 times in acid ethanol; rinse 2×1 minute in tap water; rinse 2 minutes in deionized water; incubate 30 seconds in Eosin; wash 3×5 minutes in 95% ethanol; wash 3×5 minutes in 100% ethanol; wash 3×10 minutes in xylene (can be done overnight); place coverslip on slides using DPX; dry slides in the hood overnight.

General Immunohistochemistry Staining of a Target Protein in FFPE Tissue Sections Prior to or Post cDNA Synthesis FFPE tissue sections immobilized on capture probe arrays were washed and rehydrated after deparaffinization prior to cDNA synthesis as described previously, or washed after cDNA synthesis as described previously. They were then treated as follows without being allowed to dry during the whole staining process: sections were incubated with primary antibody (dilute primary antibody in blocking solution comprising 1× Tris Buffered Saline (50 mM Tris, 150 mM NaCl, pH 7.6), 4% donkey serum and 0.1% triton-x) in a wet chamber overnight at RT; rinse three times with 1×TBS; incubate section with matching secondary antibody conjugated to a fluorochrome (FITC, Cy3 or Cy5) in a wet chamber at RT for 1 hour. Rinse 3× with 1×TBS, remove as much as possible of TBS and mount section with ProLong Gold+DAPI (Invitrogen) and analyze with fluorescence microscope and matching filter sets.

Removal of Residual Tissue

Frozen Tissue

For fresh frozen mouse brain tissue the washing step directly following cDNA synthesis was enough to remove the tissue completely.

FFPE Tissue

The slides with attached formalin fixed paraffinized mouse brain tissue sections were attached to ChipClip slide holders and 16 well masks (Whatman). For each 150 µl Proteinase K Digest Buffer from the RNeasy FFPE kit (Qiagen), 10 µl Proteinase K Solution (Qiagen) was added. 50 µl of the final mixture was added to each well and the slide was incubated at 56° C. for 30 min.

Capture Probe (cDNA) Release

Capture Probe Release with Uracil Cleaving USER Enzyme Mixture in PCR Buffer (Covalently Attached Probes)

A 16 well mask and CodeLink slide was attached to the ChipClip holder (Whatman). 50 µl of a mixture containing 1× FastStart High Fidelity Reaction Buffer with 1.8 mM MgCl2 (Roche), 200 µM dNTPs (New England Biolabs) and 0.1 U/1 µl USER Enzyme (New England Biolabs) was heated to 37° C. and was added to each well and incubated at 37° C. for 30 min with mixing (3 seconds at 300 rpm, 6 seconds at rest) (Thermomixer comfort; Eppendorf). The reaction mixture containing the released cDNA and probes was then recovered from the wells with a pipette.

Capture Probe Release with Uracil Cleaving USER Enzyme Mixture in TdT (Terminal Transferase) Buffer (Covalently Attached Probes)

50 µl of a mixture containing: 1× TdT buffer (20 mM Tris-acetate (pH 7.9), 50 mM Potassium Acetate and 10 mM Magnesium Acetate) (New England Biolabs, www.neb.com); 0.1 µg/µl BSA (New England Biolabs); and 0.1 U/µl USER Enzyme (New England Biolabs) was heated to 37° C. and was added to each well and incubated at 37° C. for 30 min with mixing (3 seconds at 300 rpm, 6 seconds at rest) (Thermomixer comfort; Eppendorf). The reaction mixture containing the released cDNA and probes was then recovered from the wells with a pipette.

Capture Probe Release with Boiling Hot Water (Covalently Attached Probes)

A 16 well mask and CodeLink slide was attached to the ChipClip holder (Whatman). 50 µl of 99° C. water was pipetted into each well. The 99° C. water was allowed to react for 30 minutes. The reaction mixture containing the released cDNA and probes was then recovered from the wells with a pipette.

Capture Probe Release with Heated PCR Buffer (Hybridized In Situ Synthesized Capture Probes, i.e. Capture Probes Hybridized to Surface Probes)

50 µl of a mixture containing: 1× TdT buffer (20 mM Tris-acetate (pH 7.9), 50 mM Potassium Acetate and 10 mM Magnesium Acetate) (New England Biolabs, www.neb.com); 0.1 µg/µl BSA (New England Biolabs); and 0.1 U/µl USER Enzyme (New England Biolabs) was preheated to 95° C. The mixture was then added to each well and incubated for 5 minutes at 95° C. with mixing (3 seconds at 300 rpm, 6 seconds at rest) (Thermomixer comfort; Eppendorf). The reaction mixture containing the released probes was then recovered from the wells.

Capture Probe Release with Heated TdT (Terminal Transferase) Buffer (Hybridized In Situ Synthesized Capture Probes, i.e. Capture Probes Hybridized to Surface Probes)

50 µl of a mixture containing: 1× TdT buffer (20 mM Tris-acetate (pH 7.9), 50 mM Potassium Acetate and 10 mM Magnesium Acetate) (New England Biolabs, www.neb.com); 0.1 µg/µl BSA (New England Biolabs); and 0.1 U/µl USER Enzyme (New England Biolabs) was preheated to 95° C. The mixture was then added to each well and incubated for 5 minutes at 95° C. with mixing (3 seconds at 300 rpm, 6 seconds at rest) (Thermomixer comfort; Eppendorf). The reaction mixture containing the released probes was then recovered from the wells.

Figure 3:
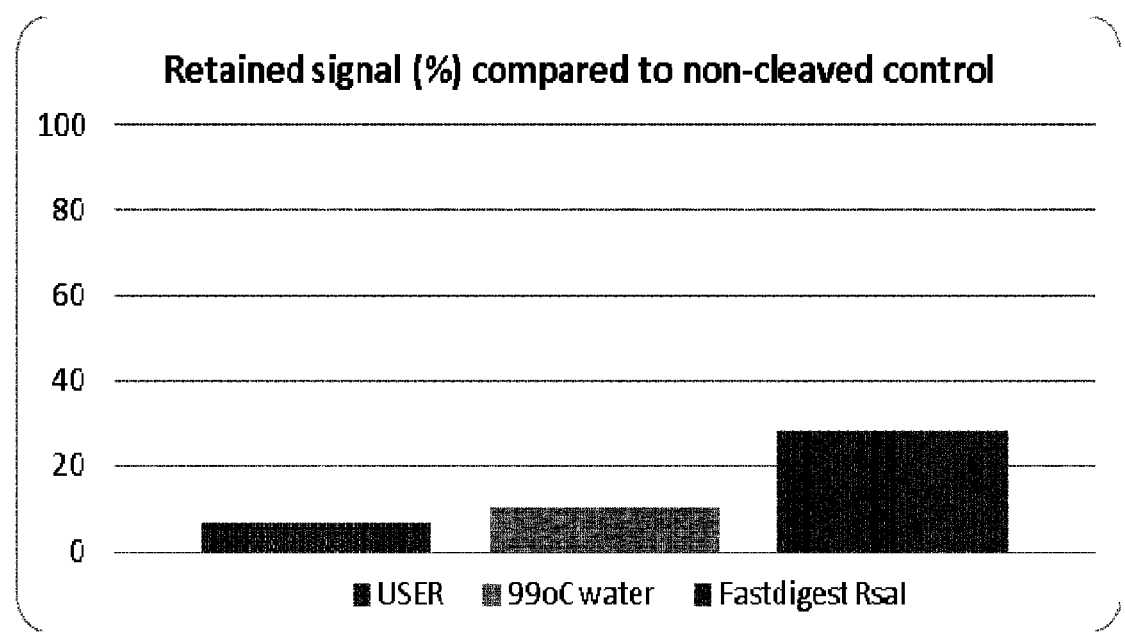
FIG. 3 shows a bar chart demonstrating the efficiency of enzymatic cleavage (USER or RsaI) from in-house manufactured arrays and by 99° C. water from Agilent manufactured arrays, as measured by hybridization of fluorescently labelled probes to the array surface after probe release.
Figure 4:
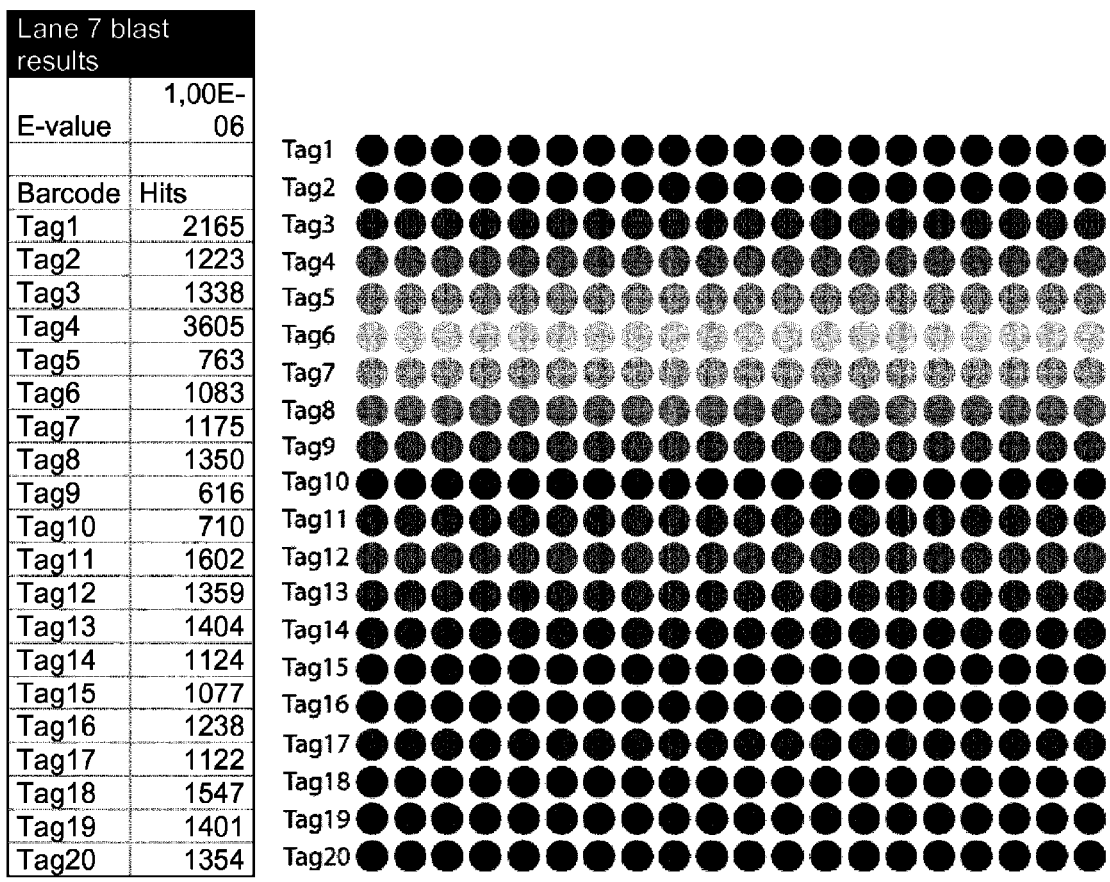
FIG. 4 shows a table that lists the reads sorted for their origin across the low density in-house manufactured DNA-capture array as seen in the schematic representation.
Figure 5:
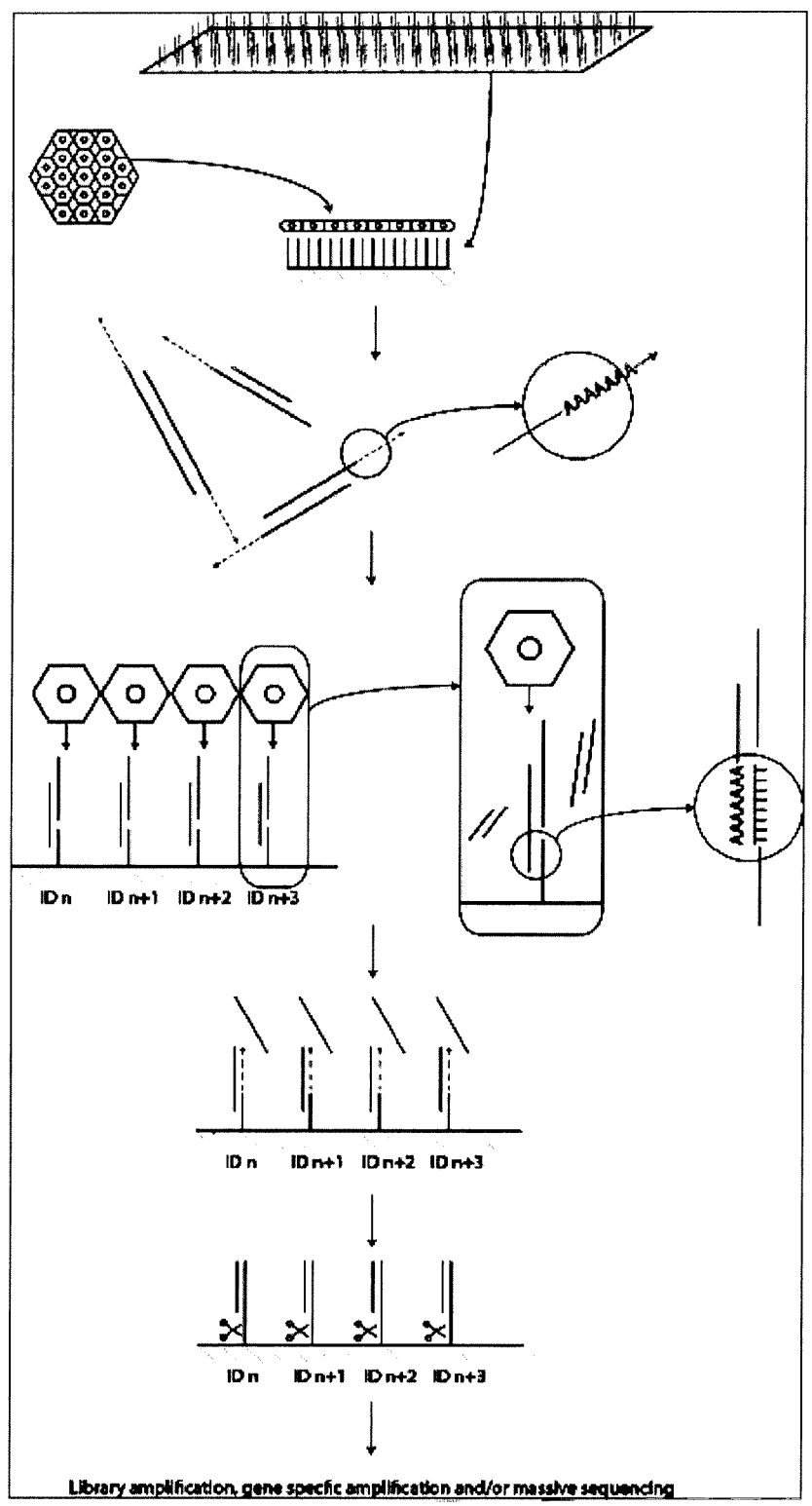
FIG. 5 shows a schematic illustration of the principle of the method described in Example 4, i.e. use of microarrays with immobilized DNA oligos (capture probes) carrying spatial labelling tag sequences (positional domains). Each feature of oligos of the microarray carries a 1) a unique labelling tag (positional domain) and 2) a capture sequence (capture domain).

The efficacy of treating the array with the USER enzyme and water heated to 99° C. can be seen in FIG. 3. Enzymatic cleavage using the USER enzyme and the Rsal enzyme was performed using the "in-house" arrays described above (FIG. 3). Hot water mediated release of DNA surface probes was also performed using commercial arrays manufactured by Agilent.

Probe Collection and Linker Introduction

The experiments demonstrate that first strand cDNA released from the array surface may be modified to produce double stranded DNA and subsequently amplified.

Whole Transcriptome Amplification by the Picoplex Whole Genome Amplification Kit (Capture Probe Sequences Including Positional Domain (Taq) Sequences not Retained at the Edge of the Resulting dsDNA)

Capture probes were released with uracil cleaving USER enzyme mixture in PCR buffer (covalently attached capture probes) or with heated PCR buffer (hybridized in situ synthesized capture probes, i.e. capture probes hybridized to surface probes).

The released cDNA was amplified using the Picoplex (Rubicon Genomics) random primer whole genome amplification method, which was carried out according to manufacturers instructions.

Whole Transcriptome Amplification by dA Tailing with Terminal Transferase (TdT) (Capture Probe Sequences Including Positional Domain (Tag) Sequences Retained at the End of the Resulting dsDNA)

Capture probes were released with uracil cleaving USER enzyme mixture in TdT (terminal transferase) buffer (covalently attached capture probes) or with heated TdT (terminal transferase) buffer (hybridized in situ synthesized capture probes, i.e. capture probes hybridized to surface probes).

38 µl of cleavage mixture was placed in a clean 0.2 ml PCR tube. The mixture contained: 1× TdT buffer (20 mM Tris-acetate (pH 7.9), 50 mM Potassium Acetate and 10 mM Magnesium Acetate) (New England Biolabs, www.neb.com), 0.1 µg/µl BSA (New England Biolabs); 0.1 U/µl USER Enzyme (New England Biolabs) (not for heated release); released cDNA (extended from surface probes); and released surface probes. To the PCR tube, 0.5 µl RNase H (5 U/µl, final concentration of 0.06 U/µl), 1 µl TdT (20 U/µl, final concentration of 0.5 U/µl), and 0.5 µl dATPs (100 mM, final concentration of 1.25 mM), were added. For dA tailing, the tube was incubated in a thermocycler (Applied Biosystems) at 37° C. for 15 min followed by an inactivation of TdT at 70° C. for 10 min. After dA tailing, a PCR master mix was prepared. The mix contained: 1× Faststart HiFi PCR Buffer (pH 8.3) with 1.8 mM $MgCl_2$ (Roche); 0.2 mM of each dNTP (Fermentas); 0.2 µM of each primer, A (complementary to the amplification domain of the capture probe) and B_(dT)24 (Eurofins MWG Operon) (complementary to the poly-A tail to be added to the 3' end of the first cDNA strand); and 0.1 U/µl Faststart HiFi DNA polymerase (Roche). 23 µl of PCR Master mix was placed into nine clean 0.2 ml PCR tubes. 2 µl of dA tailing mixture were added to eight of the tubes, while 2 µl water (RNase/DNase free) was added to the last tube (negative control). PCR amplification was carried out with the following program: Hot start at 95° C. for 2 minutes, second strand synthesis at 50° C. for 2 minutes and 72° C. for 3 minutes, amplification with 30 PCR cycles at 95° C. for 30 seconds, 65° C. for 1 minutes, 72° C. for 3 minutes, and a final extension at 72° C. for 10 minutes.

Post-Reaction Cleanup and Analysis

Four amplification products were pooled together and were processed through a Qiaquick PCR purification column (Qiagen) and eluted into 30 µl EB (10 mM Tris-Cl, pH 8.5). The product was analyzed on a Bioanalyzer (Agilent). A DNA 1000 kit was used according to manufacturers instructions.

Sequencing

Illumina Sequencing dsDNA library for Illumina sequencing using sample indexing was carried out according to manufacturers instructions. Sequencing was carried out on an HiSeq2000 platform (Illumina).

Bioinformatics

Obtaining Digital Transcriptomic Information from Sequencing Data from Whole Transcriptome Libraries Amplified Using the dA Tailing Terminal Transferase Approach The sequencing data was sorted through the FastX toolkit FASTQ Barcode splitter tool into individual files for the respective capture probe positional domain (tag) sequences. Individually tagged sequencing data was then analyzed through mapping to the mouse genome with the Tophat mapping tool. The resulting SAM file was processed for transcript counts through the HTseq-count software.

Obtaining Digital Transcriptomic Information from Sequencing Data from Whole Transcriptome Libraries Amplified Using the Picoplex Whole Genome Amplification Kit Approach The sequencing data was converted from FASTQ format to FASTA format using the FastX toolkit FASTQ-to-FASTA converter. The sequencing reads was aligned to the capture probe positional domain (tag) sequences using Blastn and the reads with hits better than $1e^{-6}$ to one of tag sequences were sorted out to individual files for each tag sequence respectively. The file of tag sequence reads was then aligned using Blastn to the mouse transcriptome, and hits were collected.

Combining Visualization Data and Expression Profiles

The expression profiles for individual capture probe positional domain (tag) sequences are combined with the spatial information obtained from the tissue sections through staining. Thereby the transcriptomic data from the cellular compartments of the tissue section can be analyzed in a directly comparative fashion, with the availability to distinguish distinct expression features for different cellular subtypes in a given structural context

Example 2

Stained FFPE mouse brain tissue (olfactory bulb) sections were placed on top of a bar-coded transcriptome capture array, according to the general procedure described in Example 1. As compared with the experiment with fresh frozen tissue in Example 1, better morphology was observed with the FFPE tissue.

Example 3

Whole Transcriptome Amplification by Random Primer Second Strand Synthesis Followed by Universal Handle Amplification (Capture Probe Sequences Including Taq Sequences Retained at the End of the Resulting dsDNA)

Following capture probe release with uracil cleaving USER enzyme mixture in PCR buffer (covalently attached probes)
OR Following capture probe release with heated PCR buffer (hybridized in situ synthesized capture probes)

1 µl RNase H (5 U/µl) was added to each of two tubes, final concentration of 0.12 U/µl, containing 40 µl× Faststart HiFi PCR Buffer (pH 8.3) with 1.8 mM MgCl$_2$ (Roche, www.roche-applied-science.com), 0.2 mM of each dNTP (Fermentas, www.fermentas.com), 0.1 µg/µl BSA (New England Biolabs, www.neb.com), 0.1 U/µl USER Enzyme (New England Biolabs), released cDNA (extended from surface probes) and released surface probes. The tubes were incubated at 37° C. for 30 min followed by 70° C. for 20 min in a thermo cycler (Applied Biosystems, www.appliedbiosystems.com). 1 µl Klenow Fragment (3' to 5' exo minus) (Illumina, www.illumina.com) and 1 µl handle coupled random primer (10 µM) (Eurofins MWG Operon, www.eurofinsdna.com) was added to the two tubes (B_R8 (octamer) to one of the tubes and B_R6 (hexamer) to the other tube), final concentration of 0.23 µM. The two tubes were incubated at 15° C. for 15 min, 25° C. for 15 min, 37° C. for 15 min and finally 75° C. for 20 min in a thermo cycler (Applied Biosystems). After the incubation, 1 µl of each primer, A_P and B (10 µM) (Eurofins MWG Operon), was added to both tubes, final concentration of 0.22 µM each. 1 µl Faststart HiFi DNA polymerase (5 U/µl) (Roche) was also added to both tubes, final concentration of 0.11 U/µl. PCR amplification were carried out in a thermo cycler (Applied Biosystems) with the following program: Hot start at 94° C. for 2 min, followed by 50 cycles at 94° C. for 15 seconds, 55° C. for 30 seconds, 68° C. for 1 minute, and a final extension at 68° C. for 5 minutes. After the amplification, 40 µl from each of the two tubes were purified with Qiaquick PCR purification columns (Qiagen, www.giagen.com) and eluted into 30 µl EB (10 mM Tris-Cl, pH 8.5). The Purified products were analyzed with a Bioanalyzer (Agilent, www.home.agilent.com), DNA 7500 kit were used. This Example demonstrates the use of random hexamer and random octamer second strand synthesis, followed by amplification to generate the population from the released cDNA molecules.

Example 4

Amplification of ID-Specific and Gene Specific Products after cDNA Synthesis and Probe Collection Following capture probe release with uracil cleaving USER enzyme mixture in PCR buffer (covalently attached probes).

The cleaved cDNA was amplified in final reaction volumes of 10 µl. 7 µl cleaved template, 1 µl ID-specific forward primer (2 µM), 1 µl gene-specific reverse primer (2 µM) and 1 µl FastStart High Fidelity Enzyme Blend in 1.4× FastStart High Fidelity Reaction Buffer with 1.8 mM MgCl$_2$ to give a final reaction of 10 µl with 1× FastStart High Fidelity Reaction Buffer with 1.8 mM MgCl$_2$ and 1 U FastStart High Fidelity Enzyme Blend. PCR amplification were carried out in a thermo cycler (Applied Biosystems) with the following program: Hot start at 94° C. for 2 min, followed by 50 cycles at 94° C. for 15 seconds, 55° C. for 30 seconds, 68° C. for 1 minute, and a final extension at 68° C. for 5 minutes.

Primer sequences, resulting in a product of approximately 250 bp,

```
Beta-2 microglobulin (B2M) primer
                           (SEQ ID NO: 43)
5'-TGGGGGTGAGAATTGCTAAG-3'

ID-1 primer
                           (SEQ ID NO: 44)
5'-CCTTCTCCTTCTCCTTCACC-3'

ID-5 primer
                           (SEQ ID NO: 45)
5'-GTCCTCTATTCCGTCACCAT-3'

ID-20 primer
                           (SEQ ID NO: 46)
5'-CTGCTTCTTCCTGGAACTCA-3'
```

The results show successful amplification of ID-specific and gene-specific products using two different ID primers (i.e. specific for ID tags positioned at different locations on the microarray and the same gene specific primer from a brain tissue covering all the probes). Accordingly this experiment establishes that products may be identified by an ID tag-specific or target nucleic acid specific amplification reaction. It is further established that different ID tags may be distinguished. A second experiment, with tissue covering only half of the ID probes (i.e. capture probes) on the array resulted in a positive result (PCR product) for spots that were covered with tissue.

Example 5

Alternative Synthesis of 5' to 3' Oriented Capture Probes Using Polymerase Extension and Terminal Transferase Tailing

To hybridize primers for capture probe synthesis hybridization solution containing 4×SSC and 0.1% SDS and 2 µM extension primer (A_primer) was incubated for 4 min at 50° C. Meanwhile the in-house array (see Example 1) was attached to a ChipClip (Whatman). The array was subsequently incubated at 50° C. for 30 min at 300 rpm shake with 50 µL of hybridization solution per well.

After incubation, the array was removed from the Chip-Clip and washed with the 3 following steps: 1) 50° C. 2×SSC solution with 0.1% SDS for 6 min at 300 rpm shake, 2) 0.2×SSC for 1 min at 300 rpm shake and 3) 0.1×SSC for 1 min at 300 rpm shake. The array was then spun dry and placed back in the ChipClip.

1 µl Klenow Fragment (3' to 5' exo minus) (Illumina, www.illumina.com) together with 10× Klenow buffer, dNTPs 2 mM each (Fermentas) and water, was mixed into a 50 µl reaction and was pipetted into each well.

The array was incubated at 15° C. for 15 min, 25° C. for 15 min, 37° C. for 15 min and finally 75° C. for 20 min in an Eppendorf Thermomixer.

After incubation, the array was removed from the Chip-Clip and washed with the 3 following steps: 1) 50° C. 2×SSC solution with 0.1% SDS for 6 min at 300 rpm shake, 2) 0.2×SSC for 1 min at 300 rpm shake and 3) 0.1×SSC for 1 min at 300 rpm shake. The array was then spun dry and placed back in the ChipClip.

For dT tailing a 50 µl reaction mixture containing 1× TdT buffer (20 mM Tris-acetate (pH 7.9), 50 mM Potassium Acetate and 10 mM Magnesium Acetate) (New England Biolabs, www.neb.com), 0.1 µg/µl BSA (New England Biolabs), 0.5 µl RNase H (5 U/µl), 1 µl TdT (20 U/µl) and 0.5 µl dTTPs (100 mM) was prepared. The mixture was added to the array surface and the array was incubated in a thermo cycler (Applied Biosystems) at 37° C. for 15 min followed by an inactivation of TdT at 70° C. for 10 min.

Example 6

Spatial Transcriptomics Using 5' to 3' High Probe Density Arrays and Formalin-Fixed Frozen (FF-Frozen) Tissue with USER System Cleavage and Amplification Via Terminal Transferase

Array Preparation

Figure 6:
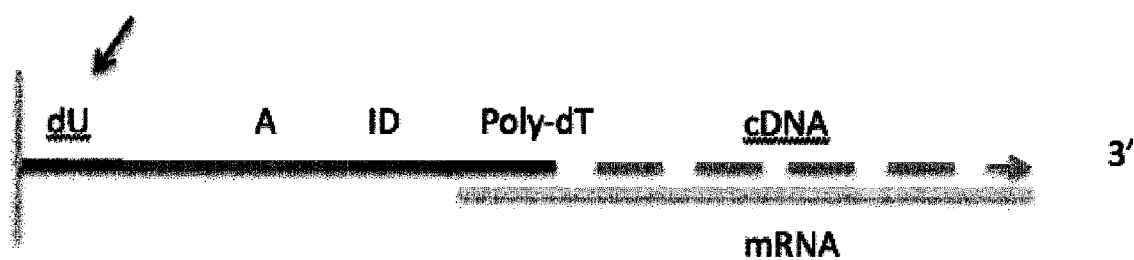
FIG. 6 shows the composition of 5' to 3' oriented capture probes used on high-density capture arrays.

Pre-fabricated high-density microarrays chips were ordered from Roche-Nimblegen (Madison, Wis., USA). Each capture probe array contained 135,000 features of which 132,640 features carried a capture probe comprising a unique ID-tag sequence (positional domain) and a capture region (capture domain). Each feature was 13×13 µm in size. The capture probes were composed 5' to 3' of a universal domain containing five dUTP bases (a cleavage domain) and a general amplification domain, an ID tag (positional domain) and a capture region (capture domain) (FIG. 6 and Table 4). Each array was also fitted with a frame of marker probes carrying a generic 30 bp sequence (Table 4) to enable hybridization of fluorescent probes to help with orientation during array visualization.

Tissue Preparation—Preparation of Formalin-Fixed Frozen Tissue

The animal (mouse) was perfused with 50 ml PBS and 100 ml 4% formalin solution. After excision of the olfactory bulb, the tissue was put into a 4% formalin bath for post-fixation for 24 hrs. The tissue was then sucrose treated in 30% sucrose dissolved in PBS for 24 hrs to stabilize morphology and to remove excess formalin. The tissue was frozen at a controlled rate down to −40° C. and kept at −20° C. between experiments. Similar preparation of tissue post-fixed for 3 hrs or without post-fixation was carried out for a parallel specimen. Perfusion with 2% formalin without post-fixation was also used successfully. Similarly the sucrose treatment step could be omitted. The tissue was mounted into a cryostat for sectioning at 10 µm. A slice of tissue was applied onto each capture probe array to be used. Optionally for better tissue adherence, the array chip was placed at 50° C. for 15 minutes.

Optional Control—Total RNA Preparation from Sectioned Tissue

Total RNA was extracted from a single tissue section (10 µm) using the RNeasy FFPE kit (Qiagen) according to manufacturers instructions. The total RNA obtained from the tissue section was used in control experiments for a comparison with experiments in which the RNA was captured on the array directly from the tissue section. Accordingly, in the case where total RNA was applied to the array the staining, visualization and degradation of tissue steps were omitted.

On-Chip Reactions

The hybridization of marker probe to the frame probes, reverse transcription, nuclear staining, tissue digestion and probe cleavage reactions were all performed in a 16 well silicone gasket (ArrayIt, Sunnyvale, Calif., USA) with a reaction volume of 50 µl per well. To prevent evaporation, the cassettes were covered with plate sealers (In Vitro AB, Stockholm, Sweden).

Optional—Tissue Permeabilization Prior to cDNA Synthesis

For permeabilization using Proteinase K, proteinase K (Qiagen, Hilden, Germany) was diluted to 1 µg/ml in PBS. The solution was added to the wells and the slide incubated at room temperature for 5 minutes, followed by a gradual increase to 80° C. over 10 minutes. The slide was washed briefly in PBS before the reverse transcription reaction.

Alternatively for permeabilization using microwaves, after tissue attachment, the slide was placed at the bottom of a glass jar containing 50 ml 0.2×SSC (Sigma-Aldrich) and was heated in a microwave oven for 1 minute at 800 W. Directly after microwave treatment the slide was placed onto a paper tissue and was dried for 30 minutes in a chamber protected from unnecessary air exposure. After drying, the slide was briefly dipped in water (RNase/DNase free) and finally spin-dried by a centrifuge before cDNA synthesis was initiated.

cDNA Synthesis

For the reverse transcription reaction the SuperScript III One-Step RT-PCR System with Platinum Taq (Life Technologies/Invitrogen, Carlsbad, Calif., USA) was used. Reverse transcription reactions contained 1× reaction mix, 1×BSA (New England Biolabs, Ipswich, Mass., USA) and 2 µl SuperScript III RT/Platinum Taq mix in a final volume of 50 µl. This solution was heated to 50° C. before application to the tissue sections and the reaction was performed at 50° C. for 30 minutes. The reverse transcription solution was subsequently removed from the wells and the slide was allowed to air dry for 2 hours.

Tissue Visualization

After cDNA synthesis, nuclear staining and hybridization of the marker probe to the frame probes (probes attached to the array substrate to enable orientation of the tissue sample on the array) was done simultaneously. A solution with DAPI at a concentration of 300 nM and marker probe at a concentration of 170 nM in PBS was prepared. This solution was added to the wells and the slide was incubated at room temperature for 5 minutes, followed by brief washing in PBS and spin drying.

Alternatively the marker probe was hybridized to the frame probes prior to placing the tissue on the array. The marker probe was then diluted to 170 nM in hybridization buffer (4×SSC, 0.1% SDS). This solution was heated to 50° C. before application to the chip and the hybridization was performed at 50° C. for 30 minutes at 300 rpm. After hybridization, the slide was washed in 2×SSC, 0.1% SDS at 50° C. and 300 rpm for 10 minutes, 0.2×SSC at 300 rpm for 1 minute and 0.1×SSC at 300 rpm for 1 minute. In that case the staining solution after cDNA synthesis only contained the nuclear DAPI stain diluted to 300 nM in PBS. The solution was applied to the wells and the slide was incubated at room temperature for 5 minutes, followed by brief washing in PBS and spin drying.

The sections were microscopically examined with a Zeiss Axio Imager Z2 and processed with MetaSystems software.

Tissue Removal

The tissue sections were digested using Proteinase K diluted to 1.25 µg/µl in PKD buffer from the RNeasy FFPE Kit (both from Qiagen) at 56° C. for 30 minutes with an interval mix at 300 rpm for 3 seconds, then 6 seconds rest. The slide was subsequently washed in 2×SSC, 0.1% SDS at 50° C. and 300 rpm for 10 minutes, 0.2×SSC at 300 rpm for 1 minute and 0.1×SSC at 300 rpm for 1 minute.

Probe Release

The 16-well Hybridization Cassette with silicone gasket (ArrayIt) was preheated to 37° C. and attached to the Nimblegen slide. A volume of 50 µl of cleavage mixture preheated to 37° C., consisting of Lysis buffer at an unknown concentration (Takara), 0.1 U/µl USER Enzyme (NEB) and 0.1 µg/µl BSA was added to each of wells containing surface immobilized cDNA. After removal of bubbles the slide was sealed and incubated at 37° C. for 30 minutes in a Thermomixer comfort with cycled shaking at 300 rpm for 3 seconds with 6 seconds rest in between. After the incubation 45 µl cleavage mixture was collected from each of the used wells and placed into 0.2 ml PCR tubes.

Library Preparation

Exonuclease Treatment

After cooling the solutions on ice for 2 minutes, Exonuclease I (NEB) was added, to remove unextended cDNA probes, to a final volume of 46.2 µl and a final concentration of 0.52 U/µl. The tubes were incubated in a thermo cycler (Applied Biosystems) at 37° C. for 30 minutes followed by inactivation of the exonuclease at 80° C. for 25 minutes.

dA-Tailing by Terminal Transferase

After the exonuclease step, 45 µl polyA-tailing mixture, according to manufacturers instructions consisting of TdT Buffer (Takara), 3 mM dATP (Takara) and manufacturers TdT Enzyme mix (TdT and RNase H) (Takara), was added to each of the samples. The mixtures were incubated in a thermocycler at 37° C. for 15 minutes followed by inactivation of TdT at 70° C. for 10 minutes.

Second-Strand Synthesis and PCR-Amplification

After dA-tailing, 23 µl PCR master mix was placed into four new 0.2 ml PCR tubes per sample, to each tube 41 µl sample was added as a template. The final PCRs consisted of 1× Ex Taq buffer (Takara), 200 µM of each dNTP (Takara), 600 nM A_primer (MWG), 600 nM B_dT20VN_primer (MWG) and 0.025 U/µl Ex Taq polymerase (Takara)(Table 4). A second cDNA strand was created by running one cycle in a thermocycler at 95° C. for 3 minutes, 50° C. for 2 minutes and 72° C. for 3 minutes. Then the samples were amplified by running 20 cycles (for library preparation) or 30 cycles (to confirm the presence of cDNA) at 95° C. for 30 seconds, 67° C. for 1 minute and 72° C. for 3 minutes, followed by a final extension at 72° C. for 10 minutes.

Library Cleanup

After amplification, the four PCRs (100 µl) were mixed with 500 µl binding buffer (Qiagen) and placed in a Qiaquick PCR purification column (Qiagen) and spun for 1 minute at 17,900×g in order to bind the amplified cDNA to the membrane. The membrane was then washed with wash buffer (Qiagen) containing ethanol and finally eluted into 50 µl of 10 mM Tris-Cl, pH 8.5.

The purified and concentrated sample was further purified and concentrated by CA-purification (purification by superparamagnetic beads conjugated to carboxylic acid) with an MBS robot (Magnetic Biosolutions). A final PEG concentration of 10% was used in order to remove fragments below 150-200 bp. The amplified cDNA was allowed to bind to the CA-beads (Invitrogen) for 10 min and were then eluted into 15 µl of 10 mM Tris-Cl, pH 8.5.

Library Quality Analysis

Samples amplified for 30 cycles were analyzed with an Agilent Bioanalyzer (Agilent) in order to confirm the presence of an amplified cDNA library, the DNA High Sensitivity kit or DNA 1000 kit were used depending on the amount of material.

Sequencing Library Preparation

Library Indexing

Samples amplified for 20 cycles were used further to prepare sequencing libraries. An index PCR master mix was prepared for each sample and 23 µl was placed into six 0.2 ml tubes. 2 µl of the amplified and purified cDNA was added to each of the six PCRs as template making the PCRs containing 1× Phusion master mix (Fermentas), 500 nM InPE1.0 (Illumina), 500 nM Index 1-12 (Illumina), and 0.4 nM InPE2.0 (Illumina). The samples were amplified in a thermocycler for 18 cycles at 98° C. for 30 seconds, 65° C. for 30 seconds and 72° C. for 1 minute, followed by a final extension at 72° C. for 5 minutes.

Sequencing Library Cleanup

After amplification, the six PCRs (150 µl) were mixed with 750 µl binding buffer and placed in a Qiaquick PCR purification column and spun for 1 minute at 17,900×g in order to bind the amplified cDNA to the membrane (because of the large sample volume (900 µl), the sample was split in two (each 450 µl) and was bound in two separate steps). The membrane was then washed with wash buffer containing ethanol and finally eluted into 50 µl of 10 mM Tris-Cl, pH 8.5.

The purified and concentrated sample was further purified and concentrated by CA-purification with an MBS robot. A final PEG concentration of 7.8% was used in order to remove fragments below 300-350 bp. The amplified cDNA was allowed to bind to the CA-beads for 10 min and were then eluted into 15 µl of 10 mM Tris-Cl, pH 8.5. Samples were analyzed with an Agilent Bioanalyzer in order to confirm the presence and size of the finished libraries, the DNA High Sensitivity kit or DNA 1000 kit were used according to manufacturers instructions depending on the amount of material.

Sequencing

The libraries were sequenced on the Illumina Hiseq2000 or Miseq depending on desired data throughput according to manufacturers instructions. Optionally for read 2, a custom sequencing primer B_r2 was used to avoid sequencing through the homopolymeric stretch of 20 T.

Data Analysis

Read 1 was trimmed 42 bases at 5' end. Read 2 was trimmed 25 bases at 5' end (optionally no bases were trimmed from read 2 if the custom primer was used). The reads were then mapped with bowtie to the repeat masked *Mus musculus* 9 genome assembly and the output was formatted in the SAM file format. Mapped reads were extracted and annotated with UCSC refGene gene annotations. Indexes were retrieved with 'indexFinder' (an inhouse software for index retrieval). A mongo DB database was then created containing information about all caught transcripts and their respective index position on the chip.

Figure 7:
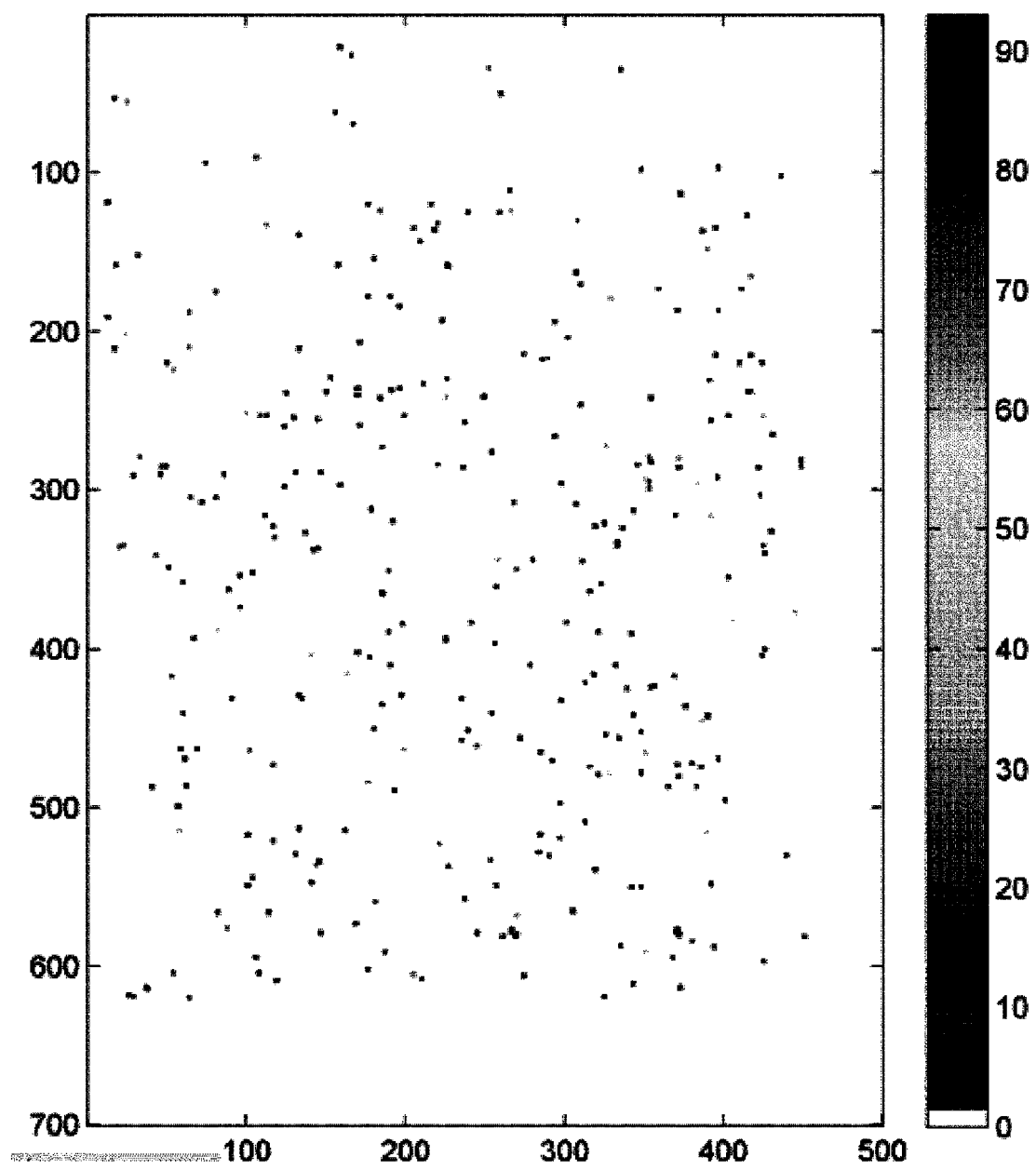
FIG. 7 shows a Matlab visualization of captured transcripts from total RNA extracted from mouse olfactory bulb.

A matlab implementation was connected to the database and allowed for spatial visualization and analysis of the data (FIG. 7).

Optionally the data visualization was overlaid with the microscopic image using the fluorescently labelled frame probes for exact alignment and enabling spatial transcriptomic data extraction.

Example 7

Spatial Transcriptomics Using 3' to 5' High Probe Density Arrays and FFPE Tissue with MutY System Cleavage and Amplification Via TdT Array Preparation Pre-fabricated high-density microarrays chips were ordered from Roche-Nimblegen (Madison, Wis., USA). Each used capture probe array contained 72 k features out of which 66,022 contained a unique ID-tag complementary sequence. Each feature was 16×16 µm in size. The capture probes were composed 3' to 5' in the same way as the probes used for the in-house printed 3' to 5' arrays with the exception to 3 additional bases being added to the upper (P') general handle of the probe to make it a long version of P', LP' (Table 4). Each array was also fitted with a frame of probes carrying a generic 30 bp sequence to enable hybridization of fluorescent probes to help with orientation during array visualization.

Synthesis of 5' to 3' Oriented Capture Probes

The synthesis of 5' to 3' oriented capture probes on the high-density arrays was carried out as in the case with in-house printed arrays, with the exception that the extension and ligation steps were carried out at 55° C. for 15 mins followed by 72° C. for 15 mins. The A-handle probe (Table 4) included an A/G mismatch to allow for subsequent release of probes through the MutY enzymatic system described below. The P-probe was replaced by a longer LP version to match the longer probes on the surface.

Preparation of Formalin-Fixed Paraffin-Embedded Tissue and Deparaffinization

This was carried out as described above in the in-house protocol.

cDNA Synthesis and Staining cDNA synthesis and staining was carried out as in the protocol for 5' to 3' oriented high-density Nimblegen arrays with the exception that biotin labelled dCTPs and dATPs were added to the cDNA synthesis together with the four regular dNTPs (each was present at 25× times more than the biotin labelled ones).

Tissue Removal

Tissue removal was carried out in the same way as in the protocol for 5' to 3' oriented high-density Nimblegen arrays described in Example 6.

Probe Cleavage by MutY

A 16-well Incubation chamber with silicone gasket (ArrayIT) was preheated to 37° C. and attached to the Codelink slide. A volume of 50 µl of cleavage mixture preheated to 37° C., consisting of 1× Endonuclease VIII Buffer (NEB), 10 U/µl MutY (Trevigen), 10 U/µl Endonuclease VIII (NEB), 0.1 µg/µl BSA was added to each of wells containing surface immobilized cDNA. After removal of bubbles the slide was sealed and incubated at 37° C. for 30 minutes in a Thermomixer comfort with cycled shaking at 300 rpm for 3 seconds with 6 seconds rest in between. After the incubation, the plate sealer was removed and 40 µl cleavage mixture was collected from each of the used wells and placed into a PCR plate.

Library Preparation

Biotin-Streptavidin Mediated Library Cleanup

To remove unextended cDNA probes and to change buffer, the samples were purified by binding the biotin labeled cDNA to streptavidin coated C1-beads (Invitrogen) and washing the beads with 0.1M NaOH (made fresh). The purification was carried out with an MBS robot (Magnetic Biosolutions), the biotin labelled cDNA was allowed to bind to the C1-beads for 10 min and was then eluted into 20 µl of water by heating the bead-water solution to 80° C. to break the biotin-streptavidin binding.

dA-Tailing by Terminal Transferase

After the purification step, 18 µl of each sample was placed into new 0.2 ml PCR tubes and mixed with 22 µl of a polyA-tailing master mix leading to a 40 µl reaction mixture according to manufacturers instructions consisting of lysis buffer (Takara, Cellamp Whole Transcriptome Amplification kit), TdT Buffer (Takara), 1.5 mM dATP (Takara) and TdT Enzyme mix (TdT and RNase H) (Takara). The mixtures were incubated in a thermocycler at 37° C. for 15 minutes followed by inactivation of TdT at 70° C. for 10 minutes.

Second-Strand Synthesis and PCR-Amplification

After dA-tailing, 23 µl PCR master mix was placed into four new 0.2 ml PCR tubes per sample, to each tube 41 sample was added as a template. The final PCRs consisted of 1× Ex Taq buffer (Takara), 200 µM of each dNTP (Takara), 600 nM A_primer (MWG), 600 nM B_dT20VN_primer (MWG) and 0.025 U/µl Ex Taq polymerase (Takara). A second cDNA strand was created by running one cycle in a thermo cycler at 95° C. for 3 minutes, 50° C. for 2 minutes and 72° C. for 3 minutes. Then the samples were amplified by running 20 cycles (for library preparation) or 30 cycles (to confirm the presence of cDNA) at 95° C. for 30 seconds, 67° C. for 1 minute and 72° C. for 3 minutes, followed by a final extension at 72° C. for 10 minutes.

Library Cleanup

After amplification, the four PCRs (100 µl) were mixed with 500 µl binding buffer (Qiagen) and placed in a Qiaquick PCR purification column (Qiagen) and spun for 1 minute at 17,900×g in order to bind the amplified cDNA to the membrane. The membrane was then washed with wash buffer (Qiagen) containing ethanol and finally eluted into 50 µl of 10 mM Tris-HCl, pH 8.5.

The purified and concentrated sample was further purified and concentrated by CA-purification (purification by superparamagnetic beads conjugated to carboxylic acid) with an MBS robot (Magnetic Biosolutions). A final PEG concentration of 10% was used in order to remove fragments below 150-200 bp. The amplified cDNA was allowed to bind to the CA-beads (Invitrogen) for 10 min and were then eluted into 15 µl of 10 mM Tris-HCl, pH 8.5.

Second PCR-Amplification

The final PCRs consisted of 1× Ex Taq buffer (Takara), 200 µM of each dNTP (Takara), 600 nM A_primer (MWG), 600 nM B_ primer (MWG) and 0.025 U/µl Ex Taq polymerase (Takara). The samples were heated to 95° C. for 3 minutes, and then amplified by running 10 cycles at 95° C. for 30 seconds, 65° C. for 1 minute and 72° C. for 3 minutes, followed by a final extension at 72° C. for 10 minutes.

Second Library Cleanup

After amplification, the four PCRs (100 µl) were mixed with 500 µl binding buffer (Qiagen) and placed in a Qiaquick PCR purification column (Qiagen) and spun for 1 minute at 17,900×g in order to bind the amplified cDNA to the membrane. The membrane was then washed with wash buffer (Qiagen) containing ethanol and finally eluted into 50 µl of 10 mM Tris-Cl, pH 8.5.

The purified and concentrated sample was further purified and concentrated by CA-purification (purification by super-paramagnetic beads conjugated to carboxylic acid) with an MBS robot (Magnetic Biosolutions). A final PEG concentration of 10% was used in order to remove fragments below 150-200 bp. The amplified cDNA was allowed to bind to the CA-beads (Invitrogen) for 10 min and were then eluted into 15 µl of 10 mM Tris-HCl, pH 8.5.

Sequencing Library Preparation

Library Indexing

Samples amplified for 20 cycles were used further to prepare sequencing libraries. An index PCR master mix was prepared for each sample and 23 µl was placed into six 0.2 ml tubes. 2 µl of the amplified and purified cDNA was added to each of the six PCRs as template making the PCRs containing 1× Phusion master mix (Fermentas), 500 nM InPE1.0 (Illumina), 500 nM Index 1-12 (Illumina), and 0.4 nM InPE2.0 (Illumina). The samples were amplified in a thermo cycler for 18 cycles at 98° C. for 30 seconds, 65° C. for 30 seconds and 72° C. for 1 minute, followed by a final extension at 72° C. for 5 minutes.

Sequencing Library Cleanup

After amplification, the samples was purified and concentrated by CA-purification with an MBS robot. A final PEG concentration of 7.8% was used in order to remove fragments below 300-350 bp. The amplified cDNA was allowed to bind to the CA-beads for 10 min and were then eluted into 15 µl of 10 mM Tris-HCl, pH 8.5.

10 µl of the amplified and purified samples were placed on a Caliper XT chip and fragments between 480 bp and 720 bp were cut out with the Caliper XT (Caliper). Samples were analyzed with an Agilent Bioanalyzer in order to confirm the presence and size of the finished libraries, the DNA High Sensitivity kit was used.

Sequencing and Data Analysis

Figure 8:
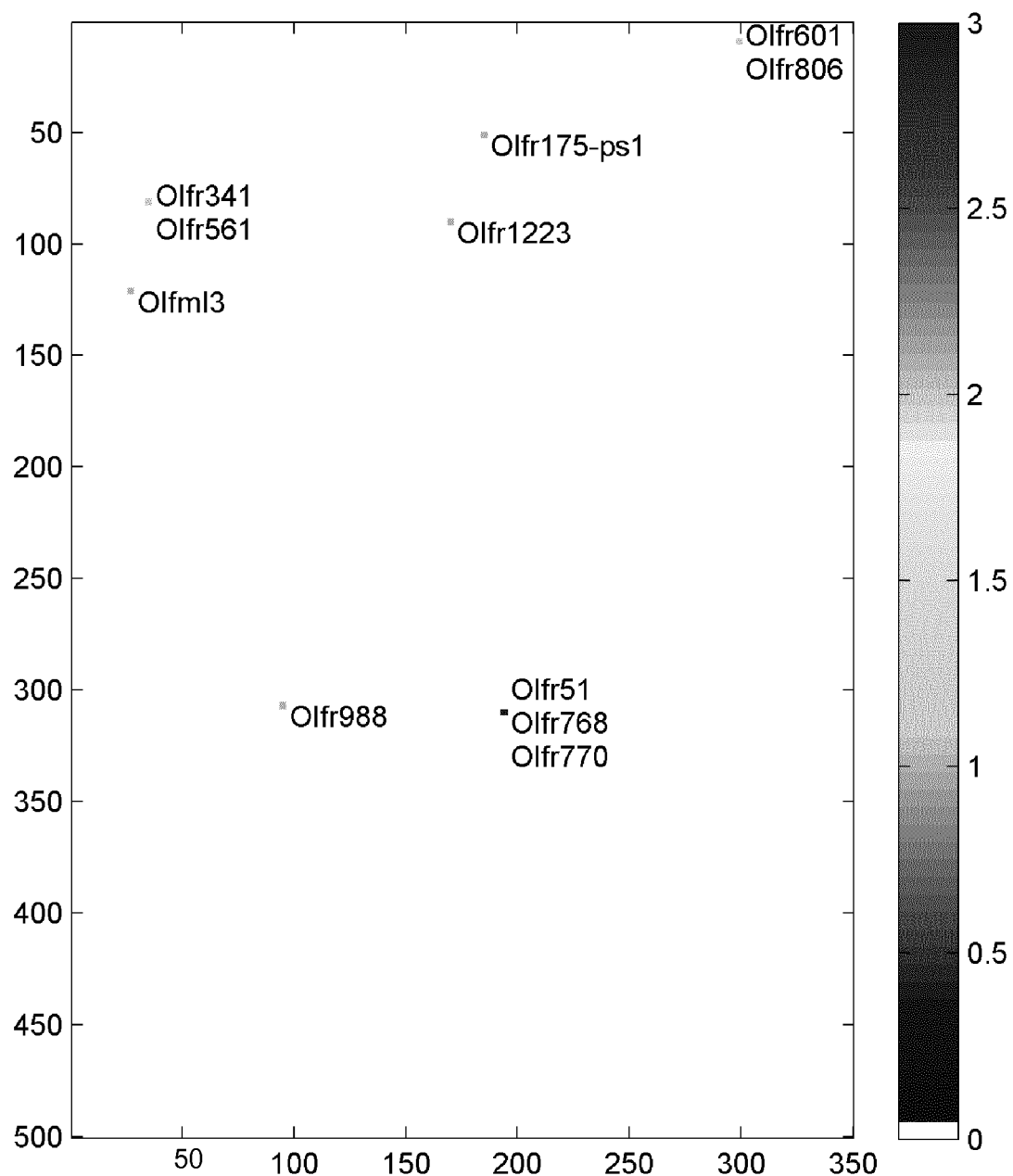
FIG. 8 shows Olfr (olfactory receptor) transcripts as visualized across the capture array using Matlab visualization after capture from mouse olfactory bulb tissue.

Sequencing and Bioinformatic was carried out in the same way as in the protocol for 5' to 3' oriented high-density Nimblegen arrays described in Example 6. However, in the data analysis, read 1 was not used in the mapping of transcripts. Specific Olfr transcripts could be sorted out using the Matlab visualization tool (FIG. 8).

Example 8

Figure 9:
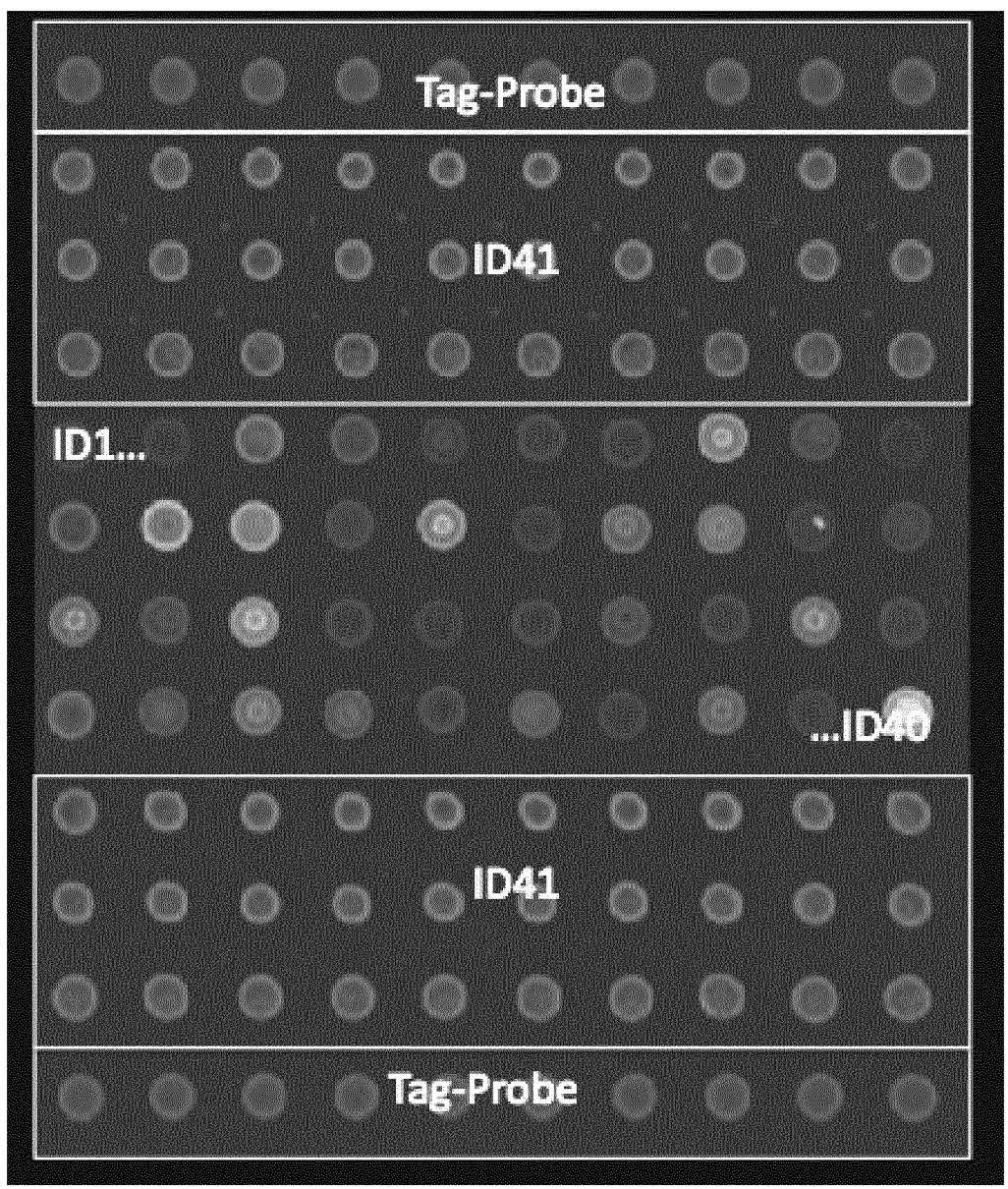
FIG. 9 shows a pattern of printing for in-house 41-ID-tag microarrays.
Figure 10:
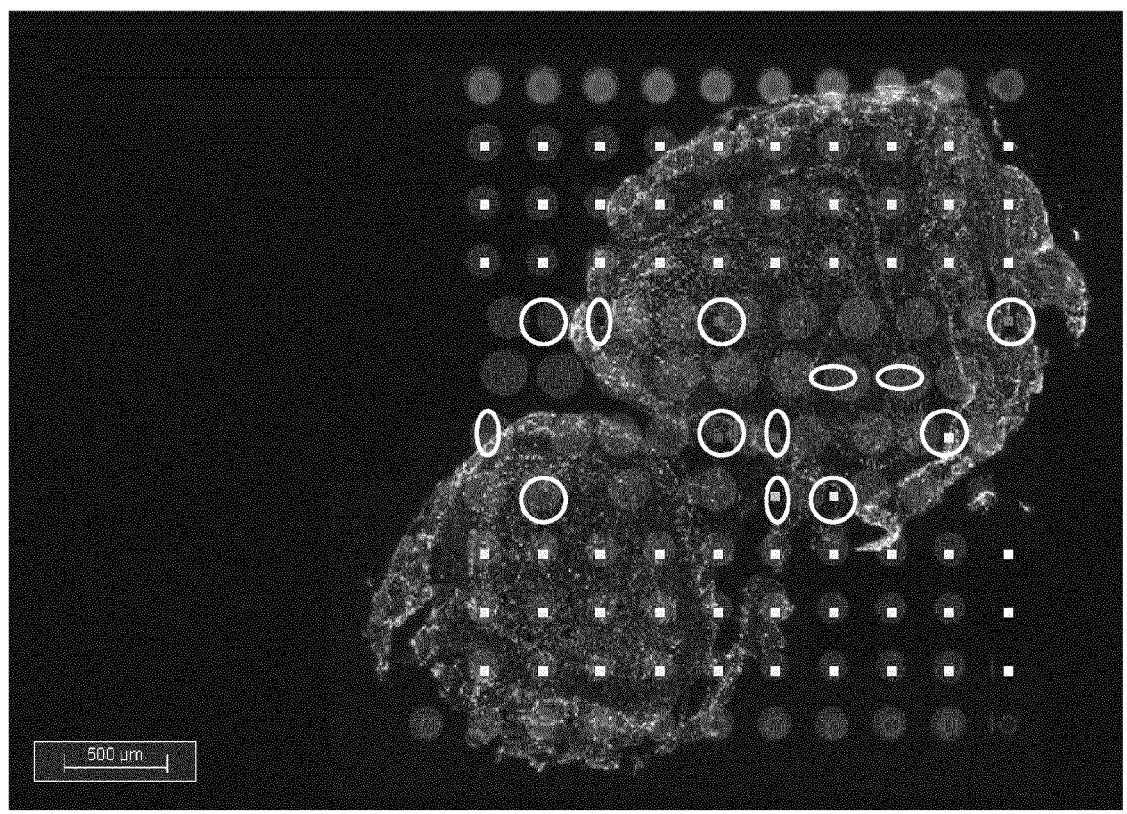
FIG. 10 shows a Matlab visualization of captured ID-tagged transcripts from mouse olfactory bulb tissue on 41-ID-tag in-house arrays overlaid with the tissue image. For clarity, the specific features on which particular genes were identified have been circled.

Spatial Transcriptomics Using in House Printed 41-Taq Microarray with 5' to 3' Oriented Probes and Formalin-Fixed Frozen (FF-Frozen) Tissue with Permeabilization Through ProteinaseK or Microwaving with USER System Cleavage and Amplification Via TdT Array Preparation In-house arrays were printed as previously described but with a pattern of 41 unique ID-tag probes with the same composition as the probes in the 5' to 3' oriented high-density array in Example 6 (FIG. 9).

All other steps were carried out in the same way as in the protocol described in Example 6.

Example 9

Alternative Method for Performing the cDNA Synthesis Step cDNA synthesis on chip as described above can also be combined with template switching to create a second strand by adding a template switching primer to the cDNA synthesis reaction (Table 4). The second amplification domain is introduced by coupling it to terminal bases added by the reverse transcriptase at the 3' end of the first cDNA strand, and primes the synthesis of the second strand. The library can be readily amplified directly after release of the double-stranded complex from the array surface.

Example 10

The following experiments demonstrate how the secured (captured) cDNA molecules can be labelled and detected on the surface of the object substrate, e.g. array.

Preparation of In-House Printed Microarray with 5' to 3' Oriented Probes

The RNA-capture oligonucleotide (Table 2) was printed on glass slides to function as the capture probe. The probe was synthesized with a 5'-terminus amino linker with a C6 spacer. All probes where synthesized by Sigma-Aldrich (St. Louis, Mo., USA). The RNA-capture probe was suspended at a concentration of 20 µM in 150 mM sodium phosphate, pH 8.5 and spotted using a pipette onto CodeLink™ Activated microarray slides (7.5 cm×2.5 cm; Surmodics, Eden Prairie, Minn., USA). Each array was printed with 10 µl of capture probe-containing solution, and left to dry. After printing, surface blocking was performed according to the manufacturer's instructions. The probes were printed in 16 arrays on the slide. The 16 sub-arrays were separated during reaction steps by a 16-pad mask (Arrayit Corporation, Sunnyvale, Calif., USA).

Preparation of Fresh Frozen Tissue and Sectioning onto Capture Probe Arrays

Fresh non-fixed mouse brain tissue was trimmed if necessary and frozen in −40° C. cold isopentane and subsequently mounted for sectioning with a cryostat at 10 µm. A slice of tissue was applied onto each probe array.

Fixation of Tissue Section Using Formalin

50 µl of 4% paraformaldehyde dissolved in PBS was added directly to the probe array to cover the tissue section. The array was incubated at room temperature for 10 minutes and then washed for 10 seconds in PBS. The array was then incubated at 50° C. for 15 minutes.

Permeabilization of the Tissue Sample Using Pepsin and HCl

Pepsin was diluted to 0.1% in 0.1M HCl and was preheated to 37° C. The array was attached to an ArrayIt 16-well mask and holder. 50 µl of the pepsin/HCl mixture was added to each well. The array was incubated for 10 minutes at 37° C. and the wells were washed with 100 µl 0.1×SSC by pipetting.

cDNA Synthesis with Cy3-dNTP

For each well a cDNA synthesis mixture (80 µl) was prepared containing 4 µl each of dATP/dGTP/dTTP (10 mM), 4 µl dCTP (2.5 mM), 4 µl Cy3-dCTP (1 mM), 4 µl DTT (0.1M), 1×BSA, 20 U/µl Superscript III, 5 U/µl RNase-OUT, 1× first strand buffer (Superscript III, Invitrogen) and MilliQ water. 70 µl of the reaction mixture was added to each well. The reactions were covered with a plastic sealer and incubated at 37° C. overnight.

Washing

After incubation the array was removed from the ArrayIt mask and holder and washed using the following steps: 1) 50° C. 2×SSC solution with 0.1% SDS for 10 min at 300 rpm shake; 2) 0.2×SSC for 1 min at 300 rpm shake; and 3) 0.1×SSC for 1 min at 300 rpm shake. The array was spun dry.

Tissue Removal

The array was attached to an ArrayIt slide holder and 16 well mask (ArrayIt Corporation). 10 µl Proteinase K Solution (Qiagen) was added for each 150 µl Proteinase K Digest Buffer from the RNeasy FFPE kit (Qiagen). 50 µl of the final mixture was added to each well and the array was incubated at 56° C. for 1 hour. The array was washed as described above.

Imaging

Figure 11:
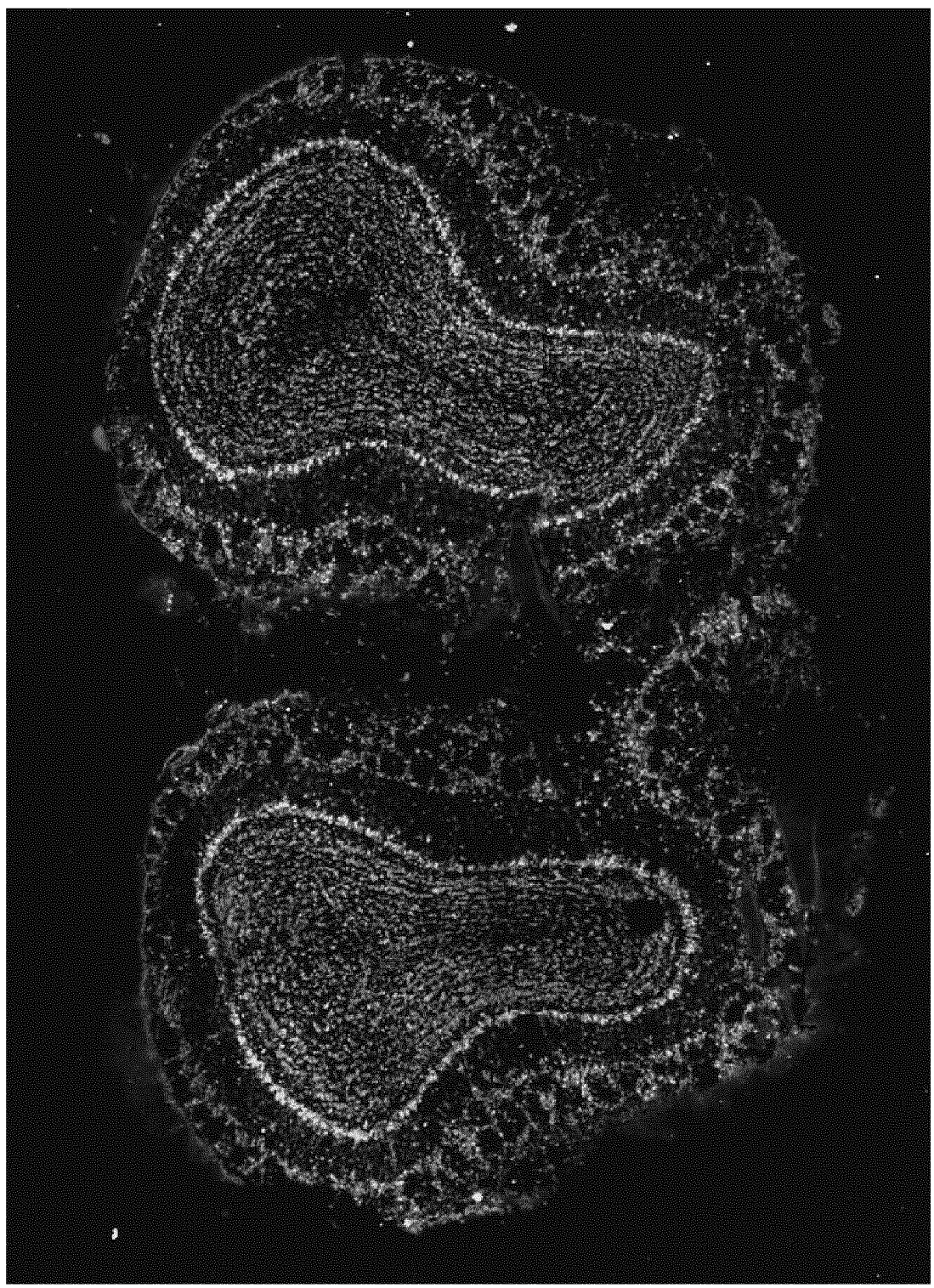
FIG. 11 shows a pattern of cDNA synthesis on array surface from a section of mouse brain olfactory bulb, as visualized by an Agilent microarray scanner.
Figure 12:
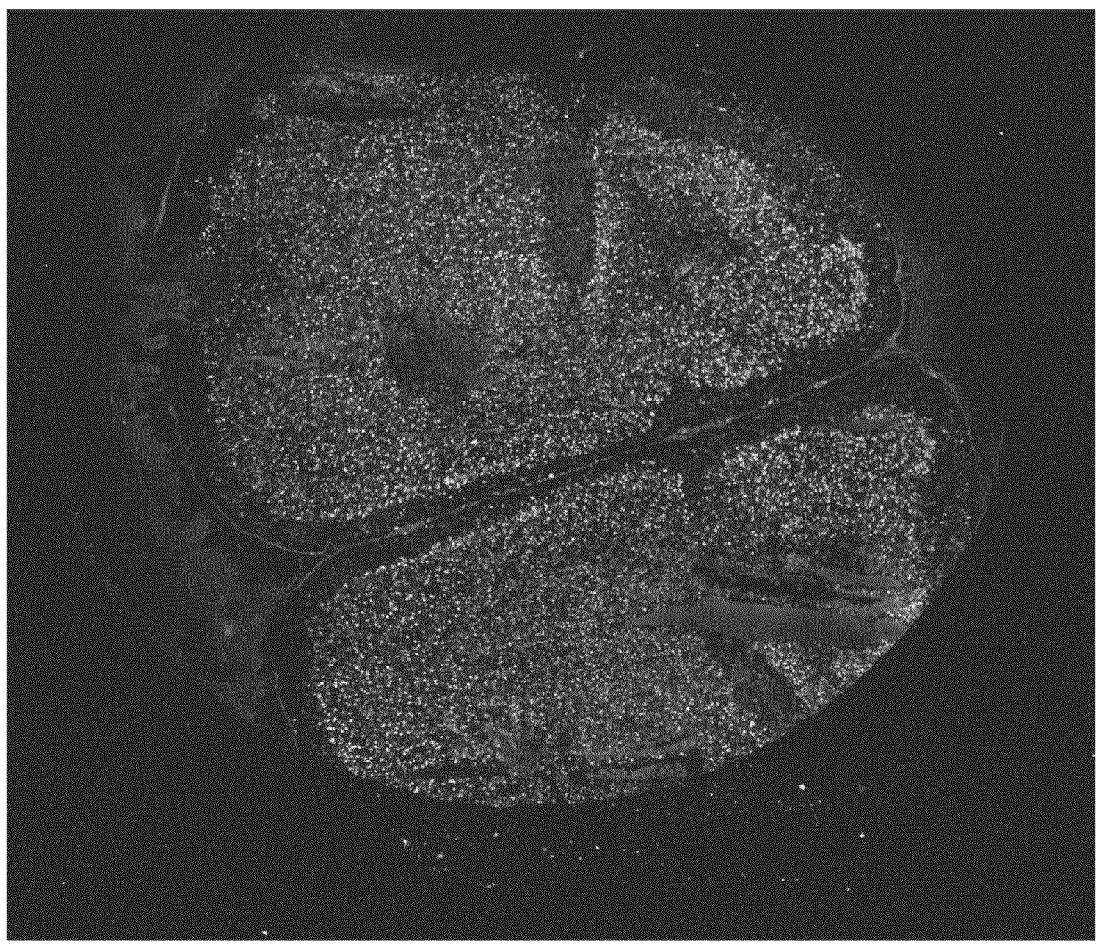
FIG. 12 shows a pattern of cDNA synthesis on array surface from a section of mouse brain cortex, as visualized by an Agilent microarray scanner.

The array was imaged at 532 nm using an Agilent microarray scanner at 100% exposure and 5 µm resolution (FIG. 11 and FIG. 12).

TABLE 2

Probe 1

Amino-C6-UUACACTCTTTCCCTACACGACGCTCTTCCGATCTGTCCGA
TATGATTGCCGCTTTTTTTTTTTTTTTTTTVN (SEQ ID NO: 47)

Example 11

The following experiments demonstrate how a portion of the secured (captured) cDNA molecules can be removed from selected parts of the surface of the object substrate, e.g. array. This enables isolation of cDNA from limited parts of the tissue section.

The method described in Example 10 was performed up to and including the step of tissue removal. Followed by the steps described below.

cDNA Removal by Laser Ablation

The array was mounted into a MMI Cellcut instrument (Molecular Machines and Industries AG, Glattbrugg, Switzerland) and the sections of the fluorescently labelled cDNA to be removed were marked for ablation by laser.

Imaging

Figure 13:
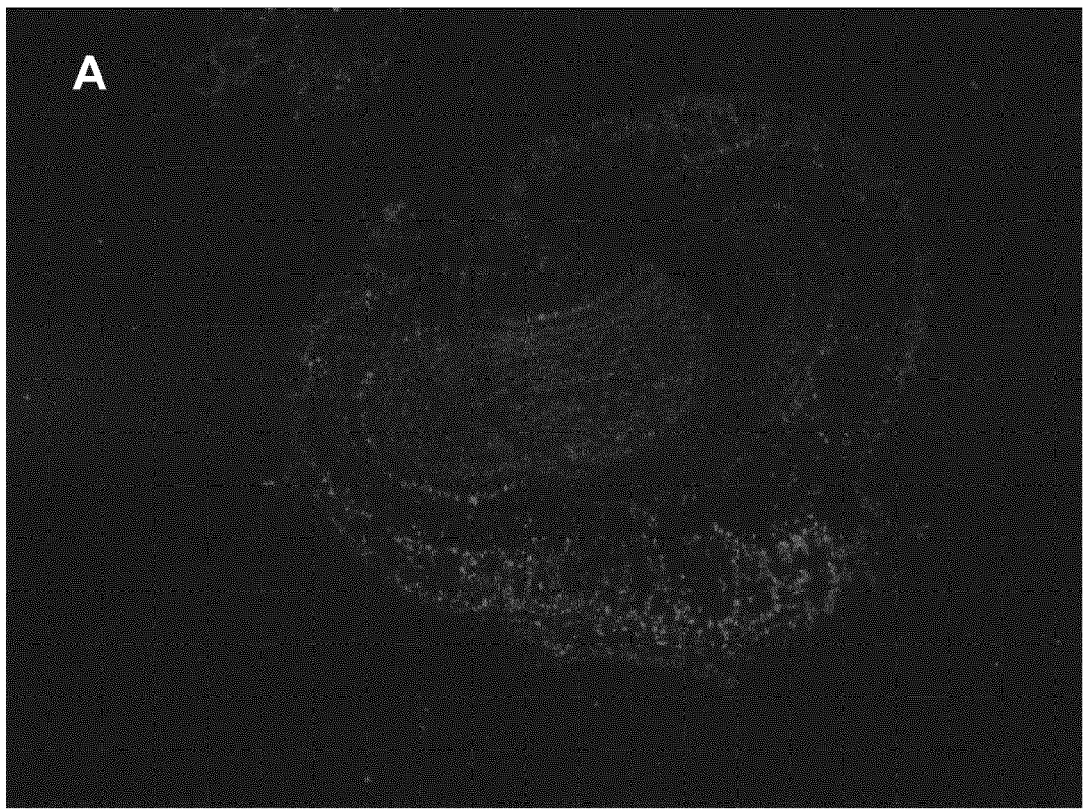
FIG. 13 shows a pattern of cDNA synthesis on array surface from a section of mouse brain olfactory bulb, before ablation (A) and after ablation of non-wanted areas (B), as imaged on the MMI cellcut instrument.
Figure 13:

The codelink glass chip was imaged at 532 nm using an Agilent microarray scanner at 100% exposure and 5 µm resolution. Removal of ablated areas was verified (FIGS. 13a and b). The array was washed according to the procedure described in Example 10.

Release of Remaining cDNA from the Array

The array was attached to an ArrayIt slide holder and 16 well mask (ArrayIt Corporation). A cleavage mixture (50 µl) containing 1× Exo I buffer (New England Biolabs, Ipswich, Mass., USA), 1×BSA, RNase/DNase free water, 5 U of USER enzyme mix (New England Biolabs) was added to each well. The reactions were covered with a plastic sealer and incubated at 37° C. for 1 hour using interval mixing of 3 seconds at 300 rpm and 6 seconds rest. After the incubation, 45 µl cleavage mixture was collected from each of the used wells and placed into 0.2 ml PCR tubes.

Exonuclease Treatment

After cooling the solutions on ice for 2 minutes, Exonuclease I (NEB) was added, to remove unextended cDNA probes, to a final volume of 46.41 and a final concentration of 0.52 U/µl. The tubes were incubated in a thermocycler (Applied Biosystems) at 37° C. for 30 minutes followed by inactivation of the exonuclease at 80° C. for 25 minutes.

dA-Tailing by Terminal Transferase

After the exonuclease step, 45 µl polyA-tailing mixture consisting of TdT Buffer (Takara), 3 mM dATP (Takara) and manufacturers TdT Enzyme mix (TdT and RNase H) (Takara), was added to each of the samples according to manufacturer's instructions. The mixtures were incubated in a thermo cycler at 37° C. for 15 minutes followed by inactivation of TdT at 70° C. for 10 minutes.

Second-Strand Synthesis and PCR-Amplification

After dA-tailing, 23 µl PCR master mix was placed into four new 0.2 ml PCR tubes per sample. 2 µl of sample was added to each tube as a template. The final PCRs consisted of 1× Ex Taq buffer (Takara), 200 µM of each dNTP (Takara), 600 nM A_primer (MWG), 600 nM B_dT20VN_primer (MWG) and 0.025 U/µl Ex Taq polymerase (Takara)(Table 3). A second cDNA strand was created by running one cycle in a thermocycler at 95° C. for 3 minutes, 50° C. for 2 minutes and 72° C. for 3 minutes. The samples were amplified by running 20 cycles (for library preparation) or 30 cycles (to confirm the presence of cDNA) at 95° C. for 30 seconds, 67° C. for 1 minute and 72° C. for 3 minutes, followed by a final extension at 72° C. for 10 minutes.

Library Cleanup

After amplification, the four PCRs (100 µl) were mixed with 500 µl binding buffer (Qiagen) and placed in a Qiaquick PCR purification column (Qiagen) and spun for 1 minute at 17,900×g in order to bind the amplified cDNA to the membrane. The membrane was then washed with wash buffer (Qiagen) containing ethanol and finally eluted into 50 µl of 10 mM Tris-Cl, pH 8.5.

The purified and concentrated sample was further purified and concentrated by CA-purification (purification by superparamagnetic beads conjugated to carboxylic acid) with an MBS robot (Magnetic Biosolutions). A final PEG concentration of 10% was used in order to remove fragments below 150-200 bp. The amplified cDNA was allowed to bind to the CA-beads (Invitrogen) for 10 min and were then eluted into 15 µl of 10 mM Tris-Cl, pH 8.5.

Library Quality Analysis

Figure 14:
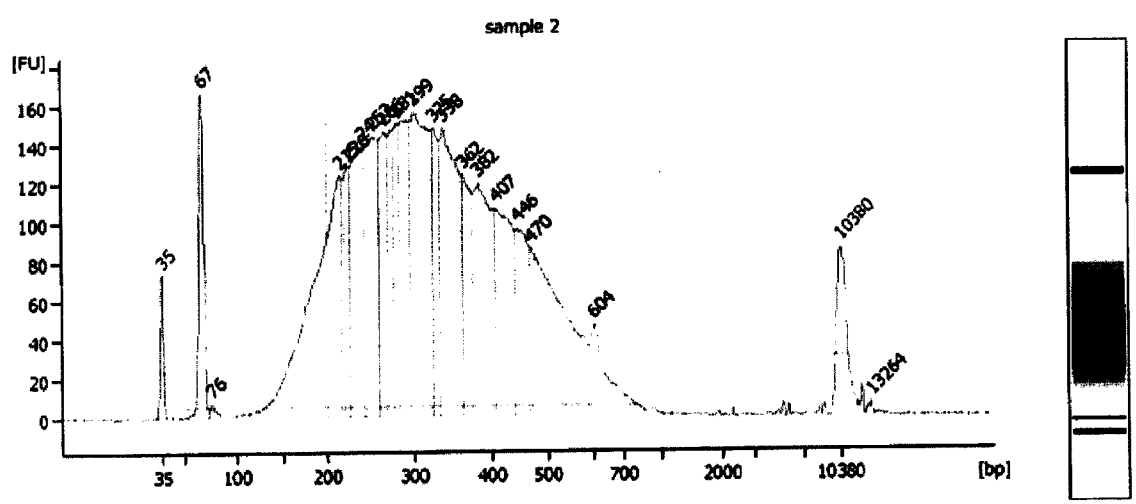
FIG. 14 shows the resulting library made from cleaved fluorescently labelled cDNA library of non-ablated areas as visualized with a DNA high sensitivity chip on an Agilent Bioanalyzer.

Samples amplified for 30 cycles were analyzed with an Agilent Bioanalyzer (Agilent) in order to confirm the presence of an amplified cDNA library, the DNA High Sensitivity kit or DNA 1000 kit were used depending on the amount of material (FIG. 14).

TABLE 3

Second strand synthesis and first PCR Amplification handles

| | |
|---|---|
| A_primer | ACACTCTTTCCCTACACGACGCTCTTCCGATCT (SEQ ID NO: 48) |
| B_dt20VN_primer | AGACGTGTGCTCTTCCGATCTTTTTTTTTTTTTTTTTTTTVN (SEQ ID NO: 49) |

TABLE 4

Oligos used for spatial transcriptomics

5' to 3'

Example 6

Nimblegen 5' to 3' arrays with free 3' end Array probes

| | |
|---|---|
| Probe1 (SEQ ID NO: 50) | UUUUUACACTCTTTCCCTACACGACGCTCTTCCGATCTGTCCGATATGATTGCCGCTTTTTTTTTTTTTTTTTTTTVN |
| Probe2 (SEQ ID NO: 51) | UUUUUACACTCTTTCCCTACACGACGCTCTTCCGATCTATGAGCCGGGTTCATCTTTTTTTTTTTTTTTTTTTTVN |
| Probe3 (SEQ ID NO: 52) | UUUUUACACTCTTTCCCTACACGACGCTCTTCCGATCTTGAGGCACTCTGTTGGGATTTTTTTTTTTTTTTTTTTTVN |
| Probe4 (SEQ ID NO: 53) | UUUUUACACTCTTTCCCTACACGACGCTCTTCCGATCTATGATTAGTCGCCATTCGTTTTTTTTTTTTTTTTTTTTVN |
| Probe5 (SEQ ID NO: 54) | UUUUUACACTCTTTCCCTACACGACGCTCTTCCGATCTACTTGAGGGTAGATGTTTTTTTTTTTTTTTTTTTTTTVN |
| Probe6 (SEQ ID NO: 55) | UUUUUACACTCTTTCCCTACACGACGCTCTTCCGATCTATGGCCAATACTGTTATCTTTTTTTTTTTTTTTTTTTTVN |
| Probe7 (SEQ ID NO: 56) | UUUUUACACTCTTTCCCTACACGACGCTCTTCCGATCTCGCTACCCTGATTCGACCTTTTTTTTTTTTTTTTTTTTVN |
| Probe8 (SEQ ID NO: 57) | UUUUUACACTCTTTCCCTACACGACGCTCTTCCGATCTGCCCACTTTCGCCGTAGTTTTTTTTTTTTTTTTTTTTTVN |
| Probe9 (SEQ ID NO: 58) | UUUUUACACTCTTTCCCTACACGACGCTCTTCCGATCTAGCAACTTTGAGCAAGATTTTTTTTTTTTTTTTTTTTTVN |
| Probe10 (SEQ ID NO: 59) | UUUUUACACTCTTTCCCTACACGACGCTCTTCCGATCTGCCAATTCGGAATTCCGGTTTTTTTTTTTTTTTTTTTTVN |
| Probe11 (SEQ ID NO: 60) | UUUUUACACTCTTTCCCTACACGACGCTCTTCCGATCTTCGCCCAAGGTAATACATTTTTTTTTTTTTTTTTTTTTVN |
| Probe12 (SEQ ID NO: 61) | UUUUUACACTCTTTCCCTACACGACGCTCTTCCGATCTTCGCATTTCCTATTCGAGTTTTTTTTTTTTTTTTTTTTVN |
| Probe13 (SEQ ID NO: 62) | UUUUUACACTCTTTCCCTACACGACGCTCTTCCGATCTTTGCTAAATCTAACCGCTTTTTTTTTTTTTTTTTTTTTVN |
| Probe14 (SEQ ID NO: 63) | UUUUUACACTCTTTCCCTACACGACGCTCTTCCGATCTGGAATTAAATTCTGATGGTTTTTTTTTTTTTTTTTTTTVN |
| Probe15 (SEQ ID NO: 64) | UUUUUACACTCTTTCCCTACACGACGCTCTTCCGATCTCATTACATAGGTGCTAAGTTTTTTTTTTTTTTTTTTTTVN |
| Probe16 (SEQ ID NO: 65) | UUUUUACACTCTTTCCCTACACGACGCTCTTCCGATCTATTGACTTGCGCTCGCACTTTTTTTTTTTTTTTTTTTTVN |
| Probe17 (SEQ ID NO: 66) | UUUUUACACTCTTTCCCTACACGACGCTCTTCCGATCTATAGTATCTCCCAAGTTCTTTTTTTTTTTTTTTTTTTTVN |
| Probe18 (SEQ ID NO: 67) | UUUUUACACTCTTTCCCTACACGACGCTCTTCCGATCTGTGCGCCTGTAATCCGCATTTTTTTTTTTTTTTTTTTTVN |
| Probe19 (SEQ ID NO: 68) | UUUUUACACTCTTTCCCTACACGACGCTCTTCCGATCTGCGCCACTCTTTAGGTAGTTTTTTTTTTTTTTTTTTTTVN |
| Probe20 (SEQ ID NO: 69) | UUUUUACACTCTTTCCCTACACGACGCTCTTCCGATCTTATGCAAGTGATTGGCTTTTTTTTTTTTTTTTTTTTTTVN |

TABLE 4-continued

Oligos used for spatial transcriptomics

5' to 3'

| | |
|---|---|
| Probe21 (SEQ ID NO: 70) | UUUUUACACTCTTTCCCTACACGACGCTCTTCCGATCTC CAAGCCACGTTTATACGTTTTTTTTTTTTTTTTTTTVN |
| Probe22 (SEQ ID NO: 71) | UUUUUACACTCTTTCCCTACACGACGCTCTTCCGATCTA CCTGATTGCTGTATAACTTTTTTTTTTTTTTTTTTTVN |
| Probe23 (SEQ ID NO: 72) | UUUUUACACTCTTTCCCTACACGACGCTCTTCCGATCTC AGCGCATCTATCCTCTATTTTTTTTTTTTTTTTTTTVN |
| Probe24 (SEQ ID NO: 73) | UUUUUACACTCTTTCCCTACACGACGCTCTTCCGATCTT CCACGCGTAGGACTAGTTTTTTTTTTTTTTTTTTTTVN |
| Probe25 (SEQ ID NO: 74) | UUUUUACACTCTTTCCCTACACGACGCTCTTCCGATCTC GACTAAGTATGTAGCGCTTTTTTTTTTTTTTTTTTTVN |

Frame probe

| | |
|---|---|
| Layout1 (SEQ ID NO: 75) | AAATTTCGTCTGCTATCGCGCTTCTGTACC |

Fluorescent marker probe

| | |
|---|---|
| PS_1 (SEQ ID NO: 76) | GGTACAGAAGCGCGATAGCAG-Cy3 |

Second strand synthesis and first PCR Amplification handles

| | |
|---|---|
| A_primer (SEQ ID NO: 77) | ACACTCTTTCCCTACACGACGCTCTTCCGATCT |
| B_dt20VN primer (SEQ ID NO: 78) | AGACGTGTGCTCTTCCGATCTTTTTTTTTTTTTTTTTTT TTVN |

Custom sequencing primer

| | |
|---|---|
| B_r2 (SEQ ID NO: 79) | TCA GAC GTG TGC TCT TCC GAT CTT TTT TTT TTT TTT TTT TTT T |

Example 7

Nimblegen 3' to 5' arrays with free 5' end Array probes

| | |
|---|---|
| Probe1 (SEQ ID NO: 80) | GCGTTCAGAGTGGCAGTCGAGATCACGCGGCAATCATAT CGGACAGATCGGAAGAGCGTAGTGTAG |
| Probe2 (SEQ ID NO: 81) | GCGTTCAGAGTGGCAGTCGAGATCACAAGATGAACCCGG CTCATAGATCGGAAGAGCGTAGTGTAG |
| Probe3 (SEQ ID NO: 82) | GCGTTCAGAGTGGCAGTCGAGATCACTCCCAACAGAGTG CCTCAAGATCGGAAGAGCGTAGTGTAG |
| Probe4 (SEQ ID NO: 83) | GCGTTCAGAGTGGCAGTCGAGATCACCGAATGGCGACTA ATCATAGATCGGAAGAGCGTAGTGTAG |
| Probe5 (SEQ ID NO: 84) | GCGTTCAGAGTGGCAGTCGAGATCACAAACATCTACCCT CAAGTAGATCGGAAGAGCGTAGTGTAG |
| Probe6 (SEQ ID NO: 85) | GCGTTCAGAGTGGCAGTCGAGATCACGATAACAGTATTG GCCATAGATCGGAAGAGCGTAGTGTAG |
| Probe7 (SEQ ID NO: 86) | GCGTTCAGAGTGGCAGTCGAGATCACGGTCGAATCAGGG TAGCGAGATCGGAAGAGCGTAGTGTAG |
| Probe8 (SEQ ID NO: 87) | GCGTTCAGAGTGGCAGTCGAGATCACACTACGGCGAAAG TGGGCAGATCGGAAGAGCGTAGTGTAG |
| Probe9 (SEQ ID NO: 88) | GCGTTCAGAGTGGCAGTCGAGATCACATCTTGCTCAAAG TTGCTAGATCGGAAGAGCGTAGTGTAG |
| Probe10 (SEQ ID NO: 89) | GCGTTCAGAGTGGCAGTCGAGATCACCCGGAATTCCGAA TTGGCAGATCGGAAGAGCGTAGTGTAG |
| Probe11 (SEQ ID NO: 90) | GCGTTCAGAGTGGCAGTCGAGATCACATGTATTACCTTG GGCGAAGATCGGAAGAGCGTAGTGTAG |

TABLE 4-continued

Oligos used for spatial transcriptomics

5' to 3'

| | |
|---|---|
| Probe12 (SEQ ID NO: 91) | GCGTTCAGAGTGGCAGTCGAGATCACCTCGAATAGGAAATGCGAAGATCGGAAGAGCGTAGTGTAG |
| Probe13 (SEQ ID NO: 92) | GCGTTCAGAGTGGCAGTCGAGATCACGGCGGTTAGATTTAGCAAAGATCGGAAGAGCGTAGTGTAG |
| Probe14 (SEQ ID NO: 93) | GCGTTCAGAGTGGCAGTCGAGATCACCCATCAGAATTTAATTCCAGATCGGAAGAGCGTAGTGTAG |
| Probe15 (SEQ ID NO: 94) | GCGTTCAGAGTGGCAGTCGAGATCACCTTAGCACCTATGTAATGAGATCGGAAGAGCGTAGTGTAG |
| Probe16 (SEQ ID NO: 95) | GCGTTCAGAGTGGCAGTCGAGATCACGTGCGAGCGCAAGTCAATAGATCGGAAGAGCGTAGTGTAG |
| Probe17 (SEQ ID NO: 96) | GCGTTCAGAGTGGCAGTCGAGATCACGAACTTGGGAGATACTATAGATCGGAAGAGCGTAGTGTAG |
| Probe18 (SEQ ID NO: 97) | GCGTTCAGAGTGGCAGTCGAGATCACTGCGGATTACAGGCGCACAGATCGGAAGAGCGTAGTGTAG |
| Probe19 (SEQ ID NO: 98) | GCGTTCAGAGTGGCAGTCGAGATCACCTACCTAAAGAGTGGCGCAGATCGGAAGAGCGTAGTGTAG |
| Probe20 (SEQ ID NO: 99) | GCGTTCAGAGTGGCAGTCGAGATCACAAGCCAATCACTTGCATAAGATCGGAAGAGCGTAGTGTAG |
| Probe21 (SEQ ID NO: 100) | GCGTTCAGAGTGGCAGTCGAGATCACCGTATAAACGTGGCTTGGAGATCGGAAGAGCGTAGTGTAG |
| Probe22 (SEQ ID NO: 101) | GCGTTCAGAGTGGCAGTCGAGATCACGTTATACAGCAATCAGGTAGATCGGAAGAGCGTAGTGTAG |
| Probe23 (SEQ ID NO: 102) | GCGTTCAGAGTGGCAGTCGAGATCACTAGAGGATAGATGCGCTGAGATCGGAAGAGCGTAGTGTAG |
| Probe24 (SEQ ID NO: 103) | GCGTTCAGAGTGGCAGTCGAGATCACACTAGTCCTACGCGTGGAAGATCGGAAGAGCGTAGTGTAG |
| Probe25 (SEQ ID NO: 104) | GCGTTCAGAGTGGCAGTCGAGATCACGCGCTACATACTTAGTCGAGATCGGAAGAGCGTAGTGTAG |
| Frame probe | |
| Layout1 (SEQ ID NO: 105) | AAATTTCGTCTGCTATCGCGCTTCTGTACC |
| Capture probe | |
| LP_Poly-dTVN (SEQ ID NO: 106) | GTGATCTCGACTGCCACTCTGAATTTTTTTTTTTTTTTTTTTVN |
| Amplification handle probe | |
| A-handle (SEQ ID NO: 107) | ACACTCTTTCCCTACACGACGCTCTTCCGATCT |
| Second strand synthesis and first PCR amplification handles | |
| A_primer (SEQ ID NO: 108) | ACACTCTTTCCCTACACGACGCTCTTCCGATCT |
| B_dt20VN_primer (SEQ ID NO: 109) | AGACGTGTGCTCTTCCGATCTTTTTTTTTTTTTTTTTTTTVN |
| Second PCR | |
| A_primer (SEQ ID NO: 110) | ACACTCTTTCCCTACACGACGCTCTTCCGATCT |
| B_primer (SEQ ID NO: 111) | GTGACTGGAGTTCAGACGTGTGCTCTTCCGATCT |

TABLE 4-continued

Oligos used for spatial transcriptomics

5' to 3'

Example 9

Template switching

| | |
|---|---|
| Templateswitch_longB (SEQ ID NO: 112) | GTGACTGGAGTTCAGACGTGTGCTCTTCCGATCTATrGrGrG |

Example 12

The following experiment demonstrates that the step of labelling the secured (captured) cDNA molecules can be performed using arrays that comprise a high density of capture probes comprising unique positional domains.

Array Preparation

Pre-fabricated high-density microarray chips were ordered from Roche-Nimblegen (Madison, Wis., USA). Each chip contained multiple probe arrays, each with 270,000 features of which 135,000 features carried a capture probe comprising a unique ID-tag sequence (positional domain) and a capture region (capture domain). Each feature was 13×13 µm in size. The capture probes were composed 5' to 3' of: a universal domain containing five dUTP bases (a cleavage domain) and a general 5' amplification domain; an ID tag (positional domain); and a capture region (capture domain) (see Table 5). Each array was also fitted with a frame of marker probes carrying a generic 30 bp sequence (Table 5) to enable hybridization of fluorescent probes to help with orientation during array visualization.

The probe-arrays were separated during reaction steps by a 16-pad mask (Arrayit Corporation, Sunnyvale, Calif., USA).

The method described in Example 10 was performed up to and including the step of tissue removal.

Imaging

A solution with frame marker probe (Table 5) at a concentration of 170 nM in PBS was prepared. This solution was added to the wells and the slide was incubated at room temperature for 5 minutes, followed by brief washing in PBS and spin drying.

Figure 15:
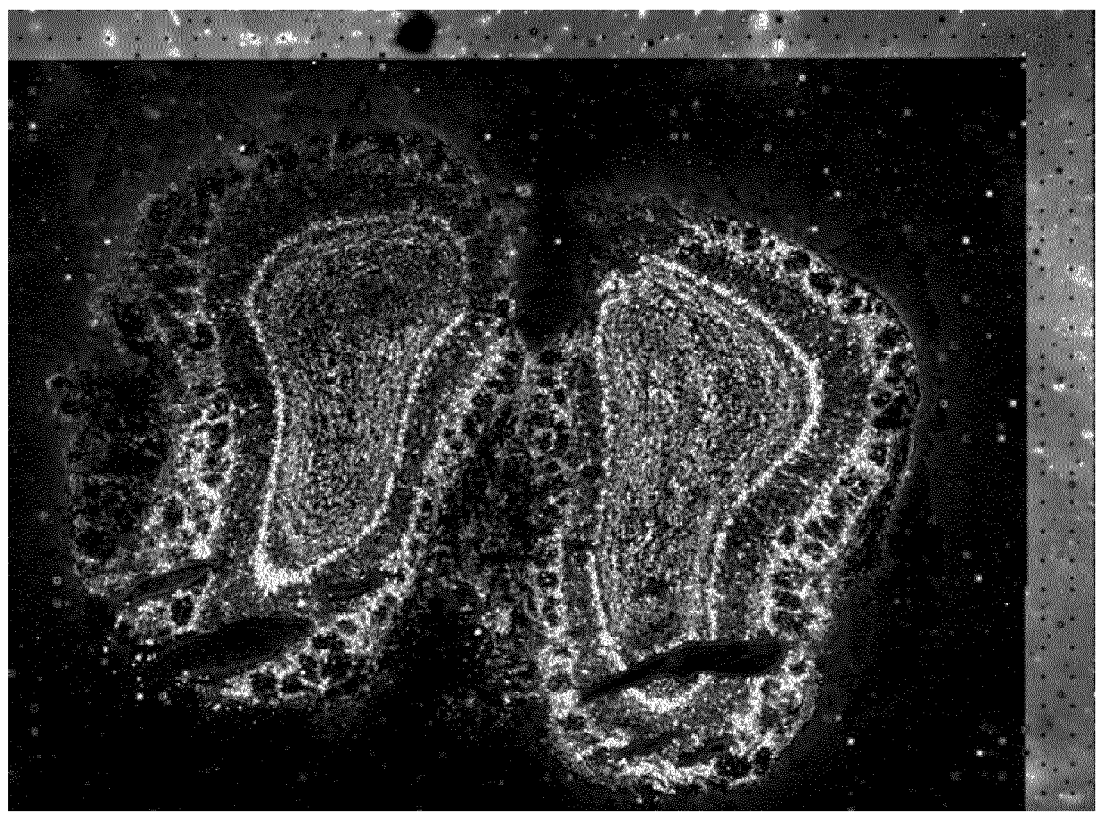
FIG. 15 shows a pattern of cDNA synthesis on a high-density feature array surface from a section of mouse brain olfactory bulb. A frame (visible at the top and to the right in the image) consisting of features containing a single DNA probe sequence was labelled by hybridization of a complementary oligonucleotide labelled with Cy3.

The high-density microarray glass chip was imaged at 532 nm using an Agilent microarray scanner at 100% exposure and 5 µm resolution (FIG. 15).

TABLE 5

Nimblegen 5' to 3' arrays with free 3' end Array probes

5' to 3'

| | |
|---|---|
| Probe1 (SEQ ID NO: 113) | UUUUUACACTCTTTCCCTACACGACGCTCTTCCGATCTG TCCGATATGATTGCCGCTTTTTTTTTTTTTTTTTTTVN |
| Probe2 (SEQ ID NO: 114) | UUUUUACACTCTTTCCCTACACGACGCTCTTCCGATCTA TGAGCCGGGTTCATCTTTTTTTTTTTTTTTTTTTTVN |
| Probe3 (SEQ ID NO: 115) | UUUUUACACTCTTTCCCTACACGACGCTCTTCCGATCTT GAGGCACTCTGTTGGGATTTTTTTTTTTTTTTTTTTVN |
| Probe4 (SEQ ID NO: 116) | UUUUUACACTCTTTCCCTACACGACGCTCTTCCGATCTA TGATTAGTCGCCATTCGTTTTTTTTTTTTTTTTTTTVN |
| Probe5 (SEQ ID NO: 117) | UUUUUACACTCTTTCCCTACACGACGCTCTTCCGATCTA CTTGAGGGTAGATGTTTTTTTTTTTTTTTTTTTTTVN |
| Probe6 (SEQ ID NO: 118) | UUUUUACACTCTTTCCCTACACGACGCTCTTCCGATCTA TGGCCAATACTGTTATCTTTTTTTTTTTTTTTTTTTVN |
| Probe7 (SEQ ID NO: 119) | UUUUUACACTCTTTCCCTACACGACGCTCTTCCGATCTC GCTACCCTGATTCGACCTTTTTTTTTTTTTTTTTTTVN |
| Probe8 (SEQ ID NO: 120) | UUUUUACACTCTTTCCCTACACGACGCTCTTCCGATCTG CCCACTTTCGCCGTAGTTTTTTTTTTTTTTTTTTTTVN |
| Probe9 (SEQ ID NO: 121) | UUUUUACACTCTTTCCCTACACGACGCTCTTCCGATCTA GCAACTTTGAGCAAGATTTTTTTTTTTTTTTTTTTTVN |
| Probe10 (SEQ ID NO: 122) | UUUUUACACTCTTTCCCTACACGACGCTCTTCCGATCTG CCAATTCGGAATTCCGGTTTTTTTTTTTTTTTTTTTVN |
| Probe11 (SEQ ID NO: 123) | UUUUUACACTCTTTCCCTACACGACGCTCTTCCGATCTT CGCCCAAGGTAATACATTTTTTTTTTTTTTTTTTTTVN |
| Probe12 (SEQ ID NO: 124) | UUUUUACACTCTTTCCCTACACGACGCTCTTCCGATCTT CGCATTTCCTATTCGAGTTTTTTTTTTTTTTTTTTTVN |

TABLE 5-continued

Nimblegen 5' to 3' arrays with free 3' end Array probes

5' to 3'

Probe13 (SEQ ID NO: 125)   UUUUUACACTCTTTCCCTACACGACGCTCTTCCGATCTT
                           TGCTAAATCTAACCGCCTTTTTTTTTTTTTTTTTTVN Probe14 (SEQ ID NO: 126)   UUUUUACACTCTTTCCCTACACGACGCTCTTCCGATCTG
                           GAATTAAATTCTGATGGTTTTTTTTTTTTTTTTTTVN Probe15 (SEQ ID NO: 127)   UUUUUACACTCTTTCCCTACACGACGCTCTTCCGATCTC
                           ATTACATAGGTGCTAAGTTTTTTTTTTTTTTTTTTVN Probe16 (SEQ ID NO: 128)   UUUUUACACTCTTTCCCTACACGACGCTCTTCCGATCTA
                           TTGACTTGCGCTCGCACTTTTTTTTTTTTTTTTTTVN Probe17 (SEQ ID NO: 129)   UUUUUACACTCTTTCCCTACACGACGCTCTTCCGATCTA
                           TAGTATCTCCCAAGTTCTTTTTTTTTTTTTTTTTTVN Probe18 (SEQ ID NO: 130)   UUUUUACACTCTTTCCCTACACGACGCTCTTCCGATCTG
                           TGCGCCTGTAATCCGCATTTTTTTTTTTTTTTTTTVN Probe19 (SEQ ID NO: 131)   UUUUUACACTCTTTCCCTACACGACGCTCTTCCGATCTG
                           CGCCACTCTTTAGGTAGTTTTTTTTTTTTTTTTTTVN Probe20 (SEQ ID NO: 132)   UUUUUACACTCTTTCCCTACACGACGCTCTTCCGATCTT
                           ATGCAAGTGATTGGCTTTTTTTTTTTTTTTTTTTVN Probe21 (SEQ ID NO: 133)   UUUUUACACTCTTTCCCTACACGACGCTCTTCCGATCTC
                           CAAGCCACGTTTATACGTTTTTTTTTTTTTTTTTTVN Probe22 (SEQ ID NO: 134)   UUUUUACACTCTTTCCCTACACGACGCTCTTCCGATCTA
                           CCTGATTGCTGTATAACTTTTTTTTTTTTTTTTTTVN Probe23 (SEQ ID NO: 135)   UUUUUACACTCTTTCCCTACACGACGCTCTTCCGATCTC
                           AGCGCATCTATCCTCTATTTTTTTTTTTTTTTTTTVN Probe24 (SEQ ID NO: 136)   UUUUUACACTCTTTCCCTACACGACGCTCTTCCGATCTT
                           CCACGCGTAGGACTAGTTTTTTTTTTTTTTTTTTTVN Probe25 (SEQ ID NO: 137)   UUUUUACACTCTTTCCCTACACGACGCTCTTCCGATCTC
                           GACTAAGTATGTAGCGCTTTTTTTTTTTTTTTTTTVN Frame probe (SEQ ID NO: 138)   AAATTTCGTCTGCTATCGCGCTTCTGTACC Fluorescent marker probe       GGTACAGAAGCGCGATAGCAG-Cy3
(SEQ ID NO: 139)

Example 13

The following experiment demonstrates that the step of labelling the secured (captured) cDNA molecules is effective at lower concentrations of fluorescently labelled nucleotides.

The method described in Example 10 was performed up to the cDNA synthesis step, which was replaced by the step described below.

cDNA Synthesis with Cy3-dNTP

For each well an 80 µl cDNA synthesis mixture was prepared containing 4 µl each of dATP/dGTP/dTTP (10 mM), 4 ul DTT (0.1M), 1×BSA, 20 U/µl Superscript III, 5 U/ul RNaseOUT, 1× first strand buffer (Superscript III, Invitrogen) and MilliQ water. The concentration of dCTP and Cy3-dCTP was varied so that in five parallel experiments 1/1, 1/2, 1/4, 1/8 and 1/16 of the original concentration of 2.5 mM for dCTP and 1 mM for Cy3-dCTP was used. 4 µl of dCTP and 4 µl of Cy3-dCTP with these concentrations were pipetted into each respective synthesis mixture. 70 µl of the reaction mixture was added to each well. The reactions were covered with a plastic sealer and incubated at 37° C. overnight.

The washing, tissue removal and imaging steps were performed according to Example 10.

Signal Quantitation

Figure 16:
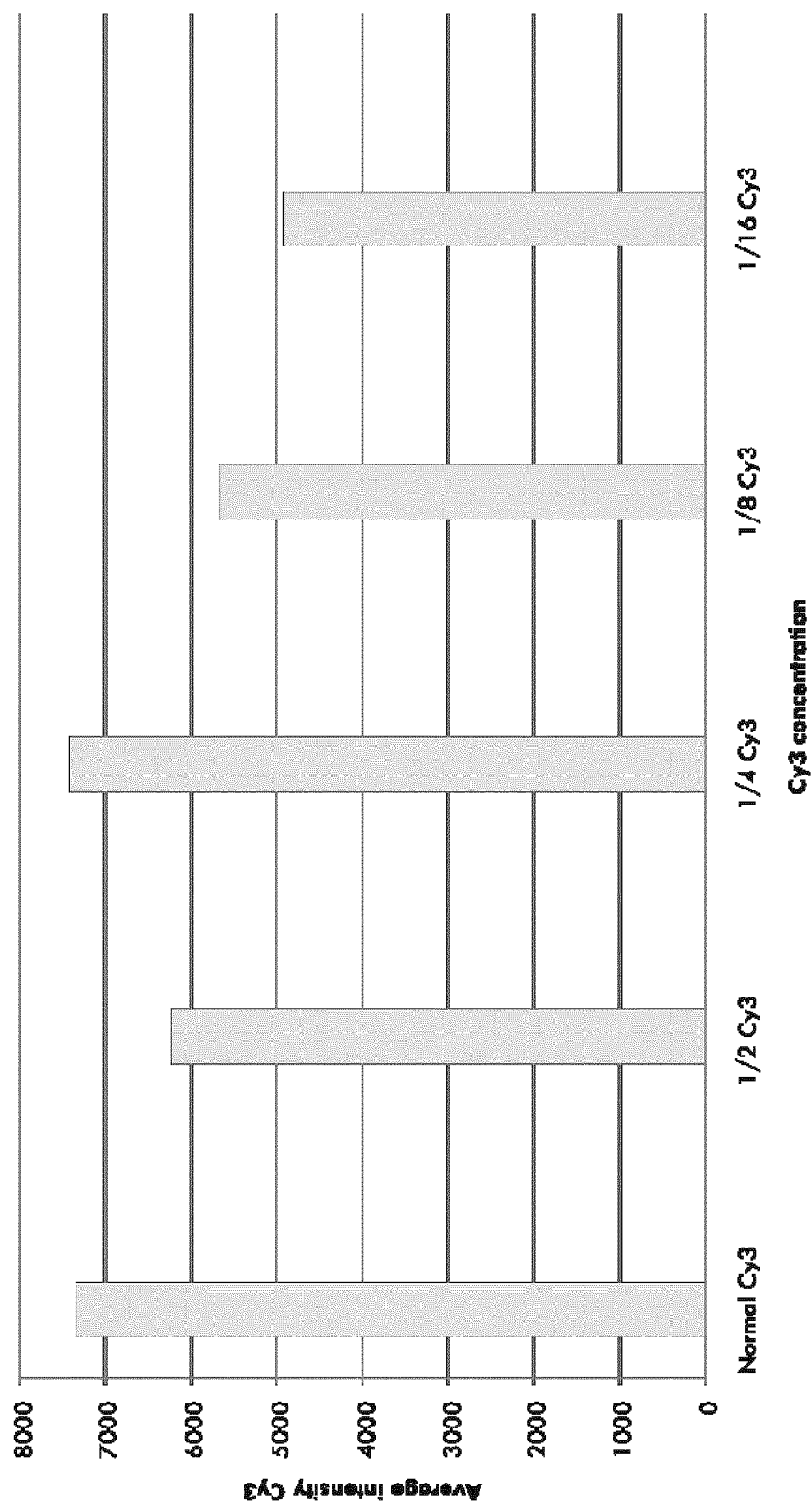
FIG. 16 shows a bar chart of Cy3 intensities on arrays using different amounts of Cy3 labelled dCTP.

The signal intensities resulting from imaging of the codelink glass chip in the Agilent microarray scanner were analyzed using the Genepix pro software. Average signal intensities were calculated from multiple selected areas within each Cy3 footprint and plotted in a diagram (FIG. 16).

Example 14

The following experiment demonstrates that a variety of tissues can be used in the methods of the invention.

The method described in Example 10 was performed up to the Imaging step. The tissue preparation, fixation and imaging steps were replaced by the steps described below.

Preparation of Fresh Frozen Tissue and Sectioning onto Capture Probe Arrays

Fresh non-fixed *drosophila* or zebrafish tissue was frozen with dry ice and subsequently mounted for sectioning with a cryostat at 10 µm. A slice of tissue was applied onto each probe array to be used.

Fixation of Tissue Section Using Methanol

The sections were fixed in a pre-chilled methanol bath at −20° C. for 10 min. After fixation, the slide was briefly washed for 10 seconds 1×PBS and heat dried at 50° C. for 15 min in an eppendorf thermomixer.

Imaging

The probe array chip with zebrafish (FIG. 17A) or *drosophila* (FIG. 17B) tissue was imaged before removal using phase-contrast imaging. Imaging after removal of tissue use the Cy3 compatible channel on a MMI Cellcut instrument mounted on an Olympus IX 81 microscope.

Example 15

The following experiment demonstrates further that a variety of tissues can be used in the methods of the invention.

The method described in Example 10 was performed up to the Imaging step. The tissue preparation, fixation, permeabilization, tissue removal and imaging steps were replaced by the steps described below.

Preparation of Fresh Frozen Tissue and Sectioning onto Capture Probe Arrays

Fresh prostate cancer tissue was trimmed if necessary, embedded in Neg-50 (Thermo Scientific) and snap frozen in liquid nitrogen. The tissue was subsequently mounted for sectioning with a cryostat at 10 µm. A slice of tissue was applied onto each probe array to be used.

Fixation of Tissue Section Using Formalin

The chip was attached to an ArrayIt 16-well mask and holder. 70 µl of 4% paraformaldehyde dissolved in PBS was added to the probe array well to cover the tissue section. The reaction was incubated at room temperature for 10 minutes. The mask was removed and the chip was washed for 10 seconds in PBS. The chip was then incubated at 50° C. for 15 minutes.

Permeabilization Using Pepsin and HCl

Pepsin was diluted to 0.1% in 0.1M HCl and was preheated to 37° C. The chip was attached to an ArrayIt 16-well mask and holder. 70 µl of the pepsin/HCl mixture was added to each well. The reaction was incubated for 10 minutes at 37° C. The wells were washed with 100 µl 0.1×SSC by pipetting.

Tissue Removal

The array was attached to an ArrayIt slide holder and 16 well mask (ArrayIt Corporation). 20 µl Proteinase K Solution (Qiagen) was added for each 150 µl Proteinase K Digest Buffer from the RNeasy FFPE kit (Qiagen). 50 µl of the final mixture was added to each well and the array was incubated at 56° C. for 1 hour. The array was washed as described in Example 10.

Imaging

Figure 17:
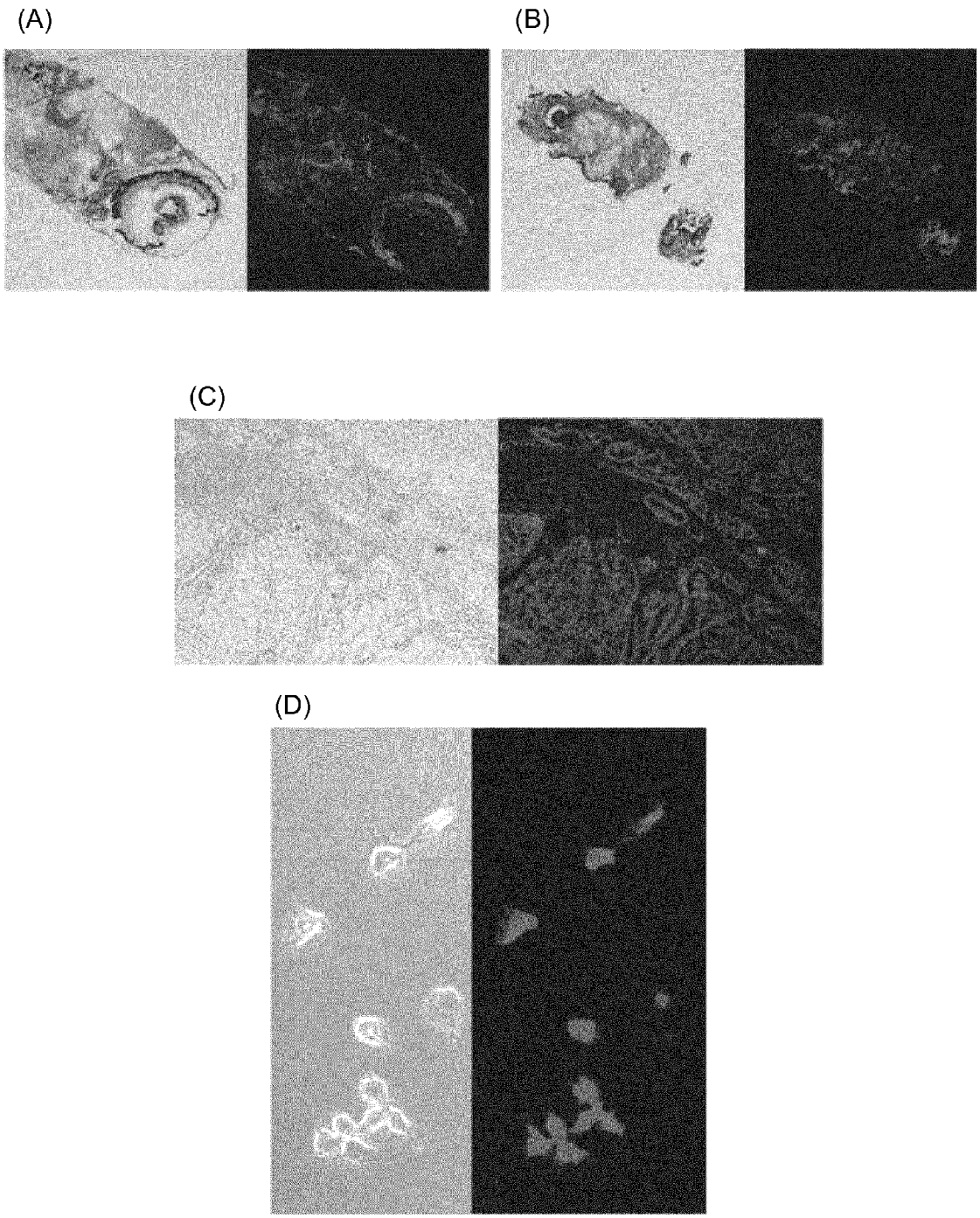
FIG. 17 shows images of cDNA synthesis on array surfaces and corresponding images of the tissue sections on the array surface using various alternative sample types, wherein: (A) depicts the phase contrast image (left) and corresponding Cy3 labelled cDNA footprint (right) of a zebra fish sample; (B) depicts the phase contrast image (left) and corresponding Cy3 labelled cDNA footprint (right) of a fruit fly (*Drosophila*) sample; (C) depicts the phase contrast image (left) and corresponding Cy3 labelled cDNA footprint (right) of a prostate tumour section; and (D) depicts the phase contrast image (left) and corresponding Cy3 labelled cDNA footprint (right) of mouse fibroblast cells.

The probe array chip with prostate tissue was imaged before removal using phase-contrast imaging. Imaging after removal of tissue use the Cy3 compatible channel on a MMI Cellcut instrument mounted on an Olympus IX 81 microscope (FIG. 17C).

Example 16

The following experiment demonstrates that a cell sample, i.e. a suspension of cells, can be used as the tissue sample in the methods of the invention.

The method described in Example 10 was performed up to the Imaging step. The tissue preparation, fixation, permeabilization, cDNA synthesis, tissue removal and imaging steps were replaced by the steps described below.

Tissue Preparation: Application of Cells onto Capture Probe Arrays

Approximately 1000-2000 mouse fibroblast cells (cell line (NIH 373)) in a 5 µl volume (in 0.1×SSC) were pipetted onto the probe array and distributed using the pipette tip. The chip was then incubated at 37° C. for 5.5 minutes.

Fixation of Cells Using Formalin

The chip was attached to an ArrayIt 16-well mask and holder. 100 ul of 4% paraformaldehyde dissolved in PBS was added to the probe array well to cover the cells. The reaction was incubated at room temperature for 10 minutes. The probe array well was washed once with 100 µl 0.1×SSC by pipetting. The chip was then incubated at 50° C. for 15 minutes.

Permeabilization Using Pepsin and HCl

Pepsin was diluted to 0.1% in 0.1M HCl and was preheated to 37° C. The chip was attached to an ArrayIt 16-well mask and holder. 70 µl of the pepsin/HCl mixture was added to each well. The reaction was incubated for 1 minute at 37° C. The wells were washed with 100 µl 0.1×SSC by pipetting.

cDNA Synthesis with Cy3-dNTP

For each well an 80 µl cDNA synthesis mixture was prepared containing 4 µl each of dATP/dGTP/dTTP (10 mM), 2 µl dCTP (2.5 mM), 2 µl Cy3-dCTP (1 mM), 4 µl DTT (0.1M), 1×BSA, 20 U/µl Superscript III, 5 U/µl RNase-OUT, 1× first strand buffer (Superscript III, Invitrogen) and MilliQ water. 70 µl of the reaction mixture was added to each well. The reactions were covered with a plastic sealer and incubated at 37° C. overnight.

Imaging

The probe array chip with cells was imaged before removal using phase-contrast imaging. Imaging after removal of tissue use the Cy3 compatible channel on a MMI Cellcut instrument mounted on an Olympus IX 81 microscope (FIG. 17D).

The invention claimed is:

1. A method for localized or spatial detection and/or analysis of RNA in a tissue sample or a portion thereof, comprising:
   (a) providing an object substrate on which at least one species of capture probe, comprising a capture domain, is directly or indirectly immobilized such that the probes are oriented to have a free 3' end to enable said probe to function as a reverse transcriptase (RT) primer;
   (b) contacting said substrate with a tissue sample and allowing RNA of the tissue sample to hybridise to the capture probes under a set of conditions;
   (c) generating cDNA molecules from the captured RNA molecules using said capture probes as RT primers;
   (d) labelling the cDNA molecules generated in step (c), wherein said labelling step may be contemporaneous with, or subsequent to, said generating step;
   (e) detecting a signal from the labelled cDNA molecules; and optionally
   (f) imaging the tissue sample, wherein the tissue sample is imaged before or after step (c).

2. The method of claim 1, being a method for determining the optimum conditions for localised or spatial detection of RNA in a tissue sample on an object substrate, comprising:
   (g) repeating steps (a)-(e), and optionally step (f), using a second set of conditions that are different to the conditions used in step (b);
   (h) comparing the intensity and/or resolution of the signal from the labelled cDNA molecules immobilised on the object substrate; and optionally
   (i) selecting, from the conditions used in step (b) and second set of conditions used in step (g), the conditions that provide the optimum signal intensity and/or resolution of the labelled cDNA molecules.

3. The method of claim 1, being a method for determining and/or analysing RNA or a transcriptome of a tissue sample or a portion thereof comprising further steps:
   (g') removing the labelled cDNA from at least one portion of the surface of the object substrate;
   (h') optionally amplifying the remaining cDNA molecules immobilised on the surface of the object substrate;
   (i') releasing at least part of the remaining cDNA molecules and/or optionally their amplicons from the surface of the object substrate, wherein said released molecules may be a first strand and/or second strand cDNA molecule or an amplicon thereof;
   (j') directly or indirectly analysing the sequence of the released molecules.

4. The method of claim 3, further comprising step (k) correlating said sequence analysis information with an image of said tissue sample, wherein the tissue sample is imaged before or after step (c).

5. The method of claim 3, wherein the at least one portion of labelled cDNA molecules is removed from of the surface of the object substrate by laser ablation.

6. The method of claim 1, being a method for determining and/or analysing RNA or a transcriptome of a tissue sample or a portion thereof comprising:
   (a") providing an object substrate on which multiple species of capture probes are directly or indirectly immobilized such that each species occupies a distinct position on the object substrate and is oriented to have a free 3' end to enable said probe to function as a reverse transcriptase (RT) primer, wherein each species of said capture probe comprises a nucleic acid molecule with 5' to 3':
(i) a positional domain that corresponds to the position of the capture probe on the object substrate, and
(ii) a capture domain;
(b") contacting said object substrate with a tissue sample such that the position of a capture probe on the object substrate may be correlated with a position in the tissue sample and allowing RNA of the tissue sample to hybridise to the capture domain in said capture probes under a set of conditions;
(c") generating cDNA molecules from the captured RNA molecules using said capture probes as RT primers,
(d") labelling the cDNA molecules generated in step (c'), wherein said labelling step may be contemporaneous with, or subsequent to, said generating step;
(e") detecting a signal from the labelled cDNA molecules;
(f') optionally imaging the tissue sample, wherein the tissue sample is imaged before or after step (c");
(g") optionally removing the labelled cDNA from at least one portion of the surface of the object substrate;
(h") optionally amplifying the cDNA molecules immobilized on the surface of the object substrate;
(i") releasing at least part of the cDNA molecules and/or optionally their amplicons from the surface of the object substrate, wherein said released molecules may be a first strand and/or second strand cDNA molecule or an amplicon thereof and wherein said part includes the positional domain or a complement thereof;
(j") directly or indirectly analysing the sequence of the released molecules.

7. The method of claim 6, wherein the molecules are released from the surface of the object substrate by:
(i) nucleic acid cleavage;
(ii) denaturation; and/or
(iii) physical means.

8. The method of claim 7, wherein the molecules are released by enzymatic cleavage of a cleavage domain, which is located in the universal domain or positional domain of the capture probe; or wherein the molecules are released by applying hot water or buffer to the object substrate.

9. The method of claim 6, further comprising a step of washing the object substrate to remove residual tissue.

10. The method of claim 6, wherein each species of capture probe is immobilized on the object substrate by bridge amplification to form a local clonal colony of capture probe such that each species of capture probe occupies a distinct position on the object substrate.

11. The method of claim 6, wherein the object substrate is a bead array.

12. The method of claim 11, wherein each species of capture probe is immobilized on a different bead such that each species of capture probe occupies a distinct position on the object substrate.

13. The method of claim 1, further comprising a step of correlating the signal detected from the labelled cDNA molecules with an image of said tissue sample, wherein the tissue sample is imaged before or after step (c).

14. The method of claim 1, wherein the label is incorporated into the cDNA molecules generated in step (c).

15. The method of claim 14, wherein the label is conjugated to a nucleotide and the step of labelling comprises the incorporation of labelled nucleotides into the synthesized cDNA molecule.

16. The method of claim 15, wherein the labelled nucleotides are fluorescently labelled nucleotides.

17. The method of claim 1, wherein the step of detecting a signal from the labelled cDNA molecules comprises imaging the substrate such that the signal from the labelled cDNA molecules is detected.

18. The method of claim 17, being a method for the identification of transcriptionally active tumour cells, wherein the tissue sample is a cell suspension comprising tumour cells and the image of the labelled cDNA corresponds to transcriptionally active cells.

19. The method of claim 17, wherein the substrate is imaged using light, bright field, dark field, phase contrast, fluorescence, reflection, interference or confocal microscopy or a combination thereof.

20. The method of claim 1, wherein the capture probes are DNA molecules.

21. The method of claim 1, wherein the capture probes further comprise a positional domain which is 5' relative to the capture domain, wherein said positional domain comprises a sequence that corresponds to the position of the capture probe on the object substrate.

22. The method of claim 21, wherein the positional domain of each species of capture probe comprises a unique barcode sequence.

23. The method of claim 1, wherein the capture probes further comprise a universal domain which is 5' relative to the capture domain or, if present the positional domain, wherein said universal domain comprises:
(i) an amplification domain, for amplifying the generated DNA molecules; and/or
(ii) a cleavage domain for releasing the generated DNA molecules from the surface of the object substrate.

24. The method of claim 1, wherein the capture domain comprises a poly-T or poly-U DNA oligonucleotide comprising at least 10 deoxythymidine and/or deoxyuridine residues and/or a random or degenerate oligonucleotide sequence.

25. The method of claim 1, wherein the capture probes are directly immobilized on the object substrate surface by their 5' end.

26. The method of claim 1, wherein the capture probes are indirectly immobilized on the object substrate surface by hybridization to a surface probe, wherein the capture domain of the capture probes comprises an upstream sequence that is capable of hybridizing to 5' end of surface probes that are immobilized on the object substrate.

27. The method of claim 26, wherein the surface probes are immobilized to the object substrate surface by their 3' ends.

28. The method of claim 26, wherein the surface probes comprise a sequence that is complementary to:
(i) at least part of the capture domain; and
(ii) at least part of the universal amplification domain.

29. The method of claim 28, wherein the surface probes further comprise a sequence that is complementary to the positional domain.

30. The method of claim 1, wherein the object substrate is composed of a material selected from the group consisting of glass, silicon, poly-L-lysine coated material, nitrocellulose, polystyrene, cyclic olefin copolymers (COCs), cyclic olefin polymers (COPs), polypropylene, polyethylene and polycarbonate.

31. The method of claim 1, wherein the tissue sample is a tissue section or a cell suspension.

32. The method of claim 1, wherein the object substrate comprises at least one positional marker to enable orientation of the tissue sample on the object substrate.

33. The method of claim 32, wherein the positional marker is capable of hybridizing to a labelled marker nucleic acid molecule.

34. The method of claim 32, wherein the positional marker is capable of hybridizing to a fluorescently labelled marker nucleic acid molecule.

35. The method of claim 1, wherein the tissue sample is imaged using light, bright field, dark field, phase contrast, fluorescence, reflection, interference or confocal microscopy or a combination thereof.

36. The method of claim 35, wherein the tissue sample is imaged using fluorescence microscopy.

37. The method of claim 1, comprising a step of modifying the tissue sample prior to the step of contacting the tissue sample with the substrate and/or prior to the step of generating the cDNA molecules on the substrate.

38. The method of claim 37, wherein the step of modifying the tissue sample comprises dissecting the tissue sample.

39. The method of claim 38, wherein the tissue sample is dissected using laser capture microdissection (LCM).

40. The method of claim 1, wherein the object substrate is an array substrate that is suitable for use as a sequencing platform.

41. The method of claim 40, wherein the object substrate is an array substrate that is suitable for use in next generation sequencing technologies.

42. The method of claim 1, wherein the capture probe is immobilized on the object substrate by bridge amplification.

43. The method of claim 1, wherein the object substrate is a bead array.

* * * * *